US 7,037,676 B2

(12) United States Patent
Carroll et al.

(10) Patent No.: US 7,037,676 B2
(45) Date of Patent: May 2, 2006

(54) DROSOPHILA TUMOR NECROSIS FACTOR CLASS MOLECULE POLYNUCLEOTIDES AND VARIANTS THEREOF

(75) Inventors: Pamela M. Carroll, Princeton, NJ (US); Jian Chen, Princeton, NJ (US); Chandra S. Ramanathan, Wallingford, CT (US); Hong Xiao, Princeton Junction, NJ (US); Michael A. Bowen, Lawrenceville, NJ (US)

(73) Assignee: Bristol-Myers Squibb, Princeton, NJ (US)

( * ) Notice: Subject to any disclaimer, the term of this patent is extended or adjusted under 35 U.S.C. 154(b) by 39 days.

(21) Appl. No.: 09/813,329

(22) Filed: Mar. 20, 2001

(65) Prior Publication Data

US 2002/0012968 A1 Jan. 31, 2002

Related U.S. Application Data

(60) Provisional application No. 60/190,816, filed on Mar. 21, 2000.

(51) Int. Cl.
*C12P 21/06* (2006.01)
*C12N 15/09* (2006.01)
*C12N 15/19* (2006.01)
*C07H 21/04* (2006.01)

(52) U.S. Cl. ............... 435/69.1; 435/70.1; 435/69.5; 435/69.7; 435/320.1; 435/325; 536/23.1; 536/23.4; 536/24.3; 424/185.1; 424/192.1

(58) Field of Classification Search ............ 435/69.1, 435/69.5, 70.1, 325, 320.1, 69.7; 536/23.1, 536/23.4, 24.3; 424/185.1, 192.1
See application file for complete search history.

(56) References Cited

FOREIGN PATENT DOCUMENTS

| WO | WO0055178 | 9/2000 |
|----|-----------|--------|
| WO | WO0076308 A1 | 12/2000 |
| WO | WO0171042 A2 | 9/2001 |

OTHER PUBLICATIONS

Scott et al., The Pendred syndrome gene encodes a chloride-iodide transport system. (1999), Nature Genetics (21), pp. 440–443.*
Ngo et al., 1994, The Protein Folding Problem and Tertiary Structure Prediction, pp. 492–495.*
Wells, Aditivity of Mutational Effects in Proteins, 1990, Biochemistry, vol. 26, No: 37, pp. 8509–8517.*
Celinker et al (1998), AC005974.*
NCBI Entrez Accession No: AA201867 (gi:1797632), Berkeley *Drosophila* Genome Project, entry created Jan. 24, 1997.
NCBI Entrez Accession No: AAF58848 (gi:7303801), Adams, et al., Feb. 14, 2003.
NCBI Entrez Accession No: AAM51093 (gi:21430830), Stapleton, et al., Jun. 16, 2002.
NCBI Entrez Accession No: AAM76710 (gi:21717646), Moreno, et al., Aug. 14, 2002.
NCBI Entrez Accession No: AB073865 (gi:21623741), Igaki, et al., Jun. 27, 2002.
NCBI Entrez Accession No: AF053712 (gi:3057145), Lacey, et al., May 9, 1998.
NCBI Entrez Accession No: AF521176 (gi:21717645), Moreno, et al., Aug. 14, 2002.
NCBI Entrez Accession No: A1260099 (gi:3867624), Berkeley *Drosophila* Genome Project, entry created Nov. 12, 1998.
NCBI Entrez Accession No: AY119233 (gi:21430829), Stapleton, et al., Jun. 16, 2002.
NCBI Entrez Accession No: AC005974 (gi:3893034), Celniker, et al., Nov. 19, 1998.
NCBI Entrez Accession No: BAC00950 (gi:21623742), Igaki, et al., Jun. 27, 2002.
NCBI Entrez Accession No: O14788 (gi:12643360), Anderson, et al., Mar. 15, 2004.
Hollenbaugh, et al., "Construction of Immunoglobulin Fusion Proteins", Current Protocols in Immunology, pp. 10.19A–10.19A, 11 (2002).
Igaki et al. (2002) European Mol. Biol. Organization 3009–3018.
Moreno et al. (2002) Current Biology 12:1263–1268.
Okano et al. (1991) J. of Neurochemistry 56(2) 560–567.
Cunningham et al. (1989) Science 244:1081–1085.
Subasinghe et al. (1988) Nucleic Acids Research 16:3209–3221.
Thompson et al. (1994) Nucleic Acids Research 22:4673–4680.

* cited by examiner

*Primary Examiner*—Janet Andres
*Assistant Examiner*—Jegatheesan Seharaseyon
(74) *Attorney, Agent, or Firm*—Stephen C. D'Amico; Christopher A. Klein

(57) ABSTRACT

The present invention provides novel polynucleotides encoding *Drosophila* DmTNF polypeptides, fragments and homologs thereof. The present invention also is directed to novel polynucleotides encoding two Drosophila DmTNF variants, DmTNFv1 and DmTNFv2 polypeptides, fragments and homologs thereof. Also provided are vectors, host cells, antibodies, and recombinant and synthetic methods for producing said polypeptides. The invention further relates to screening methods for identifying agonists and antagonists of the polynucleotides and polypeptides of the present invention, in addition to methods of genetically modifying Drosophila or cultured cells to express or mis-express DmTNF, DmTNFv1, or DmTNFv2. The invention also relates to the use of such modified insects or cells to characterize DmTNF activity, identify TNF-like genes and/or genes implicated in modulating TNF, characterize TNF signaling pathways, and/or to identify modulators of DmTNF activity.

22 Claims, 18 Drawing Sheets

Figure 1A

Figure 7:
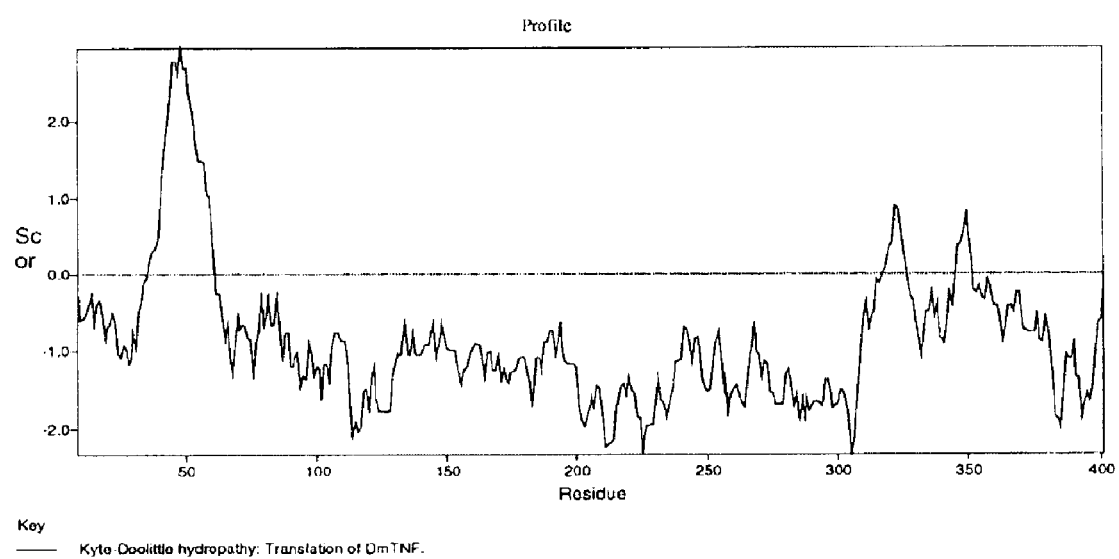

```
   1  CCACTGTGCTGGGAATTCGGCACGAGGCGAACGGACGTTTAAAGTGAGAAAAGAAACCGG    60

61  TAAATCAGAGATCCCAAGCAAGCGCGTGCGTGCATGATAGCGAAGAAAAAAAGCTATCCG   120

121  TTTCAGTTAACTACTTACCAAGATTGAATTTCGCCATCGGGCAAATTACTAAAAATACAT   180

181  AAGTGCAACTCGTCCACTGTGTGTTGTGTTTTTTTTTTTTTTTTGGTTTTCGCTGTGCC    240

241  TTTATCGCAAACAAGAACTGATAAAACTAGAAAATATCTTGAGAAACTTGTTTTCGCGCT   300

301  TTTCTTTTGCTAATTGCCGATCGCGGAAGAGAAAAACAAGCAGTAGACAAAACAAGTGTG   360

361  GTAATACAATCTGAAAAGGGCACCATCAGCAGCCCGAGGGGTTTATCTATATAGATGTCG   420

421  CAGCTTATCATCTCATGCTGTCTGTGAGGTTGTTCTGTGTGCTCGTGTAGTATCTTAAAT   480

481  ACATAGAGTGTGTTCATATAAAGTGCGACAAAGCTCGATTGGAAACAGCTGTCGAGTGCC   540

541  CTTGAGTGGGTGGGCAAGATCGTCATCATCATCATCGTCGTCATTATCAACAGAATCAGC   600

601  ATCAGCATCTGGAGGCCCCGGATGCTCTAAGATCCCCAGTGTTCATCAATTATGACTGCC   660
   1                                                        M  T  A    3

661  GAGACCCTCAAGCCGTTTATAACGCCAACGAGTGCCAACGATGATGGTTTTCCGGCCAAA   720
   4   E  T  L  K  P  F  I  T  P  T  S  A  N  D  D  G  F  P  A  K    23

721  GCGACCAGCACGGCGACCGCCCAGCGACGCACCCGCCAGCTGATCCCCCTGGTTTTGGGG   780
  24   A  T  S  T  A  T  A  Q  R  R  T  R  Q  L  I  P  L  V  L  G    43

781  TTCATCGGTCTGGGGCTGGTCGTTGCCATTCTCGCACTAACGATCTGGCAGACAACGCGT   840
  44   F  I  G  L  G  L  V  V  A  I  L  A  L  T  I  W  Q  T  T  R    63

841  GTATCGCATCTGGACAAGGAGCTGAAGAGCCTGAAGCGAGTCGTCGATAATCTCCAGCAG   900
  64   V  S  H  L  D  K  E  L  K  S  L  K  R  V  V  D  N  L  Q  Q    83

901  CGTTTGGGCATAAACTATCTGGACGAGTTCGACGAGTTCCAAAAGGAGTACGAGAATGCC   960
  84   R  L  G  I  N  Y  L  D  E  F  D  E  F  Q  K  E  Y  E  N  A   103

961  CTCATCGACTATCCAAAAAAGGTGGATGGCCTCACGGATGAGGAGGACGACGACGATGGC  1020
 104   L  I  D  Y  P  K  K  V  D  G  L  T  D  E  E  D  D  D  D  G   123
```

Figure 1B

```
1021  GATGGTCTGGATTCCATTGCGGACGACGAGGACGACGACGTTAGCTATAGCTCTGTGGAT  1080
 124   D  G  L  D  S  I  A  D  D  E  D  D  D  V  S  Y  S  S  V  D   143

1081  GATGTTGGCGCAGACTACGAGGACTACACCGATATGTTAAATAAACTCAACAATGCACAT  1140
 144   D  V  G  A  D  Y  E  D  Y  T  D  M  L  N  K  L  N  N  A  H   163

1141  ACCGGCACCACGCCCACATCTGAGACCACTGCTGAGGGCGAGGGCGAGACGGACAGTGCA  1200
 164   T  G  T  T  P  T  S  E  T  T  A  E  G  E  G  E  T  D  S  A   183

1201  TCCTCAGCCTCAAATGATGACAATGTGTTCGATGACTTTACCAGCTCAGATGCCCTCAAA  1260
 184   S  S  A  S  N  D  D  N  V  F  D  D  F  T  S  S  D  A  L  K   203

1261  AAGAAGCAGGAGAGAAAATCTCGCTCGATTGCCGATGTACGCAATGAGGAGCAGAATATT  1320
 204   K  K  Q  E  R  K  S  R  S  I  A  D  V  R  N  E  E  Q  N  I   223

1321  CAAGGAAATCACACAGAGCTTCAGGAAAAGTCATCCAATGAGGCAGCTTCCAAAGAGAGC  1380
 224   Q  G  N  H  T  E  L  Q  E  K  S  S  N  E  A  A  S  K  E  S   243

1381  CCTGCAGCACTTCACCTCCGTCGCAGAATGCATTCCCGCCATCGCCACCTCGTAGTCCGC  1440
 244   P  A  A  L  H  L  R  R  R  M  H  S  R  H  R  H  L  V  V  R   263

1441  AAAGCCAGATCCGAGGACTCGAGGCCAGCAGCCCATTTCCACTTGAGCAGCAGGCGGCGT  1500
 264   K  A  R  S  E  D  S  R  P  A  A  H  F  H  L  S  S  R  R  R   283

1501  CACCAAGAAAGTATGGGCTACCATGGAGATATGTACATAGAAAATGATAGGGAGAGATGC  1560
 284   H  Q  E  S  M  G  Y  H  G  D  M  Y  I  E  N  D  R  E  R  C   303

1561  TCTTATCAGGGACACTTTCAAACGCGCGATGGCGTATTGACGGTGACCAATGCAGGCCTA  1620
 304   S  Y  Q  G  H  F  Q  T  R  D  G  V                            323
```
```
1621  TATTACGTATACGCCCAGATATGGGGCTACAACTCGCACGACCAGAACGGATTTATCGTC  1680
 324                               G  Y  N  S  H  D  Q  N  G  F  I  V   343
```
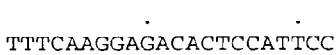
```
1681  TTTCAAGGAGACACTCCATTCCTGCAGTGCTTGAACACGGTGCCCACCAACATGCCACAT  1740
 344   F  Q  G  D  T  P  F  L  Q  C  L  N  T  V  P  T  N  M  P  H   363

1741  AAGGTGCACACCTGCCACACGAGTGGTCTGATCCACCTGGAACGAAACGAGAGGATCCAT  1800
 364   K  V  H  T  C  H  T  S  G  L  I  H  L  E  R  N  E  R  I  H   383

1801  CTGAAGGACATTCACAACGATCGCAATGCAGTTCTGCGGGAGGGAAACAACCGAAGCTAC  1860
 384   L  K  D  I  H  N  D  R  N  A  V  L  R  E  G  N  N  R  S  Y   403
```

Figure 1C

```
1861  TTTGGCATCTTCAAGGTGTAAATTGGAGAGATTATCCCCGGTCAGAAGATGGAATACCAG  1920
 404   F   G   I   F   K   V                                        409

1921  TTTAAGCTTTTGTCCCCGCGACTGCTCGTGAATGCGATTCATCGCCAGCGTGAATCCATT  1980

1981  AGTTCGTAGTACCTAGTCTTAGTCACTCCAAACCTAATCTCAATCGGAATCGTGCATACT  2040

2041  GCATTAGTCAGAAGACGGAGGAAAATCATATTTATTTTGTATATACTCGTTCGACTCTAA  2100

2101  AAAGTGAATAAAAATATATGTAGCTATTAAAAAAAAAAAAAAAAAAAAAAAAAAAAAAAC  2160

2161  CTCGAG  2166
```

Figure 2A

```
  1 ATGACTGCCGAGACCCTCAAGCCGTTTATAACGCCAACGAGTGCCAACGATGATGGTTTT  60
  1  M  T  A  E  T  L  K  P  F  I  T  P  T  S  A  N  D  D  G  F   20

61 CCGGCCAAAGCGACCAGCACGGCGACCGCCCAGCGACGCACCCGCCAGCTGATCCCCCTG 120
 21  P  A  K  A  T  S  T  A  T  A  Q  R  R  T  R  Q  L  I  P  L   40

121 GTTTTGGGGTTCATCGGTCTGGGGCTGGTCGTTGCCATTCTCGCACTAACGATCTGGCAG 180
 41  V  L  G  F  I  G  L  G  L  V  V  A  I  L  A  L  T  I  W  Q   60

181 ACAACGCGTGTATCGCATCTGGACAAGGAGCTGAAGAGCCTGAAGCGAGTCGTCGATAAT 240
 61  T  T  R  V  S  H  L  D  K  E  L  K  S  L  K  R  V  V  D  N   80

241 CTCCAGCAGCGTTTGGGCATAAACTATCTGGACGAGTTCGACGAGTTCCAAAAGGAGTAC 300
 81  L  Q  Q  R  L  G  I  N  Y  L  D  E  F  D  E  F  Q  K  E  Y  100

301 GAGAATGCCCTCATCGACTATCCAAAAAAGGTGGATGGCCTCACGGATGAGGAGGACGAC 360
101  E  N  A  L  I  D  Y  P  K  K  V  D  G  L  T  D  E  E  D  D  120

361 GACGATGGCGATGGTCTGGATTCCATTGCGGACGACGAGGACGACGACGTTAGCTATAGC 420
121  D  D  G  D  G  L  D  S  I  A  D  D  E  D  D  D  V  S  Y  S  140

421 TCTGTGGATGATGTTGGCGCAGACTACGAGGACTACACCGATATGTTAAATAAACTCAAC 480
141  S  V  D  D  V  G  A  D  Y  E  D  Y  T  D  M  L  N  K  L  N  160

481 AATGCACATACCGGCACCACGCCCACATCTGAGACCACTGCTGAGGGCGAGGGCGAGACG 540
161  N  A  H  T  G  T  T  P  T  S  E  T  T  A  E  G  E  G  E  T  180

541 GACAGTGCATCCTCAGCCTCAAATGATGACAATGTGTTCGATGACTTTACCAGCTACAAT 600
181  D  S  A  S  S  A  S  N  D  D  N  V  F  D  D  F  T  S  Y  N  200

601 GCCCACAAAAAGAAGCAGGAGAGAAAATCTCGCTCGATTGCCGATGTACGCAATGAGGAG 660
201  A  H  K  K  K  Q  E  R  K  S  R  S  I  A  D  V  R  N  E  E  220

661 CAGAATATTCAAGGAAATCACACAGAGCTTCAGGAAAAGTCATCCAATGAGGCAACTTCC 720
221  Q  N  I  Q  G  N  H  T  E  L  Q  E  K  S  S  N  E  A  T  S  240

721 AAAGAGAGAATGCATTCCCGCCATCGCCACCTCCTAGTCCGCAAAGGTGAATCTCTTCTT 780
241  K  E  R  M  H  S  R  H  R  H  L  L  V  R  K  G  E  S  L  L  260

781 TCAGCCAGATCCGAGGACTCGAGGCCAGCAGCCCATTTCCACTTGAGCAGCAGGCGGCGT 840
261  S  A  R  S  E  D  S  R  P  A  A  H  F  H  L  S  S  R  R  R  280

841 CACCAAGGAAGTATGGGCTACCATGGAGATATGTACATAGGAAATGATAACGAGAGAAAC 900
281  H  Q  G  S  M  G  Y  H  G  D  M  Y  I  G  N  D  N  E  R  N  300
```

Figure 2B

```
 901  TCTTATCAGGGACACTTTCAAACGCGCGATGGCGTCTTGACGGTGACCAATACAGGCCTA   960
 301   S   Y   Q   G   H   F   Q   T   R   D   G   V   L   T   V   T   N   T   G   L    320

961  TATTACGTATACGCCCAGATATGCTACAACAACTCGCACGACCAGAACGGATTTATCGTC  1020
 321   Y   Y   V   Y   A   Q   I   C   Y   N   N   S   H   D   Q   N   G   F   I   V    340

1021  TTTCAAGGAGACACTCCATTCCTGCAGTGCTTGAACACGGTGCCCACCAACATGCCACAT  1080
 341   F   Q   G   D   T   P   F   L   Q   C   L   N   T   V   P   T   N   M   P   H    360

1081  AAGGTGCACACCTGCCACACGAGTGGTCTGATCCACCTGGAACGAAACGAGAGGATCCAT  1140
 361   K   V   H   T   C   H   T   S   G   L   I   H   L   E   R   N   E   R   I   H    380

1141  CTGAAGGACATTCACAACGATCGCAATGCAGTTCTGCGGGAGGGAAACAACCGAAGCTAC  1200
 381   L   K   D   I   H   N   D   R   N   A   V   L   R   E   G   N   N   R   S   Y    400

1201  TTTGGCATCTTCAAGGTGTAA  1221
 401   F   G   I   F   K   V    406
```

Figur 3A

```
  1 GGCACGAGGCGAACGGACGTTTAAAGTGAGAAAAGAAACCGGTAAATCAGAGATCCCAAG   60

61 CAAGCGCGTGCGTGCATGATAGCGAAGAAAAAAGCTATCCGTTTCAGTTAACTACTTAC   120

121 CAAGATTGAATTTCGCCATCGGGCAAATTACTAAAAATACATAAGTGCAACTCGTCCACT  180

181 GTGTGTTGTGTTTTTTTTTTTTTTTTGGTTTTCGCTGTGCCTTTATCGCAAACAAGAAC   240

241 TGATAAAACTAGAAAATATCTTGAGAAACTTGTTTTCGCGCTTTTCTTTTGCTAATTGCC  300

301 GATCGCGGAAGAGAAAAACAAGCAGTAGACAAAACAAGTGTGGTAATACAATCTGAAAAG  360

361 GGCACCATCAGCAGCCCGAGGGGTTTATCTATATAGATGTCGCAGCTTATCATCTCATGC  420

421 TGTCTGTGAGGTTGTTCTGTGTGCTCGTGTAGTATCTTAAATACATAGAGTGTGTTCATA  480

481 TAAAGTGCGACAAAGCTCGATTGGAAACAGCTGTCGAGTGCCCTTGAGTGGGTGGGCAAG  540

541 ATCGTCATCATCATCATCGTCGTCATTATCAACAGAATCAGCATCAGCATCTGGAGGCCC  600

601 CGGTTGCTCTAAGATCCCCAGTGTTCATCAATTATGACTGCCGAGACCCTCAAGCCGTTT  660
  1                                    M  T  A  E  T  L  K  P  F   9

661 ATAACGCCAACGAGTGCCAACGATGATGGTTTTCCGGCCAAAGCGACCAGCACGGCGACC  720
 10  I  T  P  T  S  A  N  D  D  G  F  P  A  K  A  T  S  T  A  T  29

721 GCCCAGCGACGCACCCGCCAGCTGATCCCCCTGGTTTTGGGGTTCATCGGTCTGGGGCTG  780
 30  A  Q  R  R  T  R  Q  L  I  P  L  V  L  G  F  I  G  L  G  L  49

781 GTCGTTGCCATTCTCGCACTAACGATCTGGCAGACAACGCGTGTATCGCATCTGGACAAG  840
 50  V  V  A  I  L  A  L  T  I  W  Q  T  T  R  V  S  H  L  D  K  69

841 GAGCTGAAGAGCCTGAAGCGAGTCGTCGATAATCTCCAGCAGCGTTTGGGCATAAACTAT  900
 70  E  L  K  S  L  K  R  V  V  D  N  L  Q  Q  R  L  G  I  N  Y  89

901 CTGGACGAGTTCGACGAGTTCCAAAAGGAGTACGAGAATGCCCTCATCGACTATCCAAAA  960
 90  L  D  E  F  D  E  F  Q  K  E  Y  E  N  A  L  I  D  Y  P  K  109

961 AAGGTGGATGGCCTCACGGATGAGGAGGACGACGACGATGGCGATGGTCTGGATTCCATT 1020
110  K  V  D  G  L  T  D  E  E  D  D  D  D  G  D  G  L  D  S  I  129
```

Figur 3B

```
1021  GCGGACGACGAGGACGACGACGTTAGCTATAGCTCTGTGGATGATGTTGGCGCAGACTAC  1080
130    A   D   D   E   D   D   D   V   S   Y   S   S   V   D   D   V   G   A   D   Y    149

1081  GAGGACTACACCGATATGTTAAATAAACTCAACAATGCACATACCGGCACCACGCCCACA  1140
150    E   D   Y   T   D   M   L   N   K   L   N   N   A   H   T   G   T   T   P   T    169

1141  TCTGAGACCACTGCTGAGGGCGAGGGCGAGACGGACAGTGCATCCTCAGCCTCAAATGAT  1200
170    S   E   T   T   A   E   G   E   G   E   T   D   S   A   S   S   A   S   N   D    189

1201  GACAATGTGTTCGATGACTTTACCAGCTACAATGCCCACAAAAAGAAGCAGGAGAGAAAA  1260
190    D   N   V   F   D   D   F   T   S   Y   N   A   H   K   K   K   Q   E   R   K    209

1261  TCTCGCTCGATTGCCGATGTACGCAATGAGGAGCAGAATATTCAAGGAAATCACACAGAG  1320
210    S   R   S   I   A   D   V   R   N   E   E   Q   N   I   Q   G   N   H   T   E    229

1321  CTTCAGGAAAAGTCATCCAATGAGGCAACTTCCAAAGAGAGCCCTGCACCACTTCACCAC  1380
230    L   Q   E   K   S   S   N   E   A   T   S   K   E   S   P   A   P   L   H   H    249

1381  CGTCGCAGAATGCATTCCCGCCATCGCCACCTCCTAGTCCGCAAAGCCAGATCCGAGGAC  1440
250    R   R   R   M   H   S   R   H   R   H   L   L   V   R   K   A   R   S   E   D    269

1441  TCGAGGCCAGCAGCCCATTTCCACTTGAGCAGCAGGCGGCGTCACCAAGGAAGTATGGGC  1500
270    S   R   P   A   A   H   F   H   L   S   S   R   R   R   H   Q   G   S   M   G    289

1501  TACCATGGAGATATGTACATAGGAAATGATAACGAGAGAAACTCTTATCAGGGACACTTT  1560
290    Y   H   G   D   M   Y   I   G   N   D   N   E   R   N   S   Y   Q   G   H   F    309

1561  CAAACGCGCGATGGCGTCTTGACGGTGACCAATACAGGCCTATATTACGTATACGCCCAG  1620
310    Q   T   R   D   G   V   L   T   V   T   N   T   G   L   Y   Y   V   Y   A   Q    329

1621  ATATGCTACAACAACTCGCACGACCAGAACGGATTTATCGTCTTTCAAGGAGACACTCCA  1680
330    I   C   Y   N   N   S   H   D   Q   N   G   F   I   V   F   Q   G   D   T   P    349

1681  TTCCTGCAGTGCTTGAACACGGTGCCCACCAACATGCCACATAAGGTGCACACCTGCCAC  1740
350    F   L   Q   C   L   N   T   V   P   T   N   M   P   H   K   V   H   T   C   H    369

1741  ACGAGTGGTCTGATCCACCTGGAACGAAACGAGAGGATCCATCTGAAGGACATTCACAAC  1800
370    T   S   G   L   I   H   L   E   R   N   E   R   I   H   L   K   D   I   H   N    389

1801  GATCGCAATGCAGTTCTGCGGGAGGGAAACAACCGAAGCTACTTTGGCATCTTCAAGGTG  1860
390    D   R   N   A   V   L   R   E   G   N   N   R   S   Y   F   G   I   F   K   V    409

1861  TAAATTGGAGAGATTATCCCCGGTCAGAAGATGGAATACCAGTTTAAGCTTTTGTCCCCG  1920
```

Figure 3C

```
1921  CGACTGCTCGTGAATGCGATTCATCGCCAGCGTGAATCCATTAGTTCGTAGTACCTAGTC  1980

1981  TTAGTCACTCCAAACCTAATCTCAATCGGAATCGTGCATACTGCATTAGTCAGAAGACGG  2040

2041  AGGAAAATCATATTTATTTTGTATATACTCGTTCGACTCTAAAAAGTGAATAAAAATATA  2100

2101  TGTAGCTATTAAAAAAAAAAAAAAAAAAAAAAAAAAAAAAAACTCGAG  2148
```

Figure 4

```
                    1                                                  50
DmTNF    (1)    MTAETLKPFITPTSANDDGFPAKATSTATAQRRTRQLIPLVLGFIGLGLV
DmTNFv1  (1)    MTAETLKPFITPTSANDDGFPAKATSTATAQRRTRQLIPLVLGFIGLGLV
DmTNFv2  (1)    MTAETLKPFITPTSANDDGFPAKATSTATAQRRTRQLIPLVLGFIGLGLV 51                                                 100
DmTNF    (51)   VAILALTIWQTTRVSHLDKELKSLKRVVDNLQQRLGINYLDEFDEFQKEY
DmTNFv1  (51)   VAILALTIWQTTRVSHLDKELKSLKRVVDNLQQRLGINYLDEFDEFQKEY
DmTNFv2  (51)   VAILALTIWQTTRVSHLDKELKSLKRVVDNLQQRLGINYLDEFDEFQKEY 101                                                150
DmTNF    (101)  ENALIDYPKKVDGLTDEEDDDDGDGLDSIADDEDDDVSYSSVDDVGADYE
DmTNFv1  (101)  ENALIDYPKKVDGLTDEEDDDDGDGLDSIADDEDDDVSYSSVDDVGADYE
DmTNFv2  (101)  ENALIDYPKKVDGLTDEEDDDDGDGLDSIADDEDDDVSYSSVDDVGADYE 151                                                200
DmTNF    (151)  DYTDMLNKLNNAHTGTTPTSETTAEGEGETDSASSASNDDNVFDDFTSSD
DmTNFv1  (151)  DYTDMLNKLNNAHTGTTPTSETTAEGEGETDSASSASNDDNVFDDFTSYN
DmTNFv2  (151)  DYTDMLNKLNNAHTGTTPTSETTAEGEGETDSASSASNDDNVFDDFTSYN 201                                                250
DmTNF    (201)  AEKKKQERKSRSIADVRNEEQNIQGNHTELQEKSSNEAASKESPAALHLR
DmTNFv1  (201)  AHKKKQERKSRSIADVRNEEQNIQGNHTELQEKSSNEATSKE--------
DmTNFv2  (201)  AHKKKQERKSRSIADVRNEEQNIQGNHTELQEKSSNEATSKESPAPLHHR 251                                                300
DmTNF    (251)  RRMHSRHRHLVVRK-----ARSEDSRPAAHFHLSSRRRHCESMGYHGDM
DmTNFv1  (243)  -RMHSRHRHLLVRKGESLLSARSEDSRPAAHFHLSSRRRHQCSMGYHGDM
DmTNFv2  (251)  RRMHSRHRHLLVRK-----ARSEDSRPAAHFHLSSRRRHQCSMGYHGDM 301                                                350
DmTNF    (295)  YIENDRERCSYQGHFQTRDGVLTVTNAGLYYVYAQIWGYNSHDQNGFIVF
DmTNFv1  (292)  YIGNDNERNSYQGHFQTRDGVLTVTNIGLYYVYAQICYNNSHDQNGFIVF
DmTNFv2  (295)  YIGNDNERNSYQGHFQTRDGVLTVTNIGLYYVYAQICYNNSHDQNGFIVF 351                                                400
DmTNF    (345)  QGDTPFLQCLNTVPTNMPHKVHTCHTSGLIHLERNERIHLKDIHNDRNAV
DmTNFv1  (342)  QGDTPFLQCLNTVPTNMPHKVHTCHTSGLIHLERNERIHLKDIHNDRNAV
DmTNFv2  (345)  QGDTPFLQCLNTVPTNMPHKVHTCHTSGLIHLERNERIHLKDIHNDRNAV 401        415
DmTNF    (395)  LREGNNRSYFGIFKV
DmTNFv1  (392)  LREGNNRSYFGIFKV
DmTNFv2  (395)  LREGNNRSYFGIFKV
```

Figure 5

```
AC005974 : DS05033 (P1 D347), DS01913 (P1 D350). Finished; 158983 bases.
          Length = 158,983

Minus Strand HSPs:

Score = 77 (27.1 bits), Expect = 5.5, P = 1.0
  Identities = 20/58 (34%), Positives = 31/58 (53%), Frame = -1

Query:     203 NGKLIVNQDGFYYLYANICFRH-HETSGDLA----TEYLQLMVYV-TKTSIKIPSSHT 254
               +G L V   G YY+YA IC+ + H+ +G +       T +LQ +  V T    K+ + HT
Sbjct:  129394 DGVLTVTNTGLYYVYAQICYNNSHDQNGFIVFQGDTPFLQCLNTVPTNMPHKVHTCHT
        129221

Score = 45 (15.8 bits), Expect = 79., Sum P(2) = 1.0
  Identities = 9/17 (52%), Positives = 10/17 (58%), Frame = -1

Query:      28 GPLHAPP--PPAPHQPP 42
               GP    PP  PP+P  PP
Sbjct:  132361 GPSLPPPFPPPSPRTPP 132311
```

Figure 6A

```
                       1                                                  50
DmTNF            (1)   --MTAETLKPFITPTGANDDGFPAKATSTATAQR---------------
DmTNFv1          (1)   --MTAETLKPFITPTGANDDGFPAKATSTATAQR---------------
DmTNFv2          (1)   --MTAETLKPFITPTGANDDGFPAKATSTATAQR---------------
Osteoprotegerin  (1)   -----------MRRASRDYTKYLRGSEEMGGGPGAPHEGPLHAPPPPAP
hCD27L           (1)   -------------------------------------------------
hCD30L           (1)   -------------------------------------------------
hTRAIL           (1)   -----------------------MAMMEVQGGP-----------------
hEctodysplasmin_A (1)  MGYPEVERRELDPAAAPRERCSQGCGCGGAPARA---------------
mEctodysplasmin_A (1)  MGYPEVERREPDPAAAPRERCSQGCGCRGAPARA---------------

51                                                 100
DmTNF            (33)  ----RTRQLIPLVLGFIGLGLVMAILALTIWQTTRVSHLDKELKSLKRVV
DmTNFv1          (33)  ----RTRQLIPLVLGFIGLGLVMAILALTIWQTTRVSHLDKELKSLKRVV
DmTNFv2          (33)  ----RTRQLIPLVLGFIGLGLVMAILALTIWQTTRVSHLDKELKSLKRVV
Osteoprotegerin  (39)  HQPPAASRSMFVALLGLGLGQVVCSVALFFYFRAQMDPN------RISE
hCD27L           (1)   -------------------------------------------------
hCD30L           (1)   -------------------------------------------------
hTRAIL           (11)  ----SLGQTCVLIVIFTVLLQSLCVAVTYVYFTNEL--------KQMQ
hEctodysplasmin_A (35) ----GEGNSCLLFLGFFGLSLALHLLTLCCYLELRS-------ELRRER
mEctodysplasmin_A (35) ----GEGNSCRLFLGFFGLSLALHLLTLCCYLELRS-------ELRRER 101                                                150
DmTNF            (79)  DNLQQRLGINYLDEFDEFQKEYENALIDYPKKVDGLTDEEDDDDGDCLDS
DmTNFv1          (79)  DNLQQRLGINYLDEFDEFQKEYENALIDYPKKVDGLTDEEDDDDGDCLDS
DmTNFv2          (79)  DNLQQRLGINYLDEFDEFQKEYENALIDYPKKVDGLTDEEDDDDGDCLDS
Osteoprotegerin  (82)  DGTHCIYR-----------------ILRLHENADFQDTTLESQDT---
hCD27L           (1)   -------------------------------------------------
hCD30L           (1)   -------------------------------------------------
hTRAIL           (47)  DKYSKS---G---------------HACFLKEDDSYWDPNDEES-----
hEctodysplasmin_A (73) QAESRLGGSGTPGTSGTLSSLGGLDPDSPITSHLCQPSPKQQPLEPGEAA
mEctodysplasmin_A (73) GTESRLGGPGAPGTSGTLSSPGSLDPVGPITRHLGQPSFQQQPLEPGEDP 151                                                200
DmTNF            (129) HADDEDDDVSYGSVDDVGADYEDYTDMLNKLNNAHIGTTPTSETTAEGEG
DmTNFv1          (129) HADDEDDDVSYGSVDDVGADYEDYTDMLNKLNNAHIGTTPTSETTAEGEG
DmTNFv2          (129) HADDEDDDVSYGSVDDVGADYEDYTDMLNKLNNAHIGTTPTSETTAEGEG
Osteoprotegerin  (110) ------------------KLIPDSCRRIKQAFQGAVQKELQHIVGSQHIRAE
hCD27L           (1)   -----------------------MPEEGSGCSVRRRPYGCVLRAALVPL
hCD30L           (1)   --------------------MDPGLQQALNGMAPPGDTAMHVPAGSVAS
hTRAIL           (73)  ---------------MN--SPCWQVKWQLRQLVRKMILRTSEETISTVQ
hEctodysplasmin_A (123) HSDSQDGHQMALLNFFFPDEKPYSEEESRR--VRRNKRSKSNEGADGPV
mEctodysplasmin_A (123) QPPDSQDRHQMALLNFFFPDEKAYSEEESRR--VRRNKRSKSGEGADGPV 201                                                250
DmTNF            (179) ETD-SASSASNDDNVFDDFTSSDALKKKQERKSRSIADVRNEEQNIQGNH
DmTNFv1          (179) ETD-SASSASNDDNVFDDFTSYNAHKKKQERKSRSIADVRNEEQNIQGNH
DmTNFv2          (179) ETD-SASSASNDDNVFDDFTSYNAHKKKQERKSRSIADVRNEEQNIQGNH
Osteoprotegerin  (144) KAMVDG---------------------------SWLDIAK---------
hCD27L           (27)  VAG----------------------------LVICLVVCIQR-------
hCD30L           (30)  HLGTTSRSYFYLTTATLALCLVFTVATIMVLVVQRTDSIPN--------
hTRAIL           (105) EKQQ----------------------------------NISPLVR---
hEctodysplasmin_A (171) KNK-KKGKKAGPPGPNGPPGPPGPPGPQGPPGIPGIPGHPG--TTVMGPP
mEctodysplasmin_A (171) KNK-KKGKKAGPPGPNGPPGPPGPPGPQGPPGIPGIPGIPG--TTVMGPP 251                                                300
DmTNF            (228) TELQEKSSNEAASKESPAALHLRRRMHSRHRHLVVRK------ARSEDSR
DmTNFv1          (228) TELQEKSSNEATSKE---------RMHSRHRHLLVRKGESLLSARSEDSR
DmTNFv2          (228) TELQEKSSNEATSKESPAPLHHRRRMHSRHRHLLVRK------ARSEDSR
Osteoprotegerin  (157) ------------------------------RSKLEAQP-----------
hCD27L           (41)  ----------------------------------FAGAQQQLPLES---
hCD30L           (71)  ----------------------------------SDDNVPLKGGN-----CSED
hTRAIL           (116) ----ERGPQ-------------------RVAAHITGTR-----------
hEctodysplasmin_A (218) GPPGPPGPQGPPGLQGP---------SGAADKAGTR--------ENQP
mEctodysplasmin_A (218) GPPGPPGPQGPPGLQGP---------SGAADKTGTR--------ENQP
```

Figure 6B

```
                         301                                                350
         DmTNF    (272)  PAAHFHLSSRRRHQESMGYHGDMYIENDRER-CSYQGHEQTRDGVLTVTN
       DmTNFv1    (269)  PAAHFHLSSRRRHQGSMGYHGDMYIGNDNER-NSYQGHEQTRDGVLTVTN
       DmTNFv2    (272)  PAAHFHLSSRRRHQGSMGYHGDMYIGNDNER-NSYQGHEQTRDGVLTVTN
  Osteoprotegerin (165)  --FAHLTINATDIPSG-SHKVSLSSWYHDRG-WAKISNMTFSNGKLIVNQ
        hCD27L    (53)   --LGWDVAELQLNHTGPQQDPRIYWQGGPALCRSFLHGPELDKGQLRIHR
        hCD30L    (86)   LLCILKRAPFKKSWAYLQVAKHLNKTKLSWNKDGILHGVRYQDGNLVIQF
        hTRAIL    (131)  -GRSN-TLSSPNSKNEKALGRKINSWESSRSGHSFLSNLHLRNGELVIHE
hEctodysplasmin_A (249)  AVVHLQGQGSAIQVKNDLSGGVLNDWSRITM-NEKVFKLHPRSGELEVLV
mEctodysplasmin_A (249)  AVVHLQGQGSAIQVKNDLSGGVLNDWSRITM-NEKVFKLHPRSGELEVLV 351                                                400
         DmTNF    (321)  AGLYYVY--------AQIWGYNSHDQNGEIVEQG-DTPFLQCLNIVPTNM
       DmTNFv1    (318)  TGLYYVY--------AQICYNNSHDQNGEIVEQG-DTPFLQCLNIVPTNM
       DmTNFv2    (321)  TGLYYVY--------AQICYNNSHDQNGEIVEQG-DTPFLQCLNIVPTNM
  Osteoprotegerin (211)  DGFYYLYANICFRHHETSGDLATEYLQLMVYVTKTSIKIPSSHTLMKGGS
        hCD27L    (101)  DGIYMVHIQVTLAICSSITASRHHPTILAVGICS---PASRSISLLRLSF
        hCD30L    (136)  PGLYFIICQLQFLVQCPNNSVDLKLELLINKHIKKGALVTVCESGMQIKH
        hTRAIL    (179)  KGFYYIYSQTYFRFQEEIKENTKNDKQMVQYIYK-YTSYPDPILLMKSAR
hEctodysplasmin_A (298)  DGTYFIYSQ------VEMYYINFTDFASYEVVVD-EKPFLQCTRSIETGK
mEctodysplasmin_A (298)  DGTYFIYSQ------VEMYYINFTDFASYEVVVD-EKPFLQCTRSIETGK 401                                                450
         DmTNF    (362)  PHK--------VHTCHTSGLIHLERNERIHLKDILNDRNAVLREGNNRSY
       DmTNFv1    (359)  PHK--------VHTCHTSGLIHLERNERIHLKDILNDRNAVLREGNNRSY
       DmTNFv2    (362)  PHK--------VHTCHTSGLIHLERNERIHLKDILNDRNAVLREGNNRSY
  Osteoprotegerin (261)  TKYWSGNSEFHFYSINVGGFKLRSGEEISIEVSNPSLLDPDQ---DAIY
        hCD27L    (148)  HQG---------CTIVSQRLTPLARGDTLCINLIGTLLPSRNT---DETF
        hCD30L    (186)  VYQN----------LSQFIDYIQVNTTISVNVDTFQYIDTSTFPLENVL
        hTRAIL    (228)  NSCWSKDAEYGLVSIYQGGIFELKENDRIFVSVTNEHLIDMDH---EASF
hEctodysplasmin_A (341)  TN--------YNTCYTAGVCLLKARQKIAVKMVHADISINMS--KHTTF
mEctodysplasmin_A (341)  TN--------YNTCYTAGVCLLKARQKIAVKMVHADISINMS--KHTTF 451       462
         DmTNF    (404)  FGIFKV------
       DmTNFv1    (401)  FGIFKV------
       DmTNFv2    (404)  FGIFKV------
  Osteoprotegerin (308)  FGAFKVRDID--
        hCD27L    (186)  FGVQWVRP----
        hCD30L    (226)  SIFFYSNSD---
        hTRAIL    (275)  FGAFLVG-----
hEctodysplasmin_A (380)  FGAIRLGEAPAS
mEctodysplasmin_A (380)  FGAIRLGEAPAS
```

Figure 11

DmTNF

| Protein | Genbank ID | Identities | Similarities |
|---|---|---|---|
| human osteoprotegerin protein | gi|12643360 | 21.4% | 35.7% |
| human hCD27 ligand protein | gi| P32970 | 12.5% | 37.5% |
| human CD30 ligand protein | gi| P32971 | 20% | 26.7% |
| human TRAIL protein | gi| P50591 | 24.6% | 34.4% |
| human ectodysplasmin_A protein | gi|Q92838 | 21.2% | 27.9% |
| mouse ectodysplasmin_A protein | gi|NP_034229 | 20.4% | 28.5% |

DmTNFv1

| Protein | Genbank ID | Identities | Similarities |
|---|---|---|---|
| human osteoprotegerin protein | gi|12643360 | 23.8% | 30.5% |
| human hCD27 ligand protein | gi| P32970 | 12.5% | 37.5% |
| human CD30 ligand protein | gi| P32971 | 20% | 26.7% |
| human TRAIL protein | gi| P50591 | 23.3% | 32.7% |
| human ectodysplasmin_A protein | gi|Q92838 | 21.8% | 28.6% |
| mouse ectodysplasmin_A protein | gi|NP_034229 | 21% | 28.6% |

DmTNFv2

| Protein | Genbank ID | Identities | Similarities |
|---|---|---|---|
| human osteoprotegerin protein | gi|12643360 | 21.4% | 35.7% |
| human hCD27 ligand protein | gi| P32970 | 12.5% | 37.5% |
| human CD30 ligand protein | gi| P32971 | 20% | 26.7% |
| human TRAIL protein | gi| P50591 | 24.1% | 33.9% |
| human ectodysplasmin_A protein | gi|Q92838 | 22.4% | 29.1% |
| mouse ectodysplasmin_A protein | gi|NP_034229 | 21.6% | 29.2% |

DROSOPHILA TUMOR NECROSIS FACTOR CLASS MOLECULE POLYNUCLEOTIDES AND VARIANTS THEREOF

This application claims priority from Provisional U.S. application Ser. No. 60/190,816, filed on Mar. 21, 2000.

FIELD OF THE INVENTION

The present invention provides novel polynucleotides encoding *Drosophila* DmTNF polypeptides, fragments and homologs thereof. The present invention also is directed to novel polynucleotides encoding two Drosophila DmTNF variants, DmTNFv1 and DmTNFv2 polypeptides, fragments and homologs thereof. Also provided are vectors, host cells, antibodies, and recombinant and synthetic methods for producing said polypeptides. The invention further relates to screening methods for identifying agonists and antagonists of the polynucleotides and polypeptides of the present invention, in addition to methods of genetically modifying Drosophila or cultured cells to express or mis-express DmTNF, DmTNFv1, or DmTNFv2. The invention also relates to the use of such modified insects or cells to characterize DmTNF activity, identify TNF-like genes and/or genes implicated in modulating TNF, characterize TNF signaling pathways, and/or to identify modulators of DmTNF activity.

BACKGROUND OF THE INVENTION

There have been various cytokines identified that inhibit manifestations of biological functions such as immunoresponse, inflammatory reactions, and hemopoietic functions in the body. The structures and activities of these molecules have gradually been clarified. With such clarification, it has also been made clear that these cytokine molecules are effective not only on the immune system, but also on various other biological functions.

In fact, a large number of human diseases involve TNF molecules including endotoxic shock, inflammation, hemorrhagic necrosis of tumors, cytotoxicity, (reviewed Tracey, K. and Cerami, A. (1994), Annu Rev Med 45:491–503, Vassalli, P., (1992) Annu Rev Immunol 10:411–452), and obesity-linked insulin resistance (Hotamisligil, G. et al., Science 259:87–91), to name a few. The TNF superfamily currently includes 17 members in vertebrates (review Locksley, R. et al. (2001) Cell 104: 487–501). This family exhibits the highest homology between their C-terminal, receptor binding domains. The superfamily members are type II membrane proteins that act in an autocrine, paracrine, or endocrine manner either as integral membrane proteins or as proteolytically processed soluble factors (Banner et al. (1993), Cell 73:431–445).

Most members within this ligand family are expressed in the immune system and play important roles in immune system development and modulation (Smith et al., (1994) Cell 76:959–962). For example, TNFalpha is expressed in macrophages and is a critical mediator of inflammatory responses and immune defenses (Tracey and Cerami, 1994). Pharmaceuticals to inhibit TNF control pathogenic inflammatory responses such as rheumatoid arthritis and inflammatory bowel disease (Maini, R. and Taylor, P. (2000) Annu. Rev., Med, 51, 207–229, Papadakis, K. and Targan, S. (2000) Annu. Rev. Med. 51, 289–298.)

Despite the functional redundancy of this family, specificity may be accomplished by coordinating the spatial and temporal expression of TNF-related ligands and their receptors, and by restricting the expression of signal transduction molecules to specific cell types. Many TNF receptors have been identified and share characteristic multiple cysteine repeats within their extracellular domain and do not possess cytoplasmic catalytic domains. TNF receptors interact with a family of molecules called TRAFs (TNF receptor associated proteins) that act as adaptors for downstream signaling events. Hence, binding of a TNF cytokine to its cognate receptor, which is interacting with TRAF, leads to the activation of several signal transduction pathways, including the activation of the cascade of caspase/ICE-like proteases, which are responsible for apoptosis. Also activated is the Rel protein family of transcription factors, which inhibit apoptosis, and mitogen activated protein kinases including the Jun N-terminal protein kinases (JNK) and the extracellularly-regulated kinases (ERK) (Locksley et al, 2001).

Among the cytokines, TNF was identified as an antitumor cytokine and has been expected to be useful as an antitumor agent. However, later it was reported that TNF has an activity of stimulating production of other cytokines such as IL-1, etc., proliferative activity of fibroblasts, endotoxin shock-inducing activity, an activity of promoting the adhesion of leukocytes to endothelium by increasing intercellular adhesion molecules (ICAM-1, ICAM-2) or endothelial leukocyte adhesion molecule-1 (ELAM-1), an activity of bone absorption, and an activity of inducing arthritis (e.g. cartilage decomposing activity). (Beutler, B., et al., Nature, 316, 552–554 (1985); Peetre, C., et al., J. Clin. Invest., 78, 1694–1700 (1986); Kurt-Jones, E. A., et al., J. Immunol., 139, 2317–2324 (1987); Bevilacqua, M. P., et al., Science, 243, 1160–1165 (1989); Akatu, K. & Suda, T., Medical Practice,.8 (9), 1393–1396 (1991).

Moreover, it is reported that in bacterial or parasitic infectious diseases, TNF is contained in a higher concentration in blood and cerebrospinal fluid (Mitsuyama, M., IGAKU-NO-AYUMI, 159 (8), 467–470 (1991); and Masayasu, N., IGAKU-NO-AYUMI, 159 (8), 471–474 (1991)). It is also reported that in rheumatoid arthritis, the joint fluid and blood serum have TNFα activity. (Saxne, T., et al., Arthritis Rheum., 31, 1041 (1988); Chu, C. Q., et al., Arthritis Rheum., 34, 1125–1132 (1991); Macnaul, K. L., et al., J. Immunol., 145, 4154–4166 (1990); Brennan, F. M., et al., Eur, J. Immunol., 22(7):1907–12, (1992); and Brennan, F. M., et al., Bri. J. Rheum., 31, 293–298 (1992)).

It is further reported that in patients suffering from adult respiratory distress syndrome (ARDS), the phlegm of the patients contain increased levels of TNF (Millar, A. B., et al., Nature, 324, 73 (1986)), and that TNF also participates in the severity of virus hepatitis. (Muto, Y., et al., Lancet, 2(8602) :72–4, (1988)).

It is also reported that the blood concentration of TNFα rises in cases of myocardial ischemia (e.g. acute myocardial infarction) (Latini, R., et al., J. Cardiovasc. Pharmacol., 23, 1–6 (1994)), and it is suggested that TNFα is involved in such diseases. (Lefer, A. M., et al, Science, 249, 61–64 (1990)). It has also been reported that TNFα inhibits myocardial contraction. (Finkel, M. S., et al., Science, 257, 387–389 (1992); and Pagani, D. F., et al., J. Clin. Invest., 90, 389–398 (1992)).

No known invertebrate TNF molecules have been reported to date, although many TNF intracellular signaling molecules such as TRAFs and Rel proteins have been identified in Drosophila melagaster (Khush, R. and Lemaitre, B. (2000) Trends Genet. 16:442–449). Identification of a novel TNF in Drosophila provides, for the first time, a useful tool for genetic and molecular study of TNF biology and the subsequent validation of such molecules as pharmaceutical targets. The present invention provides the encoding polynucleotide and polypeptide sequence of a novel Drosophila TNF protein. The present invention also provides methods linking the inventive DmTNF to the Re1 protein signal transduction in Drosophila. The use of Drosophila as a model organism with genetic and other technologies would be useful in the elucidation of biological pathways, particularly those related to TNF (Margolis, J. and Duyk, G. Nat Biotechnol. (1998)16:311, Matthews D. and Kopczynski, J (2001) Drug Disc., Today 6: 141–149).

Therefore, the development of therapeutics that modulate (i.e., act as antagonists or agonists of TNF) is important to treat diseases related to TNF.

BRIEF SUMMARY OF THE INVENTION

The present invention provides isolated nucleic acid molecules, that comprise, or alternatively consist of, a polynucleotide encoding the DmTNF protein having the amino acid sequence shown in FIGS. 1A–C (SEQ ID NO:2) or the amino acid sequence encoded by the cDNA clone, DmTNF.

The present invention provides isolated nucleic acid molecules, that comprise, or alternatively consist of, a polynucleotide encoding the DmTNFv1 protein having the amino acid sequence shown in FIGS. 2A–B (SEQ ID NO:4) or the amino acid sequence encoded by the cDNA clone, DmTNFv1.

The present invention provides isolated nucleic acid molecules, that comprise, or alternatively consist of, a polynucleotide encoding the DmTNFv2 protein having the amino acid sequence shown in FIGS. 3A–C (SEQ ID NO:2) or the amino acid sequence encoded by the cDNA clone, DmTNFv2.

The present inventors sequenced the cDNA encoding the novel DmTNF and determined the primary sequence of the deduced protein. The novel DmTNF has homology to known sequences encoding TNF molecules.

The DmTNF of the present invention can be produced by: (1) inserting the cDNA of the disclosed DmTNF into an appropriate expression vector; (2) transfecting the expression vector into an appropriate transfection host(s); (3) growing the transfected host(s) in appropriate culture media; and (4) purifying the receptor protein from the culture media.

The present invention therefore provides a purified and isolated nucleic acid molecule, preferably a DNA molecule, having a sequence which codes for a DmTNF, or an oligonucleotide fragment of the nucleic acid molecule which is unique to the DmTNF of the invention. In a preferred embodiment of the invention, the purified and isolated nucleic acid molecule has the sequence as shown in SEQ ID NO:1, 3, or 5.

The invention also contemplates a double stranded nucleic acid molecule comprising a nucleic acid molecule of the invention or an oligonucleotide fragment thereof hydrogen bonded to a complementary nucleotide base sequence.

The terms "isolated and purified nucleic acid" and "substantially pure nucleic acid", e.g., substantially pure DNA, refer to a nucleic acid molecule which is one or both of the following: (1) not immediately contiguous with either one or both of the sequences, e.g., coding sequences, with which it is immediately contiguous (i.e., one at the 5' end and one at the 3' end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure or isolated and purified DNA also includes a recombinant DNA which is part of a hybrid gene encoding additional DmTNF/TNF sequence.

The present invention provides in one embodiment: (a) an isolated and purified nucleic acid molecule comprising a sequence encoding all or a portion of a protein having the amino acid sequence as shown in SEQ ID NO:2; (b) nucleic acid sequences complementary to (a); (c) nucleic acid sequences which exhibit at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions. In a particular embodiment, the fragment is a sequence encoding a DmTNF having the amino acid sequence as shown in SEQ ID NO:2 and sequences having at least 80%, more preferably at least 90%, more preferably at least 95%, and most preferably at least 98% sequence identity thereto.

The degree of homology (percent identity) between a native and a mutant sequence may be determined, for example, by comparing the two sequences using computer programs commonly employed for this purpose. One suitable program is the GAP computer program described by Devereux et al., (1984) *Nucl. Acids Res.* 12:387. The GAP program utilizes the alignment method of Needleman and Wunsch (1970) *J. Mol. Biol.* 48:433, as revised by Smith and Waterman (1981) *Adv. Appl. Math.* 2:482. Briefly, the GAP program defines percent identity as the number of aligned symbols (i.e., nucleotides or amino acids) which are identical, divided by the total number of symbols in the shorter of the two sequences.

As used herein the term "stringent conditions" encompasses conditions known in the art under which a nucleotide sequence will hybridize to an isolated and purified nucleic acid molecule comprising (a) a sequence encoding a protein having the amino acid sequence as shown herein, or to (b) a nucleic acid sequence complementary to (a). Screening polynucleotides under stringent conditions may be carried out according to the method described in Nature, 313:402–404 (1985). Polynucleotide sequences capable of hybridizing under stringent conditions with the polynucleotides of the present invention may be, for example, allelic variants of the disclosed DNA sequences, or may be derived from other sources. General techniques of nucleic acid hybridization are disclosed by Sambrook et al., "Molecular Cloning: A Laboratory Manual", 2nd Ed., Cold Spring Harbor Laboratory, Cold Spring Harbor, New York (1984); and by Haymes et al., "Nucleic Acid Hybridization: A Practical Approach", IRL Press, Washington, D.C. (1985), which references are incorporated herein by reference.

The present invention also provides: (a) a purified and isolated nucleic acid molecule comprising a sequence as shown in SEQ ID NO:1; (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention additionally covers nucleic acid molecules of the present invention having one or more structural mutations including replacement, deletion or insertion mutations. For example, a signal peptide may be deleted, or conservative amino acid substitutions may be made to generate a protein that is still biologically competent or active.

The invention further contemplates a recombinant molecule comprising a nucleic acid molecule of the present invention or an oligonucleotide fragment thereof and an expression control sequence operatively linked to the nucleic acid molecule or oligonucleotide fragment. A transformant host cell including a recombinant molecule of the invention is also provided.

In another aspect, the invention features a cell or purified preparation of cells which include a novel gene encoding a DmTNF of the present invention, or which otherwise misexpresses a gene encoding a DmTNF of the present invention. The cell preparation can consist of human or non-human cells, e.g., insect cells, rodent cells (e.g., mouse or rat cells), rabbit cells, or pig cells. In preferred embodiments, the cell or cells include a DmTNF transgene, e.g., a heterologous form of a DmTNF gene, e.g., a gene derived from humans (in the case of a non-human cell). The DmTNF transgene can be misexpressed, e.g., overexpressed or underexpressed. In other preferred embodiments, the cell or cells include a gene which misexpresses an endogenous DmTNF gene, e.g., a gene the expression of which is disrupted, e.g., a knockout. Such cells can serve as a model for studying disorders which are related to mutated or misexpressed DmTNF alleles for use in drug screening.

The present invention also relates to recombinant vectors, which include the isolated nucleic acid molecules of the present invention, and to host cells containing the recombinant vectors, as well as to methods of making such vectors and host cells, in addition to their use in the production of DmTNF polypeptides or peptides using recombinant techniques. Synthetic methods for producing the polypeptides and polynucleotides of the present invention are provided. Also provided are diagnostic methods for detecting diseases, disorders, and/or conditions related to the DmTNF polypeptides and polynucleotides, and therapeutic methods for treating such diseases, disorders, and/or conditions. The invention further relates to screening methods for identifying binding partners of the polypeptides.

Still further, the invention provides plasmids which comprise the nucleic acid molecules of the invention.

The present invention also includes a novel DmTNF of the present invention, or an active part thereof. A biologically competent or active form of the protein or part thereof is also referred to herein as an "active DmTNF or part thereof".

The invention further contemplates antibodies having specificity against an epitope of the DmTNF of the present invention or part of the protein. These antibodies may be polyclonal or monoclonal. The antibodies may be labeled with a detectable substance and they may be used, for example, to detect the novel DmTNF of the invention in tissue and cells. Additionally, the antibodies of the present invention, or portions thereof, may be used to make targeted antibodies that destroy DmTNF expressing cells (e.g., antibody-toxin fusion proteins, or radiolabelled antibodies).

The invention also permits the construction of nucleotide probes which encode part or all of the novel DmTNF protein of the invention or a part of the protein. Thus, the invention also relates to a probe comprising a nucleotide sequence coding for a protein, which displays the properties of the novel DmTNF of the invention or a peptide unique to the protein. The probe may be labeled, for example, with a detectable (e.g., radioactive) substance and it may be used to select from a mixture of nucleotide sequences a nucleotide sequence coding for a protein which displays the properties of the novel DmTNF of the invention.

The present invention also provides a transgenic insect or non-human animal (e.g.; a rodent, e.g., a mouse or a rat, a rabbit or a pig) or embryo all of whose germ cells and somatic cells contain a recombinant molecule of the invention, preferably a recombinant molecule comprising a nucleic acid molecule of the present invention encoding the DmTNF of the invention or part thereof. The recombinant molecule may comprise a nucleic acid sequence encoding the DmTNF of the present invention with a structural mutation, or may comprise a nucleic acid sequence encoding the DmTNF of the invention or part thereof and one or more regulatory elements which differ from the regulatory elements that drive expression of the native protein. In another preferred embodiment, the insect or animal has a DmTNF gene which is misexpressed or not expressed, e.g., a knockout. Such transgenic animals can serve as a model for studying disorders which are related to mutated or misexpressed DmTNF of the present invention.

The invention still further provides a method for identifying a substance which is capable of binding the novel DmTNF of the invention, comprising reacting the novel DmTNF of the invention or part of the protein under conditions which permit the formation of a complex between the substance and the novel DmTNF protein or part of the protein, and assaying for substance-DmTNF complexes, for free substance, for non-complexed DmTNF, or for activation of the substance (e.g., receptor) that binds to the DmTNF of the present invention.

An embodiment of the invention provides a method for identifying receptors which are capable of binding the novel DmTNF protein of the invention, isoforms thereof, or part of the protein, said method comprising reacting the novel DmTNF protein of the invention, isoforms thereof, or part of the protein, with at least one receptor which potentially is capable of binding to the protein, isoform, or part of the protein, under conditions which permit the formation of receptor-ligand protein complexes, and assaying for receptor-ligand protein complexes, for free DmTNF, for non-complexed receptor protein, or for activation of the receptor that binds to the DmTNF of the present invention. In a preferred embodiment of the method, receptors are identified which are capable of binding the novel DmTNF protein of the invention, isoforms thereof, or part of the protein.

The invention also relates to a method for assaying a medium for the presence of an agonist or antagonist of the interaction of the novel DmTNF protein and a substance which is capable of binding the DmTNF, said method comprising providing a known concentration of the DmTNF, reacting the DmTNF with a substance (e.g., receptor) which is capable of binding the DmTNF and a suspected agonist or antagonist under conditions which permit the formation of substance-DmTNF complexes, and assaying for substance-DmTNF complexes, for free substance, for non-complexed DmTNF, or for activation of the substance (e.g., receptor).

Also included within the scope of the present invention is a composition which includes the DmTNF of the present invention, a fragment thereof (or a nucleic acid encoding said DmTNF or fragment thereof) and one or more additional components, e.g., a carrier, diluent or solvent. The additional component can be one which renders the composition useful for in vitro, in vivo, pharmaceutical or veterinary use.

In another aspect, the present invention relates to a method of treating a mammal, e.g., a human, at risk for a disorder, e.g., a disorder characterized by aberrant or unwanted level or biological activity of the DmTNF (or DmTNF homolog) of the present invention, or characterized by an aberrant or unwanted level of a ligand that specifically binds the DmTNF (or a DmTNF homolog) of the present invention. For example, the DmTNF of the present invention may be useful to leach out or block a ligand which is found to bind to the DmTNF of the present invention.

A further object of the present invention is the identification of new molecules (e.g., human homologues) homologous to the DmTNF provided herein, and methods of screening for molecules that modulate the biological activities of the novel DmTNF disclosed herein. Additional objects of the invention are the methods of using the cDNA, the DmTNF protein, the monoclonal antibody specific for the novel DmTNF, and a ligand for the novel DmTNF as described above.

BRIEF DESCRIPTION OF THE FIGURES/DRAWINGS

FIGS. 1A–C shows the predicted polynucleotide sequence (SEQ ID NO:1) and deduced amino acid sequence (SEQ ID NO:2) of the novel Drosophila tumor necrosis factor class gene, DmTNF, of the present invention. The standard one-letter abbreviation for amino acids is used to illustrate the deduced amino acid sequence. The polynucleotide sequence contains a sequence of 2166 nucleotides (SEQ ID NO:1), encoding a polypeptide of 409 amino acids (SEQ ID NO:2). An analysis of the DmTNF polypeptide determined that it comprised the following features: a predicted signal sequence located from about amino acid 1 to about amino acid 52 of SEQ ID NO:2 represented by single underlining; and a predicted TNF domain located from about amino acid 316 to about amino acid 331 (SEQ ID NO:18) of SEQ ID NO:2 represented by shading.

FIGS. 2A–B shows the predicted polynucleotide sequence (SEQ ID NO: 3) and deduced amino acid sequence (SEQ ID NO:4) of the novel Drosophila tumor necrosis factor class gene variant, DmTNFv1, of the present invention. The standard one-letter abbreviation for amino acids is used to illustrate the deduced amino acid sequence. The polynucleotide sequence contains a sequence of 1221 nucleotides (SEQ ID NO:3), encoding a polypeptide of 406 amino acids (SEQ ID NO:4). An analysis of the DmTNFv1 polypeptide determined that it comprised the following features: a predicted signal sequence located from about amino acid 1 to about amino acid 52 of SEQ ID NO:4 represented by single underlining; and a predicted TNF domain located from about amino acid 313 to about amino acid 329 (SEQ ID NO:19) of SEQ ID NO:2 represented by shading.

FIGS. 3A–C shows the predicted polynucleotide sequence (SEQ ID NO: 5) and deduced amino acid sequence (SEQ ID NO:6) of the novel Drosophila tumor necrosis factor class gene variant, DmTNFv2, of the present invention. The standard one-letter abbreviation for amino acids is used to illustrate the deduced amino acid sequence. The polynucleotide sequence contains a sequence of 2148 nucleotides (SEQ ID NO:5), encoding a polypeptide of 409 amino acids (SEQ ID NO:6). An analysis of the DmTNF polypeptide determined that it comprised the following features: a predicted signal sequence located from about amino acid 1 to about amino acid 52 of SEQ ID NO:2 represented by single underlining; and a predicted TNF domain located from about amino acid 316 to about amino acid 332 (SEQ ID NO:20) of SEQ ID NO:2 represented by shading. DmTNFv2 is believed to represent the physiologically relevant form of the DmTNF gene.

FIG. 4 shows the regions of identity and similarity between the polypeptide sequences of DmTNF (SEQ ID NO:2), DmTNFv1 (SEQ ID NO:4), and DmTNFv2 (SEQ ID NO:6) of the present invention. The alignment was performed using the CLUSTALW algorithm as available within the Vector NTI AlignX program (CLUSTALW parameters: gap opening penalty: 10; gap extension penalty: 0.5; gap separation penalty range: 8; percent identity for alignment delay: 40%; and transition weighting: 0). The darkly shaded amino acids represent regions of matching identity. The lightly shaded amino acids represent regions of matching similarity. Lines between residues indicate gapped regions for the aligned polypeptides.

FIG. 5 shows the regions of local identity and similarity between the human Osteoprotegerin protein (Query; SEQ ID NO:7; Genbank Accession No. gi|12643360) and the translated amino acid sequence of Drosophila contig AC005974 (Sbjct; Genbank Accession No. gi|AC005974). This result represented the first indication that a TNF-domain containing protein resided within the Drosophila genome. The local alignment was performed using the BLAST2 algorithm using default parameters (Altschul, S. F., Madden, T. L., Schaffer, A. A., Zhang, J., Zhang, Z., Miller, W., and Lipman, D. L., Nucleic Acid Res. 25, 3389–3402 (1997)). Amino acids denoted between the 'Query' and 'Sbjct' lines represent amino acids of matching identity. Similar amino acids are represented by a plus ("+") sign between the 'Query' and 'Sbjct' lines. Non-matching regions are represented by dots ("•") between the 'Query' and 'Sbjct' lines.

FIGS. 6A–B show the regions of identity and similarity between DmTNF (SEQ ID NO:2), DmTNFv1 (SEQ ID NO:4), and DmTNFv2 (SEQ ID NO:6) of the present invention and other members of the TNF superfamily, specifically, the human osteoprotegerin protein (Osteoprotegerin; Genbank Accession No. gi|12643360; SEQ ID NO:7), the human hCD27 ligand protein (hCD27L; Genbank Accession No. gi|P32970; SEQ ID NO:15), the human CD30 ligand protein (hCD30L; Genbank Accession No. gi|P32971; SEQ ID NO:16); the human TRAIL protein (hTRAIL; Genbank Accession No. gi|P50591; SEQ ID NO:17); the human ectodysplasmin_A protein (hEctodysplasmin_A; Genbank Accession No. gi|Q92838; SEQ ID NO:8), and the mouse ectodysplasmin_A protein (mEctodysplasmin_A; Genbank Accession No. gi|NP_034229; SEQ ID NO:9). The strong conservation within the TNF domain is noted. The alignment was performed using the CLUSTALW algorithm as available within the Vector NTI AlignX program (CLUSTALW parameters: gap opening penalty: 10; gap extension penalty: 0.5; gap separation penalty range: 8; percent identity for alignment delay: 40%; and transition weighting: 0). The darkly shaded amino acids represent regions of matching identity. The lightly shaded amino acids represent regions of matching similarity. Lines between residues indicate gapped regions for the aligned polypeptides. FIG. 7 shows a Kyte-Doolittle hydropathy plot of the novel Drosophila tumor necrosis factor class gene. DmTNF is a type II transmembrane protein (e.g., protentially secreted protein), with a short intracellular domain at the NH2 terminal of DmTNF and a long extracellular domain at the COOH terminal of DmTNF.

Figure 8:
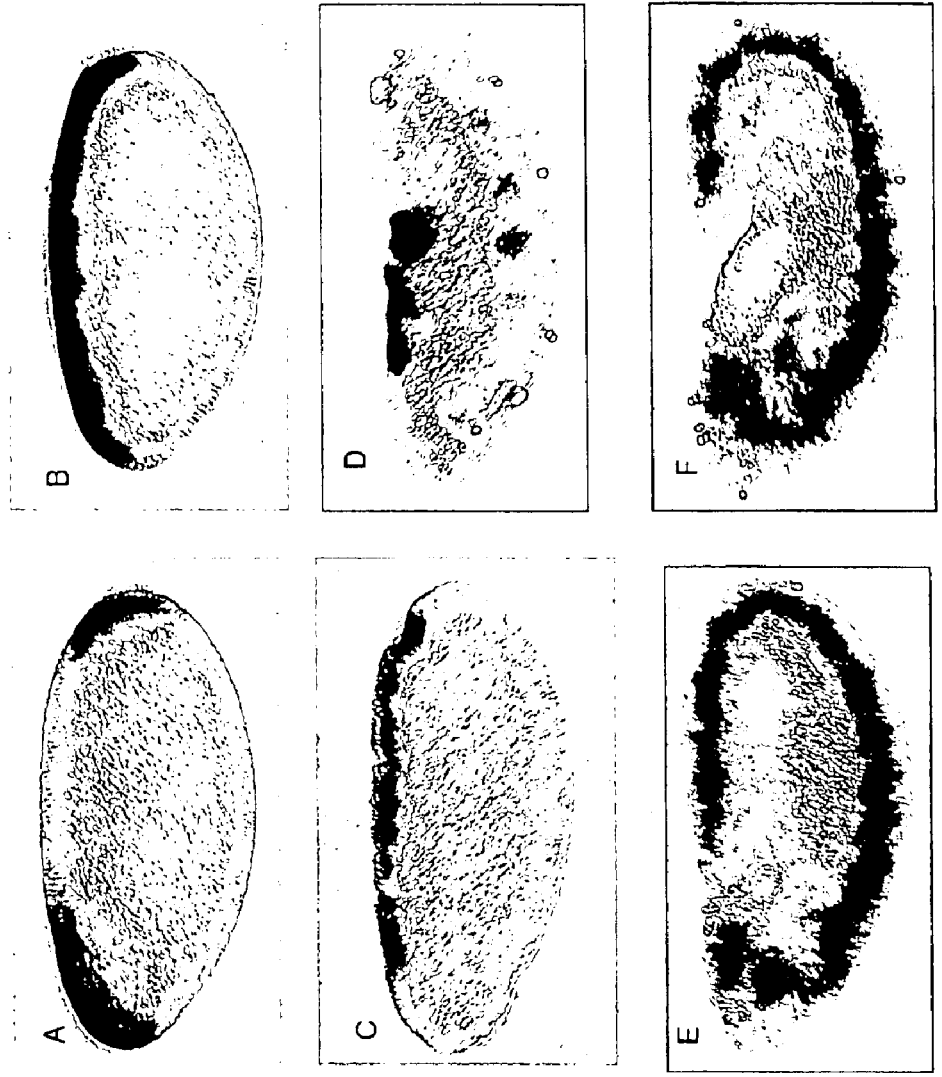

FIG. 8 shows an In situ hybridization of Drosophila embryos at various developmental stages using DmTNF cDNA as described herein. The figures represent a side view of embryos with anterior end at left, posterior end at right, dorsal side up and ventral side down. Embryos were staged according to Roberts et al. (1998) as follows: (A) Stage 4/5, beginning of cell formation; (B) Stage 5: cell formation; (C) Stage 6, early gastrulation, ventral furrow formation; (D) The end of stage 7; (E) Stage 10, stomodeal invagination, weak mesoderm expression; and (F) Stage 12, shortening of germ band. As shown, DmTNF gene expression was upregulated in the dorsal region of the developing embryo (stage 4/5) at a time coincident with the activation of Rel activity in the ventral region only. In addition, DmTNFv2 expression was also observed in mesoderm specific tissues at stage 10 of embryonic development.

Figure 9:
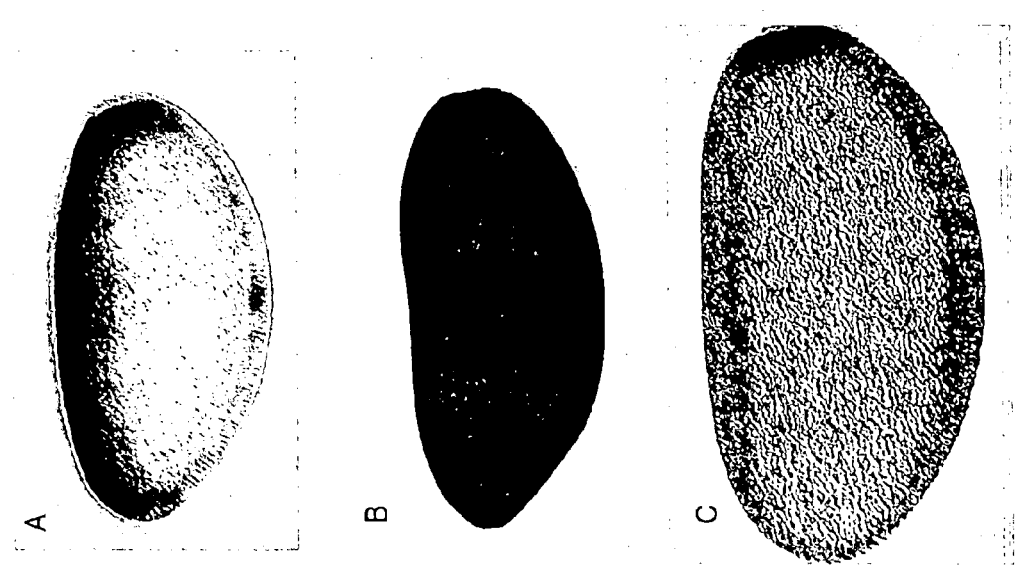

FIG. 9 shows an In situ hybridization of Drosophila embryos in mutant backgrounds using DmTNF cDNA as described herein. The figures represent a side view of embryos with anterior end at left, posterior end at right, dorsal side up and ventral side down. The embryos are represented as follows: (A) A wild-type embryo; (B) dl1/dl1 maternal mutant background; and (C) T13 mutants, wherein dl1 mutants represent Dorsal (re1 protein) recessive mutant embryos in which Re1 signaling has been "turned off" and thus lack Dorsal function, and wherein T13 mutants represent dominant activated Toll mutants in which Re1 signaling is constitutively active. All embryos were staged according to Roberts et al. (1998) at stage 5. As shown, DmTNF was expressed only in areas where Re1 proteins are not activated. The results, in conjunction with the results provided in FIG. 8 and elsewhere herein, suggest DmTNF is negatively regulated by the Re1 activation pathway in embryogenesis.

Figure 10:
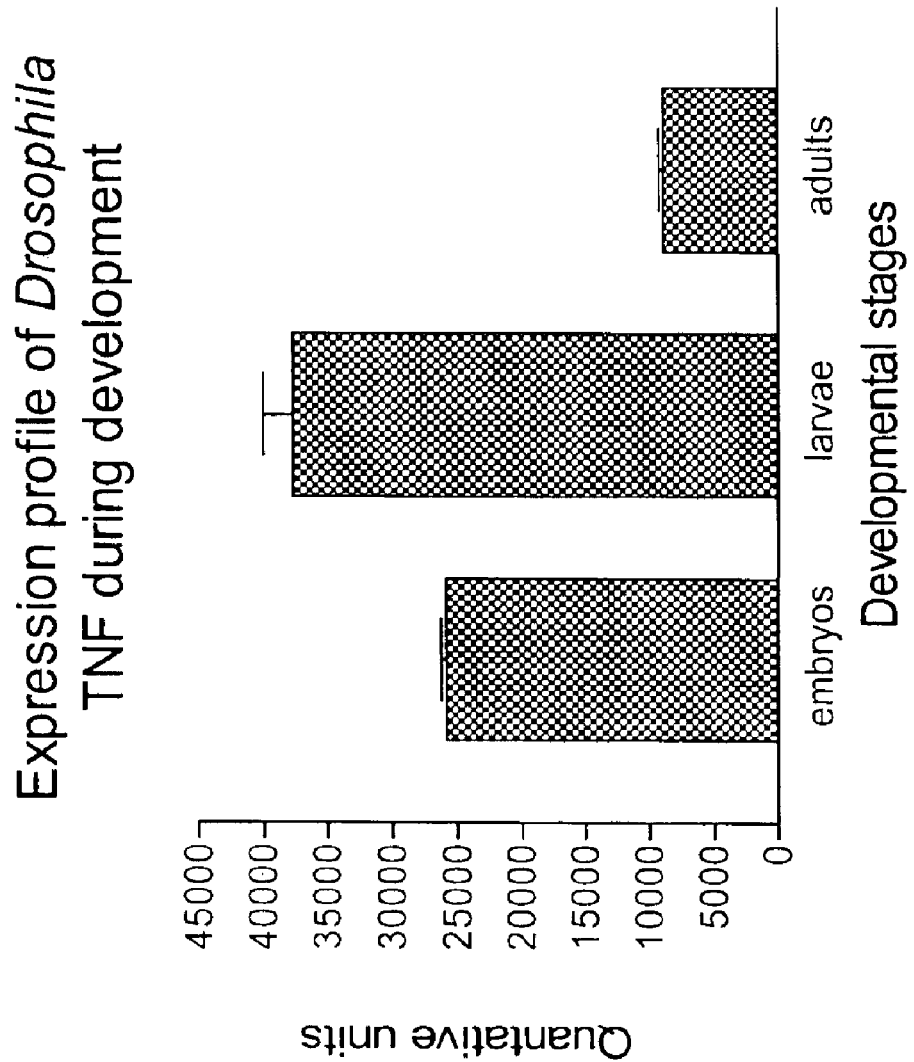

FIG. 10 shows an expression profile of the novel Drosophila tumor necrosis factor class gene, DmTNF. The figure illustrates the relative expression level of DmTNF amongst mRNA isolated from developing Drosophila embryos and adults. As shown, transcripts corresponding to DmTNF expressed predominately high in Drosophila larvae. The DmTNF polypeptide was also expressed significantly in Drosophila embryos, and to a lesser extent, in adults. Expression data was obtained by measuring the steady state DmTNF mRNA levels by quantitative PCR using the PCR primer pair provided as SEQ ID NO:11 and 12 as described herein.

FIG. 11 shows a table illustrating the percent identity and percent similarity between DMTNF, DmTNFv1, and DmTNFv2 polypeptides of the present invention with the human osteoprotegerin protein (Osteoprotegerin; Genbank Accession No. gil12643360; SEQ ID NO:7), the human hCD27 ligand protein (hCD27L; Genbank Accession No. gilP32970; SEQ ID NO:15), the human CD30 ligand protein (hCD30L; Genbank Accession No. gilP32971; SEQ ID NO:16); the human TRAIL protein (hTRAIL; Genbank Accession No. gilP50591; SEQ ID NO:17); the human ectodysplasmin_A protein (hEctodysplasmin_A; Genbank Accession No. gilQ92838; SEQ ID NO:8), and the mouse ectodysplasmin_A protein (mEctodysplasmin_A; Genbank Accession No. gilNP_034229; SEQ ID NO:9). The percent identity and percent similarity values were determined using the GAP algorithm (GCG suite of programs; and Henikoff, S. and Henikoff, J. G., Proc. Natl. Acad. Sci. USA 89: 10915–10919(1992)) according to the following parameters: gap weight=8, and length weight=2.

Figure 12:
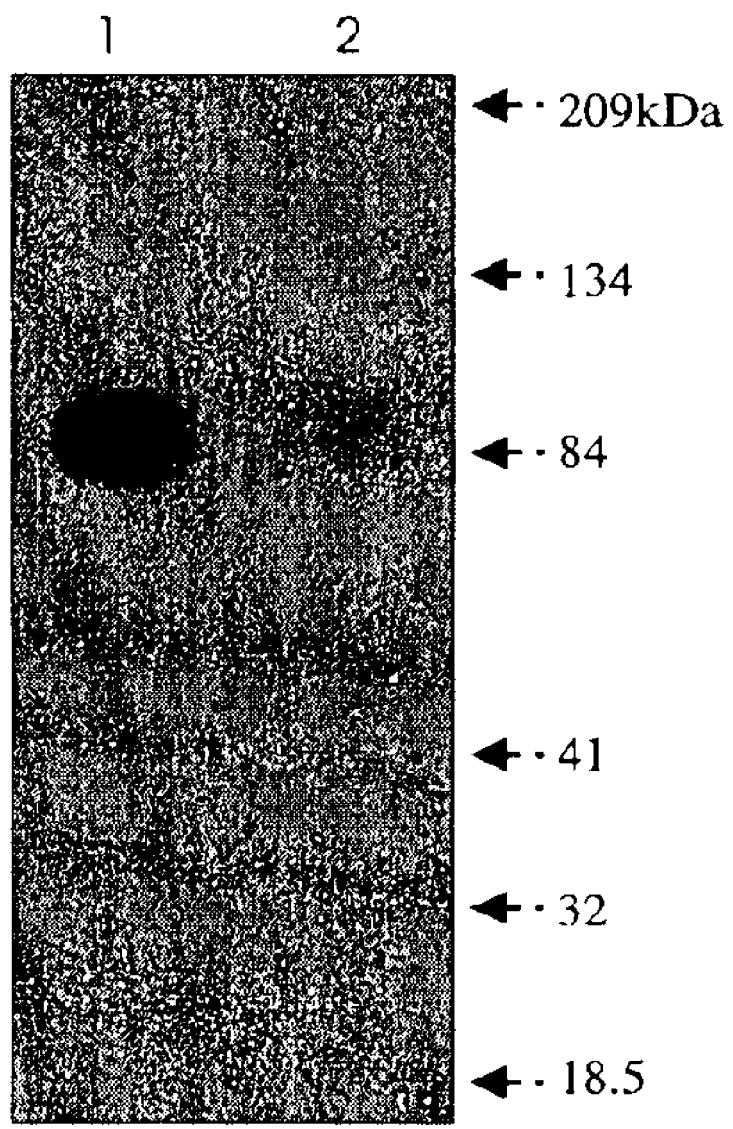

FIG. 12 shows an autoradiogram of an $^{35}$S-Cys/Met labeled dmTNFv2/mouse CD8 fusion protein separated by SDS-PAGE. cDNA fragments encoding the predicted extracellular region of dmTNFv2 were obtained by PCR and cloned into a vector containing the coding sequence of the extracellular region of mouse CD8/Lyt2a, as described herein. Isolation of a soluble form of DmTNF will facilitate additional functional characterization.

DETAILED DESCRIPTION OF THE INVENTION

The present invention may be understood more readily by reference to the following detailed description of the preferred embodiments of the invention and the Examples included herein. All references to "DmTNF" shall be construed to apply to DmTNF, DmTNFv1, and/or DmTNFv2 unless otherwise specified herein.

The invention provides a novel Drosophila sequence that potentially encodes a tumor necrosis factor class gene, DmTNF. The invention also provides novel Drosophila sequences corresponding to two DmTNF variants, DmTNFv1 and DmTNFv2. Transcripts for DmTNFv2 were found predominately in Drosophila larvae, significantly in embryos, and to a lesser extent, in adult flies, suggesting that the invention modulates developmental function.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO: 1. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

The present invention further relates to variants of the hereinabove described nucleic acid sequence which encode for fragments, analogs and derivatives of the polypeptide having the deduced amino acid sequence of SEQ ID NO:2, SEQ ID NO:4, or SEQ ID NO:6. The variants of the nucleic acid sequence may be naturally occurring variants of the nucleic acid sequence or non-naturally occurring variants of the nucleic acid sequence.

Thus, the present invention includes polynucleotides encoding the polypeptide as shown in SEQ ID NO:2, SEQ ID NO:4, or SEQ ID NO:6 as well as variants of such polynucleotides which variants encode for a fragment, derivative or analog of the polypeptide of SEQ ID NO:2, SEQ ID NO:4, or SEQ ID NO:6. Such nucleotide variants include deletion variants, substitution variants and addition or insertion (splice) variants.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 3A–C (SEQ ID NO:5), a nucleic acid molecule of the present invention encoding the DmTNFv2 polypeptide may be obtained using standard cloning and screening procedures, such as those for cloning cDNAs using mRNA as starting material. As the nucleotide sequence in FIGS. 1A–C (SEQ ED NO:1) and FIGS. 2A–B (SEQ ID NO:3) were determined using bioinformatic methods, isolation of a clone for these sequences may require a combination of classical cloning and mutagenesis procedures.

The determined nucleotide sequence of DmTNF in FIGS. 1A–C (SEQ ID NO:1) contains an open reading frame encoding a protein of about 409 amino acid residues, with a deduced molecular weight of about 46.3 kDa. The amino acid sequence of the predicted DmTNF polypeptide is shown in FIGS. 1A–C (SEQ ID NO:2).

The determined nucleotide sequence of DmTNFv1 in FIGS. 2A–B (SEQ ID NO:3) contains an open reading frame encoding a protein of about 406 amino acid residues, with a deduced molecular weight of about 45.9 kDa. The amino acid sequence of the predicted DmTNFv1 polypeptide is shown in FIGS. 2A–B (SEQ ID NO:4).

The determined nucleotide sequence of the DmTNFv2 cDNA in FIGS. 3A–C (SEQ ID NO:5) contains an open reading frame encoding a protein of about 409 amino acid residues, with a deduced molecular weight of about 46.3 kDa. The amino acid sequence of the predicted DmTNFv2 polypeptide is shown in FIGS. 3A–C (SEQ ID NO:6).

A "polynucleotide" of the present invention also includes those polynucleotides capable of hybridizing, under stringent hybridization conditions, to sequences contained in SEQ ID NO:1, 3, 5, or the complement thereof,. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6X SSPE (20X SSPE=3M NaCl; 0.2M NaH2PO4; 0.02M EDTA, pH 7.4), 0.5% SDS, 30% formamide, 100 µg/ml salmon sperm blocking DNA; followed by washes at 50 degree C. with 1XSSPE, 0.1% SDS. In addition, to achieve even lower stringency, washes performed following stringent hybridization can be done at higher salt concentrations (e.g. 5X SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1", "SEQ ID NO:3", and "SEQ ID NO:5" refer to polynucleotide sequences, while "SEQ ID NO:2", "SEQ ID NO:4", and "SEQ ID NO:6" refer to polypeptide sequences, all sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to metazoan invertebrate organisms (e.g. insects, coelomates and pseudocoelomates), and most preferably to flies.

The term "gene" means the segment of DNA involved in producing a polypeptide chain; it includes regions preceding and following the coding region (leader and trailer) as well as intervening sequences (introns) between individual coding segments (exons).

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321–9, (1995); and Ann. N Y Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes for the identification and isolation of full-length cDNAs and/or genomic DNA which correspond to novel homologs and/or orthologs, particularly human, of the polynucleotides of the present invention, as probes to hybridize and discover novel, related DNA sequences, as probes for positional cloning of this or a related sequence, as probes to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

In further preferred embodiments, the polynucleotides of the present invention are useful in genetic screening methods to characterize biochemical pathways that involve DmTNF, in addition to its use in methods for screening molecules that modulate DmTNF or the DmTNF pathway.

Fragments of the full length gene of the present invention may be used as hybridization probes for a cDNA library to isolate the full length gene and to isolate other genes which have a high sequence similarity to a gene of the present invention or similar biological activity. Probes of this type preferably have at least between 20 and 30 bases, and may contain, for example, 50 or more bases. The probes may also be used to identify a cDNA clone corresponding to a full length transcript and a genomic clone or clones that contain the complete gene of the present invention including regulatory and promoter regions, exons, and introns.

The present invention further relates to polynucleotides that hybridize to the polynucleotide sequences disclosed herein, if there is at least 80%, preferably at least 90%, and more preferably at least 95% identity between the sequences. The present invention particularly relates to polynucleotides which hybridize under stringent conditions to the polynucleotides described herein.

Alternatively the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, SEQ ID NO:3, or SEQ ID NO:5 for example for recovery of the polynucleotide or as a diagnostic probe or as a PCR primer.

Thus the present invention is directed to polynucleotides having at least 80% identity, preferably at least 90% and more preferably at least 95% identity to a polynucleotide of the present invention, including polynucleotides encoding the polypeptide of SEQ ID NO:2, SEQ ID NO:4, or SEQ ID NO:6, as well as fragments thereof, which fragments have at least 20 or 30 bases, and preferably at least 50 bases, and to polypeptides encoded by such polynucleotides.

Polynucleotides and Polypeptides of the Invention
Features of the Polypeptide Encoded by Gene No:1

The polypeptide of this gene provided as SEQ ID NO:2 (FIGS. 1A–C), encoded by the polynucleotide sequence according to SEQ ID NO:1 (FIGS. 1A–C), and/or encoded by the polynucleotide contained within the clone, DmTNF, has significant homology at the nucleotide and amino acid level to the human osteoprotegerin protein (Osteoprotegerin; Genbank Accession No. gi|12643360; SEQ ID NO:7), the human hCD27 ligand protein (hCD27L; Genbank Accession No. gi|P32970; SEQ ID NO:15), the human CD30 ligand protein (hCD30L; Genbank Accession No. gi|P32971; SEQ ID NO:16); the human TRAIL protein (hTRAIL; Genbank Accession No. gi|P50591; SEQ ID NO:17); the human ectodysplasmin_A protein (hEctodysplasmin_A; Genbank Accession No. gi|Q92838; SEQ ID NO:8), and the mouse ectodysplasmin_A protein (mEctodysplasmin_A; Genbank Accession No. gi|NP_034229; SEQ ID NO:9). An alignment of the DmTNF polypeptide with these proteins is provided in FIGS. 6A–B.

The DmTNF polypeptide was determined to share 21.4% identity and 35.7 milarity with the human osteoprotegerin protein (Osteoprotegerin; Genbank Accession No. gi|12643360; SEQ ID NO:7), to share 12.5% identity and 37.5% similarity with the human hCD27 ligand protein (hCD27L; Genbank Accession No. gi|P32970; SEQ ID NO:15), to share 20% identity and 26.7% similarity with the human CD30 ligand protein (hCD30L; Genbank Accession No. gi|P32971; SEQ ID NO:16); to share 24.6% identity and 34.4% similarity with the human TRAIL protein (hTRAIL; Genbank Accession No. gi|P50591; SEQ ID NO:17); to share 21.2% identity and 27.9% similarity with the human ectodysplasmin_A protein (hEctodysplasmin_A; Genbank Accession No. gi|Q92838; SEQ ID NO:8), and to share 20.4% identity and 28.5% similarity with the mouse ectodysplasmin_A protein (mEctodysplasmin_A; Genbank Accession No. gi|NP_034229; SEQ ID NO:9) as shown in FIG. 11.

Expression profiling designed to measure the steady state mRNA levels encoding the DmTNF polypeptide showed predominately high expression levels in Drosophila embryos, significantly in larvae, and to a lesser extent, in adult (as shown in FIG. 3).

Moreover, in situ hybridization of Drosophila embryos at various developmental stages indicated that DmTNF gene expression was upregulated in the dorsal region of the developing embryo (stage 4/5) at a time coincident with the activation of Re1 activity in the ventral region only. Specifically, DmTNF was expressed only in areas where Re1 proteins are not activated. The results, in conjunction with the results provided elsewhere herein, suggest DmTNF is negatively regulated by the Re1 activation pathway in embryogenesis.

Based upon the observed homology, the polypeptide of the present invention may share at least some biological activity with tumor necrosis family members, specifically with CD27L, CD30L and TRAIL, and preferably with the tumor necrosis factor family members referenced elsewhere herein.

The DmTNF polypeptide was determined to comprise a signal sequence from about amino acid 1 to about amino acid 52 of SEQ ID NO:2 (FIGS. 1A–C) according to the SPScan computer algorithm (Genetics Computer Group suite of programs). Based upon the predicted signal peptide cleavage site, the mature DmTNF polypeptide is expected to be from about amino acid 53 to about amino acid 409 of SEQ ID NO:2 (FIGS. 1A–C). As this determination was based upon the prediction from a computer algorithm, the exact physiological cleavage site may vary, as discussed more particularly herein. In this context, the term "about" should be construed to mean 1, 2, 3, 4, 5, 6, 7, 8, 9, 10, 11, 12, 13, 14, 15, 16, 17, 18, 19, or 20 more amino acids in either the N- or C-terminal direction of the above referenced polypeptide. Polynucleotides encoding these polypeptides are also provided.

In addition to the mature polypeptide above, the polynucleotides encoding the mature polypeptide are also encompassed by the present invention. Specifically, from about nucleotide position 808 to about nucleotide position 1878 of SEQ ID NO:1 (FIGS. 1A–C).

Similarly, several members of the TNF family, such as, for example, CD27L, CD30L and TRAIL, in addition to the ectodysplasin-A protein, are type II transmembrane proteins. Hydrophobicity plot analysis using Kyte-Doolittle Hydropathy algorithm suggests that DmTNF is also a type II transmembrane protein (e.g., potentially secreted protein), with a short intracellular domain at the NH2 terminal of DmTNF and a long extracellular domain at the COON terminal of DmTNF as shown in FIG. 7.

In terms of general utility of the novel DmTNF of the present invention, gene expression of DmTNF suggests it is important in immunomodulation and metabolic biology in Drosophila, and potentially humans. Biochemical pathways are highly conserved from Drosophila to man; therefore, studies in Drosophila are very relevant to human biology. Through tools common to Drosophila research the biological significance and biochemical pathways of DmTNF can be elucidated. Loss of function mutations in DmTNF will be identified and transgenic flies can be generated to overexpress DmTNF and mutant forms in specific tissues. These types of experiments may be used to identify the DmTNF receptor, its signaling pathway and the biological functions of DmTNF.

Similar to other receptor systems being investigated (e.g., CD40/CD40L, 4-IBB/4-1BBL, Fas/FasL) it is contemplated by the present invention that the interaction between the novel DmTNF (or human homologues found using the novel DmTNF of the present invention) and its receptor may serve as a novel target for immunosuppressive, anti-inflammatory and/or immunostimulatory drug development.

The present invention relates to the nucleic acid sequence or a fragment thereof (referred to herein as a "polynucleotide") of the novel DmTNF as shown above (SEQ ID NO:1), as well as to the amino acid sequence of the DmTNF (SEQ ID NO:2), and biologically active portions thereof.

The present invention further relates to a tumor necrosis factor molecule polypeptide, DmTNF, which has the deduced amino acid sequence as shown in SEQ ID NO:2, as well as fragments, analogs and derivatives of such polypeptide.

DmTNF polynucleotide and polypeptides, including variants or fragments thereof, can be used for the generation of mutant phenotypes in animal models or in living cells. Preferably, such phenotypes are genetically modified to either express or misexpress the DmTNF gene, for example using transposon mutagenesis, RNA interference, chemical mutagenesis, or other genetic techniques. As discussed elsewhere herein, the expression of the DmTNF protein may be driven by a heterologous promoter that is tissue-specific, developmentally specific, or inducible, enabling the effects of the expression or misexpression can be observed in specific tissues, at certain developmental stages, or at specified times, respectively. Such mutant phenotypes are useful for studying the regulation of DmTNF, and the use of DmTNF as a drug target in an effort to identify potential therapeutic compounds. Due to the ability to carry out large scale, systematic genetic screens, the use of Drosophila has great utility for analyzing the expression and mis-expression of DmTNF, TNF proteins, and/or TNF homology. Additionally, the DmTNF pathway protein may be linked to one or more selectable markers that allows detection of expression. For example, the expression of the DmTNF results in an identifiable phenotype.

DmTNF polynucleotide and polypeptides, including variants or fragments thereof, are useful for screening molecules that modulate DmTNF, or the DmTNF pathway.

In addition, DmTNF polynucleotide and polypeptides, including variants or fragments thereof, are useful in the elucidation of biological pathways, particularly TNF pathways (Margolis, J. and Duyk, G. Nat Biotechnol. (1998)16: 311, Matthews D. and Kopczynski , J (2001) Drug Disc. Today 6: 141–149). DmTNF polynucleotide and polypeptides, including variants or fragments thereof, are useful for identifying other TNF family members.

The homology to the human osteoprotegerin ligand protein, combined with the observed expression in Drosophila embryos, suggests the DmTNF polynucleotides and polypeptides of the present invention have uses which include treating, ameliorating, and/or preventing diseases and disorders related to aberrant osteoprotegerin, ligand function. Moreover, the DmTNF polynucleotides and polypeptides of the present invention may be useful for augmenting the ability of dendritic cells to stimulate naive t-cell proliferation, in regulating interaction between t cells and dendritic cells, modulating the regulation of the t cell-dependent immune response, in addition to, potentially enhancing bone-resorption in humoral hypercalcemia of malignancy, in animals, preferably humans. DmTNF may also be useful in modulating immune responses, and/or ameliorating or preventing morphological aberrations in insects, preferably in flies, such as Drosophila.

In addition, the negative regulation of DmTNF by Rel strongly suggests DmTNF polynucleotides and polypeptides of the present invention have uses which include modulating the innate immune response in invertebrates, particularly flies, and most preferably in Drosophila. Moreover, the specific expression in embryos also suggests DmTNF polynucleotides and polypeptides of the present invention have uses which include modulating development and/or patterning during embryogenesis in invertebrates, particularly flies, and most preferably in Drosophila.

As noted above, the DmTNF polypeptide was also determined to share significant homology with both the human and mouse ectodysplasmin_A protein. Mutations within ectodysplasin-A in mice has been shown in result in a Tabby phenotype (i.e., no sweat glands). Ectodysplasin-A has been shown to function in epithelial morphogenesis and promotes cell-matrix adhesion. In addition, mutations in the human ectodysplasmin-A has been directly implicated in X-linked anhidrotic (hypohidrotic) ectodermal dysplasia (Kere, J., et al., Nat. Genet. 13 (4), 409–416 (1996)). This disorder results in sparse hair (atrichosis or hypotrichosis), abnormal or missing teeth and the inability to sweat due to the absence of sweat glands in humans.

Therefore, DmTNF polynucleotides and polypeptides, including fragments and/or antagonists thereof, may have uses which include modulating epithelial morphogenesis, cell-matrix adhesion, in flies, preferably Drosophila, and potentially in other organisms as well, preferably mammals, such as humans, mice, and rats. Moreover, DmTNF polypeptides and polypeptides, including fragments and/or antagonists thereof, may have uses which include treating, ameliorating, and/or preventing X-linked anhidrotic (hypohidrotic) ectodermal dysplasia, including X-linked anhidrotic (hypohidrotic) ectodermal dysplasia-like disorders, such as sparse hair, abnormal or missing teeth, and sweat gland aberrations, in animals, preferably insects, and potentially in humans.

In preferred embodiments, the following N-terminal DmTNF deletion polypeptides are encompassed by the present invention: M1-V409, T2-V409, A3-V409, E4-V409, T5-V409, L6-V409, K7-V409, P8-V409, F9-V409, I10-V409, T11-V409, P12-V409, T13-V409, S14-V409, A15-V409, N16-V409, D17-V409, D18-V409, G19-V409, F20-V409, P21-V409, A22-V409, K23-V409, A24-V409, T25-V409, S26-V409, T27-V409, A28-V409, T29-V409, A30-V409, Q31-V409, R32-V409, R33-V409, T34-V409, R35-V409, Q36-V409, L37-V409, I38-V409, P39-V409, L40-V409, V41-V409, LA2-V409, G43-V409, F44-V409, I45-V409, G46-V409, L47-V409, G48-V409, L49-V409, V50-V409, V51-V409, A52-V409, I53-V409, L54-V409, A55-V409, L56-V409, T57-V409, I58-V409, W59-V409, Q60-V409, T61-N409, T62-V409, R63-V409, V64-V409, S65-V409, H66-V409, L67-V409, D68-V409, K69-V409, E70-V409, L71-V409, K72-V409, S73-V409, L74-V409, K75-V409, R76-V409, V77-V409, V78-V409, D79-V409, N80-V409, L81-V409, Q82-V409, Q83-V409, R84-V409, L85-V409, G86-V409, I87-V409, N88-V409, Y89-V409, L90-V409, D91-V409, E92-V409, F93-V409, D94-V409, E95-

V409, F96-V409, Q97-V409, K98-V409, E99-V409, Y100-V409, E101-V409, N102-V409, A103-V409, L104-V409, I105-V409, D106-V409, Y107-V409, P108-V409, K109-V409, K110-V409, V104-V409, D112-V409, G113-V409, L114-V409, T115-V409, D116-V409, E117-V409, E118-V409, D119-V409, D120-V409, D121-V409, D122-V409, G123-V409, D124-V409, G125-V409, L126-V409, D127-V409, S128-V409, I129-V409, A130-V409, D131-V409, D132-V409, E133-V409, D134-V409, D135-V409, D136-V409, V137-V409, S138-V409, Y139-V409, S140-V409, S141-V409, V142-V409, D143-V409, D144-V409, V145-V409, G146-V409, A147-V409, D148-V409, Y149-V409, E150-V409, D151-V409, Y152-V409, T153-V409, D154-V409, M155-V409, L156-V409, N157-V409, K158-V409, L159-V409, N160-V409, N161-V409, A162-V409, H163-V409, T164-V409, G165-V409, T166-V409, T167-V409, P168-V409, T169-V409, S170-V409, E171-V409; T172-V409, T173-V409, A174-V409, E175-V409, G176-V409, E177-V409, G178-V409, E179-V409, T180-V409, D181-V409, S182-V409, A183-V409, S184-V409, S185-V409, A186-V409, S187-V409, N188-V409, D189-V409, D190-V409, N191-V409, V192-V409, F193-V409, D194-V409, D195-V409, F196-V409, T197-V409, S198-V409, S199-V409, D200-V409, A201-V409, L202-V409, K203-V409, K204-V409, K205-V409, Q206-V409, E207-V409, R208-V409, K209-V409, S210-V409, R211-V409, S212-V409, I213-V409, A214-V409, D215-V409, V216-V409, R217-V409, N218-V409, E219-V409, E220-V409, Q221-V409, N222-V409, I223-V409; Q224-V409, G225-V409, N226-V409, H227-V409, T228-V409, E229-V409, L230-V409, Q231-V409, E232-V409, K233-V409, S234-V409, S235-V409, N236-V409, E237-V409, A238-V409, A239-V409, S240-V409, K241-V409, E242-V409, S243-V409, P244-V409, A245-V409, A246-V409, L247-V409, H248-V409, L249-V409, R250-V409, R251-V409, R252-V409, M253-V409, H254-V409, S255-V409, R256-V409, H257-V409, R258-V409, H259-V409, L260-V409, V261-V409, V262-V409, R263-V409, K264-V409, A265-V409, R266-V409, S267-V409, E268-V409, D269-V409, S270-V409, R271-V409, P272-V409, A273-V409, A274-V409, H275-V409, F276-V409, H277-V409, L278-V409, S279-V409, S280-V409, R281-V409, R282-V409, R283-V409, H284-V409, Q285-V409, E286-V409, S287-V409, M288-V409, G289-V409, Y290-V409, H291-V409, G292-V409, D293-V409, M294-V409, Y295-V409, I296-V409, E297-V409, N298-V409, D299-V409, R300-V409, E301-V409, S302-V409, C303-V409, S304-V409, Y305-V409, Q306-V409, G307-V409, H308-V409, F309-V409, Q310-V409, T311-V409, R312-V409, D313-V409, G314-V409, V315-V409, L316-V409, T317-V409, V318-V409, T319-V409, N320-V409, A321-V409, G322-V409, L323-V409, Y324-V409, Y325-V409, V326-V409, Y327-V409, A328-V409, Q329-V409, I330-V409, W331-V409, G332-V409, Y333-V409, N334-V409, S335-V409, H336-V409, D337-V409, Q338-V409, N339-V409, G340-V409, F341-V409, I342-V409, V343-V409, F344-V409, Q345-V409, G346-V409, D347-V409, T348-V409, P349-V409, F350-V409, L351-V409, Q352-V409, C353-V409, L354-V409, N355-V409, T356-V409, V357-V409, P358-V409, T359-V409, N360-V409, M361-V409, P362-V409, H363-V409, K364-V409, V365-V409, H366-V409, T367-V409, G368-V409, H369-V409, T370-V409, S371-V409, G372-V409, L373-V409, I374-V409, H375-V409, L376-V409, E377-V409, R378-V409, N379-V409, E380-V409, R381-V409, I382-V409, H383-V409, L384-V409, K385-V409, D386-V409, I387-V409, H388-V409, N389-V409, D390-V409, R391-V409, N392-V409, A393-V409, V394-V409, L395-V409, R396-V409, E397-V409, G398-V409, N399-V409, N400-V409, R401-V409, S402-V409, and/or Y403-V409 of SEQ ID NO:2. Polynucleotide sequences encoding these polypeptides are also provided. The present invention also encompasses the use of these N-terminal DmTNF deletion polypeptides as immunogenic and/or antigenic epitopes as described elsewhere herein.

In preferred embodiments, the following C-terminal DmTNF deletion polypeptides are encompassed by the present invention: M1-V409, M1-K408, M1-F407, M1-I406, M1-G405, M1-F404, M1-Y403, M1-S402, M1-I401, M1-N400, M1-N399, M1-G398, M1-E397, M1-I396, M1-I395, M1-V394, M1-A393, M1-N392, M1-I391, M1-D390, M1-N389, M1-H388, M1-I387, M1-D386, M1-K385, M1-L384, M1-H383, M1-I382, M1-I381, M1-E380, M1-N379, M1-I378, M1-E377, M1-L376, M1-H375, M1-I374, M1-I373, M1-G372, M1-S371, M1-T370, M1-H369, M1-C368, M1-T367, M1-H366, M1-V365, M1-K364, M1-H363, M1-P362, M1-M361, M1-N360, M1-T359, M1-P358, M1-V357, M1-T356, M1-N355, M1-I354, M1-C353, M1-Q352, M1-I351, M1-F350, M1-P349, M1-T348, M1-D347, M1-G346, M1-Q345, M1-F344, M1-V343, M1-I342, M1-F341, M1-G340, M1-N339, M1-Q338, M1-D337, M1-H336, M1-S335, M1-N334, M1-Y333, M1-G332, M1-W331, M1-I330, M1-Q329, M1-A328, M1-Y327, M1-V326, M1-Y325, M1-Y324, M1-I323, M1-G322, I1-A321, M1-N320, M1-T319, M1-V318, M1-T317, M1-L316, M1-V315, M1-G314, M1-D313, M1-8312, M1-T311, M1-Q310, M1-F309, M1-H308, M1-G307, M1-Q306, M1-Y305, M1-S304, M1-C303, M1-I302, M1-E301, M1-I300, M1-D299, M1-N298, M1-E297, M1-I296, M1-Y295, M1-M294, M1-D293, M1-G292, M1-H291, M1-Y290, M1-G289, M1-M288, M1-S287, M1-E286, M1-Q285, M1-H284, M1-I283, M1-I1282, M1-I281, M1-S280, M1-S279, M1-I278, M1-H277, M1-F276, M1-I3275, M1-A274, M1-A273, M1-P272, M1-R271, M1-S270, M1-D269, M1-E268, M1-S267, M1-I266, M1-A265, M1-K264, M1-R263, M1-V262, M1-V261, M1-I260, M1-H259, M1-I258, M1-H257, M1-R256, M1-S255, M1-H254, M1-M253, M1-I252, M1-I251, M1-I250, M1-I249, M1-H248, M1-I247, M1-A246, M1-A245, M1-P244, M1-S243, M1-E242, M1-K241, M1-S240, M1-A239, M1-A238, M1-E237, M1-N236, M1-S235, M1-S234, M1-K233, M1-E232, M1-Q231, M1-I230, M1-E229, M1-T228, M1-H227, M1-N226, M1-G225, M1-Q224, M1-I223, M1-N222, M1-Q221, M1-E220, M1-E219, M1-N218, M1-I217, M1-V216, M1-D215, M1-A214, M1-I213, M1-S212, M1-I211, M1-S210, M1-K209, M1-R208, M1-E-207, M1-Q206, M1-K205, M1-K204, M1-K203, M1-L202, M1-A201, M1-D200, M1-S199, M1-S198, M1-T197, M1-F196, M1-D195, M1-D194, M1-F193, M1-V192, M1-N191, M1-D190, M1-D189, M1-N188, M1-S187, M1-A186, M1-S185, M1-S184, M1-A183, M1-S182, M1-D181, M1-T180, M1-E179, M1-G178, M1-E177, M1-G176, M1-E175, M1-A174, M1-T173, M1-T172, M1-E171, M1-S170, M1-T169, M1-P168, M1-T167, M1-T166, M1-G165, M1-T164, M1-H163, M1-A162, M1-N161, M1-N160, M1-L159, M1-K158, M1-N157, M1-L156, M1-M155, M1-D154, M1-T153, M1-Y152, M1-D151, M1-E150, M1-Y149, M1-D148, M1-A147, M1-G146, M1-V145, M1-D144, M1-D143, M1-V142, M1-S141, M1-S140, M1-Y139, M1-S138, M1-V137, M1-D136, M1-D135, M1-D134, M1-E133, M1-D132, M1-D131, M1-A130, M1-I129, M1-S128, M1-D127, M1-L126, M1-G125, M1-D124, M1-G123, M1-D122, M1-D121, M1-D120, M1-D119, M1-E118, M1-E117, M1-D116, M1-T115, M1-L114, M1-G113, M1-D112, M1-V111, M1-K110, M1-K109, M1-P108, M1-Y107, M1-D106, M1-I105, M1-L104, M1-A103, M1-N102, M1-E101, M1-Y100, M1-E99, M1-K98, M1-Q97, M1-F96, M1-E95, M1-D94, M1-F93, M1-E92, M1-D91, M1-L90, M1-Y89, M1-N88, M1-I87, M1-G86, M1-L85, M1-R84, M1-Q83, M1-Q82, M1-L81, M1-N80, M1-D79, M1-V78, M1-V77, M1-R76, M1-K75, M1-L74, M1-S73, M1-K72, M1-L71, M1-E70, M1-K69, M1-D68, M1-L67, M1-H66, M1-S65, M1-V64, M1-R63, M1-T62, M1-T61, M1-Q60, M1-W59, M1-I58, M1-T57, M1-L56, M1-A55, M1-L54, M1-I53, M1-A52, M1-V51, M1-V50, M1-L49, M1-G48, M1-L47, M1-G46, M1-I45, M1-F44, M1-G43, M1-L42, M1-V41, M1-L40, M1-P39, M1-I38, M1-L37, M1-Q36, M1-R35, M1-T34, M1-R33, M1-R32, M1-Q31, M1-A30, M1-T29, M1-A28, M1-T27, M1-S26, M1-T25, M1-A24, M1-K23, M1-A22, M1-P21, M1-F20, M1-G19, M1-D18, M1-D17, M1-N16, M1-A15, M1-S14, M1-T13, M1-P12, M1-T11, M1-I10, M1-F9, M1-P8, and/or M1-K7 of SEQ ID NO:2. Polynucleotide sequences encoding these polypeptides are also provided. The present invention also encompasses the use of these C-terminal DmTNF deletion polypeptides as immunogenic and/or antigenic epitopes as described elsewhere herein.

Alternatively, preferred polypeptides of the present invention may comprise polypeptide sequences corresponding to, for example, internal regions of the DmTNF polypeptide (e.g., any combination of both N- and C-terminal DmTNF polypeptide deletions) of SEQ ID NO:2. For example, internal regions could be defined by the equation: amino acid NX to amino acid CX, wherein NX refers to any N-terminal deletion polypeptide amino acid of DmTNF (SEQ ID NO:2), and where CX refers to any C-terminal deletion polypeptide amino acid of DmTNF (SEQ ID NO:2). Polynucleotides encoding these polypeptides are also provided. The present invention also encompasses the use of these polypeptides as an immunogenic and/or antigenic epitope as described elsewhere herein.

In preferred embodiments, the following DmTNF TNF domain amino acid substitutions are encompassed by the present invention: wherein L316 is substituted with either an A, C, D, E, F, G, H, I, K, M, N, P, Q, R, S, T, V, W, or Y; wherein T317 is substituted with either an A, C, D, E, F, G, H, I, K, L, M, N, P, Q, R, S, V, W, or Y; wherein V318 is substituted with either an A, C, D, E, F, G, H, I, K, L, M, N, P, Q, R, S, T, W, or Y; wherein T319 is substituted with either an A, C, D, E, F, G, H, I, K, L, M, N, P, Q, R, S, V, W, or Y; wherein N320 is substituted with either an A, C, D, E, F, G, H, I, K, L, M, P, Q, R, S, T, V, W, or Y; wherein A321 is substituted with either a C, D, E, F, G, H, I, K, L, M, N P, Q, R, S, T, V, W, or Y; wherein G322 is substituted with either an A, C, D, E, F, H, I, K, L, M, N, P, Q, R, S, T, V, W, or Y; wherein L323 is substituted with either an A, C, D, E, F, G, H, I, K, M, N, P, Q, R, S, T, V, W, or Y; wherein Y324 is substituted with either an A, C, D, E, F, G, H, I, K, L, M, N, P, Q, R, S, T, V, or W; wherein Y325 is, substituted with either an A, C, D, E, F, G, H, I, K, L, M, N, P, Q, R, S, T, V, or W; wherein V326 is substituted with either an A, C, D, E, F, G, H, I, K, L, M, N, P, Q, R, S, T, W, or Y; wherein Y327 is substituted with either an A, C, D, E, F, G, H, I, K, L, M, N, P, Q, R, S, T, V, or W; wherein A328 is substituted with either a C, D, E, F, G, H, I, K, L, M, N, P, Q, R, S, T, V, W, or Y; wherein Q329 is substituted with either an A, C, D, E, F, G, H, I, K, L, M, N, P, R, S, T, V, W, or Y; wherein 11330 is substituted with either an A, C, D, E, F, G, H, K, L, M, N, P, Q, R, S, T, V, W, or Y; and/or wherein W331 is substituted with either an A, C, D, E, F, G, H, I, K, L, M, N, P, Q, R, S, T, V, or Y of SEQ ID NO:2, in addition to any combination thereof. The present invention also encompasses the use of these DmTNF TNF domain amino acid substituted polypeptides as immunogenic and/or antigenic epitopes as described elsewhere herein.

In preferred embodiments, the following DmTNF TNF domain conservative amino acid substitutions are encompassed by the present invention: wherein L316 is substituted with either an A, I, or V; wherein T317 is substituted with either an A, G, M, or S; wherein V318 is substituted with either an A, I, or L; wherein T319 is substituted with either an A, G, M, or S; wherein N320 is substituted with a Q; wherein A321 is substituted with either a G, I, L, M, S, T, or V; wherein G322 is substituted with either an A, M, S, or T; wherein L323 is substituted with either an A, I, or V; wherein Y324 is either an F, or W; wherein Y325 is either an F, or W; wherein V326 is substituted with either an A, I, or L; wherein Y327 is either an F, or W; wherein A328 is substituted with either a G, I, L, M, S, T, or V; wherein Q329 is substituted with a N; wherein I330 is substituted with either an A, V, or L; and/or wherein W331 is either an F, or Y of SEQ ID NO:2 in addition to any combination thereof. Other suitable substitutions within the DmTNF TNF domain are encompassed by the present invention and are referenced elsewhere herein. The present invention also encompasses the use of these DmTNF TNF domain conservative amino acid substituted polypeptides as immunogenic and/or antigenic epitopes as described elsewhere herein.

The DmTNF polypeptide has been shown to comprise two glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following, consensus pattern, N-{P}-[ST]-{P }, wherein N represents the glycosylation site. However, it is well known that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Phr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz. W. J., Proc. Natl. Acad. Sci, U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention QNIQGNHTELQEKS (SEQ ID NO:35), and/or LREGNNRSYFGIF. K (SEQ ID NO:36). Polynucleotides encoding these polypeptides are also provided. The present invention also encompasses the use of these DmTNF asparagine glycosylation site polypeptides as immunogenic and/or antigenic epitopes as described elsewhere herein.

The DmTNF polypeptides of the present invention were determined to comprise several phosphorylation sites based upon the Motif algorithm (Genetics Computer Group, Inc.). The phosphorylation of such sites may regulate some biological activity of the DmTNF polypeptide. For example, phosphorylation at specific sites may be involved in regulating the proteins ability to associate or bind to other molecules (e.g., proteins, ligands, substrates, DNA, etc.).

Specifically, the DmTNF polypeptide was predicted to comprise two tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Nail. Acad. Sci. U.S.A. 79:973–977 (1982); Hunter T., J. Biol. Chem. 257:4843–4848(1982), and Cooper J. A., Esch F. S., Taylor S. S., Hunter T., J. Biol. Chem. 259:7835–7841(1984), which are hereby incorporated herein by reference.

In preferred embodiments, the following tyrosine phosphorylation site polypeptides are encompassed by the present invention: HLSSRRRHQESMGYHGDMY (SEQ ID NO:42), and/or LSSRRRHQESMGYHGDMY (SEQ ID NO:43). Polynucleotides encoding these polypeptides are also provided. The present invention also encompasses the use of these DmTNF tyrosine phosphorylation site polypeptides as immunogenic and/or antigenic epitopes as described elsewhere herein.

The DmTNF polypeptide was predicted to comprise five PKC phosphorylation sites using the Motif algorithm (Genetics Computer Group, Inc). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: MTAETLKPFITP (SEQ ID NO:37), LTIWQTTRVSHLD (SEQ ID NO:38), DKELKSLKRVVDN (SEQ ID NO:39), AHFHLSSRRRHQE (SEQ ID NO:40), and/or HFHLSSRRRHQES (SEQ ID NO:41). Polynucleotides encoding these polypeptides are also provided. The present invention also encompasses the use of these DmTNF PKC phosphorylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2152 of SEQ ID NO:1, b is an integer between 15 to 2166, where both a and b correspond to the positions of nucleotide residues shown in SEQ ID NO:1, and where b is greater than or equal to a+14.

Features of the Polypeptide Encoded by Gene No-2

The polypeptide of this gene provided as SEQ ID NO:4 (FIGS. 2A–B), encoded by the polynucleotide sequence according to SEQ ID NO:3 (FIGS. 2A–B), and/or encoded by the polynucleotide contained within the clone, DmTNFv1, has significant homology at the nucleotide and amino acid level to the human osteoprotegerin protein (Osteoprotegerin; Genbank Accession No. gib 12643360; SEQ ID NO:7), the human hCD27 ligand protein (hCD27L; Genbank Accession No. gilP32970; SEQ ID NO:35), the human CD30 ligand protein (hCD30L; Genbank Accession No. gilP32971; SEQ ID NO:36); the human TRAIL protein (hTRAIL; Genbank Accession No. gilP50591; SEQ ID NO:37); the human ectodysplasmin_A protein (hEctodysplasmin_A; Genbank Accession No. gilQ92838; SEQ ID NO:8), and the mouse ectodysplasmin_A protein (mEctodysplasmin_A; Genbank Accession No. gilNP034229; SEQ ID NO:9). An alignment of the DmTNFv1 polypeptide with these proteins is provided in FIGS. 6A–B.

The DmTNFv1 polypeptide was determined to share 23.8% identity and 30.5% similarity with the human osteoprotegerin protein (Osteoprotegerin; Genbank Accession No. gil12643360; SEQ ID NO:7), to share 12.5% identity and 37.5% similarity with the human hCD27 ligand protein (hCD27L; Genbank Accession No. gilP32970; SEQ ID NO:35), to share 20% identity and 26.7% similarity with the human CD30 ligand protein (hCD30L; Genbank Accession No. gilP32971; SEQ ID NO:36); to share 23.3% identity and 32.7% similarity with the human TRAIL, protein (hTRAIL; Genbank Accession No. gilP50591; SEQ ID NO:37); to share 21.8% identity and 28.6% similarity with the human ectodysplasmin_A protein (mEctodysplasmin_A; Genbank Accession No. gilQ92838; SEQ ID NO:8), and to share 21% identity and 28.6% similarity with the mouse ectodysplasmin_A protein (mEctodysplasmin_A; Genbank Accession No. gilNP_034229; SEQ ID NO:9) as shown in FIG. 11.

Expression profiling designed to measure the steady state mRNA levels encoding the DmTNF polypeptide showed predominately high expression levels in Drosophila embryos, significantly in larvae, and to a lesser extent, in adult (as shown in FIG. 3).

Moreover, in situ hybridization of Drosophila embryos at various developmental stages indicated that DmTNF gene expression was upregulated in the dorsal region of the developing embryo (stage 415) at a time coincident with the activation of Rel activity in the ventral region only. Specifically, DmTNF was expressed only in areas where Rel proteins are not activated. The results, in conjunction with the results provided elsewhere herein, suggest DmTNF is negatively regulated by the Rel activation pathway in embryogenesis.

Based upon the observed homology, the polypeptide of the present invention may share at least some biological activity with tumor necrosis family members, specifically with CD27L, CD30L and TRAIL, and preferably with the tumor necrosis factor family members referenced elsewhere herein.

The DmTNFv1 polypeptide was determined to comprise a signal sequence from about amino acid 'to about amino acid 52 of SEQ ID NO:4 (FIGS. 2A–B) according to the SPScan computer algorithm (Genetics Computer Group suite of programs). Based upon the predicted signal peptide cleavage site, the mature DmTNFv1 polypeptide is expected to be from about amino acid 53 to about amino acid 406 of SEQ ID NO:4 (FIGS. 2A–B). As this determination was based upon the prediction from a computer algorithm, the exact physiological cleavage site may vary, as discussed more particularly herein. In this context, the term "about" should be construed to mean 1, 2, 3, 4, 5, 6, 7, 8, 9, 10, 11, 12, 13, 14, 15, 16, 17, 18, 19, or 20 more amino acids in either the N- or C-terminal direction of the above referenced polypeptide. Polynucleotides encoding these polypeptides are also provided.

In addition to the mature polypeptide above, the polynucleotides encoding the mature polypeptide are also encompassed by the present invention. Specifically, from about nucleotide position 157 to about nucleotide position 1218 of SEQ ID NO:3 (FIGS. 2A–B).

Similarly, several members of the TNF family, such as, for example, CD27L, CD30L and TRAIL, in addition to the ectodysplasin-A protein, are type II transmembrane proteins. Hydrophobicity plot analysis using Kyte-Doolittle Hydropathy algorithm suggests that DmTNFv 1 is also a type II transmembrane protein (e.g., potentially secreted protein), with a short intracellular domain at the NH2 terminal of DmTNFv1 and a long extracellular domain at the COOH terminal of DmTNFv1 as shown in FIG. 7.

In terms of general utility of the novel DmTNFv1 of the present invention, gene expression of DmTNFv1 suggests it is important in immunomodulation and metabolic biology in Drosophila, and potentially humans. Biochemical pathways are highly conserved from Drosophila to man; therefore, studies in Drosophila are very relevant to human biology. Through tools common to Drosophila research the biological significance and biochemical pathways of DmTNFv1 can be elucidated. Loss of function mutations in DmTNFv 1 will be identified and transgenic flies can be generated to overexpress DmTNFv1 and mutant forms in specific tissues. These types of experiments may be used to identify the DmTNFv1 receptor, its signaling pathway and the biological functions of DmTNFv1.

Similar to other receptor systems being investigated (e.g., CD40/CD40L, 4-1BB/4-1BL, Fas/FasL) it is contemplated by the present invention that the interaction between the novel DmTNFv1 (or human homologues found using the novel DmTNFv 1 of the present invention) and its receptor may serve as a novel target for immunosuppressive, anti-inflammatory and/or immunostimulatory drug development.

The present invention relates to the nucleic acid sequence or a fragment thereof (referred to herein as a "polynucleotide") of the novel DmTNFv1 as shown above (SEQ ID NO:3), as well as to the amino acid sequence of the DmTNFv1 (SEQ ID NO:4), and biologically active portions thereof.

The present invention further relates to a tumor necrosis factor molecule polypeptide, DmTNFv1, which has the deduced amino acid sequence as shown in SEQ ID NO:4, as well as fragments, analogs and derivatives of such polypeptide.

DmTNFv1 polynucleotide and polypeptides, including variants or fragments thereof, can be used for the generation of mutant phenotypes in animal models or in living cells. Preferably, such phenotypes are genetically modified to either express or misexpress the DmTNFv1 gene, for example using transposon mutagenesis, RNA interference, chemical mutagenesis, or other genetic techniques. As discussed elsewhere herein, the expression of the DmTNFv1 protein may be driven by a heterologous promoter that is tissue-specific, developmentally specific, or inducible, enabling the effects of the expression or misexpression can be observed in specific tissues, at certain developmental stages, or at specified times, respectively. Such mutant phenotypes are useful for studying the regulation of DmTNFv 1, and the use of DmTNFv1 as a drug target in an effort to identify potential therapeutic compounds. Due to the ability to carry out large scale, systematic genetic screens, the use of Drosophila has great utility for analyzing the expression and mis-expression of DmTNFv1, TNF proteins, and/or TNF homology. Additionally, the DmTNFv1 pathway protein may be linked to one or more selectable markers that allows detection of expression. For example, the expression of the DmTNFv1 results in an identifiable phenotype.

DmTNFv1 polynucleotide and polypeptides, including variants or fragments thereof, are useful for screening molecules that modulate DmTNFv1, or the DmTNFv1 pathway.

In addition, DmTNFv1 polynucleotide and polypeptides, including variants or fragments thereof, are useful in the elucidation of biological pathways, particularly TNF pathways (Margolis, J. and Duyk, G. Nat Biotechnol. (1998)16: 311, Matthews D. and Kopczynski , J (2001) Drug Disc. Today 6: 141–149). DmTNFv1 polynucleotide and polypeptides, including variants or fragments thereof, are useful for identifying other TNF family members.

The homology to the human osteoprotegerin ligand protein, combined with the observed expression in Drosophila embryos, suggests the DmTNFv1 polynucleotides and polypeptides of the present invention have uses which include treating, ameliorating, and/or preventing diseases and disorders related to aberrant osteoprotegerin ligand function. Moreover, the DmTNFv1 polynucleotides and polypeptides of the present invention may be useful for augmenting the ability of dendritic cells to stimulate naive t-cell proliferation, in regulating interaction between t cells and dendritic cells, modulating the regulation of the t cell-dependent immune response, in addition to, potentially enhancing bone-resorption in humoral hypercalcemia of malignancy, in animals, preferably humans. DmTNFv1 may also be useful in modulating immune responses, and/or ameliorating or preventing morphological aberrations in insects, preferably in flies, such as Drosophila.

In addition, the negative regulation of DmTNF by Rel strongly suggests DmTNF polynucleotides and polypeptides of the present invention have uses which include modulating the innate immune response in invertebrates, particularly flies, and most preferably in Drosophila. Moreover, the specific expression in embryos also suggests DmTNF polynucleotides and polypeptides of the present invention have uses which include modulating development and/or patterning during embryogenesis in invertebrates, particularly flies, and most preferably in Drosophila.

As noted above, the DmTNFv1 polypeptide was also determined to share significant homology with both the human and mouse ectodysplasmin_A protein. Mutations within ectodysplasin-A in mice has been shown in result in a Tabby phenotype (i.e., no sweat glands). Ectodysplasin-A has been shown to function in epithelial morphogenesis and promotes cell-matrix adhesion In addition, mutations in the human ectodysplasmin-A has been directly implicated in X-linked anhidrotic (hypohidrotic) ectodermal dysplasia (Kere, J., et al., Nat. Genet. 13 (4), 409–416 (1996)). This disorder results in sparse hair (atrichosis or hypotrichosis), abnormal or missing teeth and the inability to sweat due to the absence of sweat glands in humans.

Therefore, DmTNFv1 polynucleotides and polypeptides, including fragments and/or antagonists thereof, may have uses which include modulating epithelial morphogenesis, cell-matrix adhesion, in flies, preferably Drosophila, and potentially in other organisms as well, preferably mammals, such as humans, mice, and rats. Moreover, DmTNFv1 polypeptides and polypeptides, including fragments and/or antagonists thereof, may have uses which include treating, ameliorating, and/or preventing X-linked anhidrotic (hypohidrotic) ectodermal dysplasia, including X-linked anhidrotic (hypohidrotic) ectodermal dysplasia-like disorders, such as sparse hair, abnormal or missing teeth, and sweat gland aberrations, in animals, preferably insects, and potentially in humans.

In preferred embodiments, the following N-terminal DmTNFv1 deletion polypeptides are encompassed by the present invention: M1-V406, T2-V406, A3-V406, E4-V406, T5-V406, L6-V406, K7-V406, P8-V406, F9-V406, I10-V406, T11-V406, P12-V406, T13-V406, S14-V406, A15-V406, N16-V406, D17-V406, D18-V406, G19-V406, F20-V406, P21-V406, A22-V406, K23-V406, A24-V406, T25-V406, S26-V406, T27-V406, A28-V406, T29-V406, A30-V406, Q31-V406, R32-V406, R33-V406, T34-V406, R35-V406, Q36-V406, L37-V406, I38-V406, P39-V406, L40-V406, V41-V406, L42-V406, G43-V406, F44-V406, I45-V406, G46-V406, L47-V406, G48-V406, L49-V406, V50-V406, V51-V406, A52-V406, I53-V406, L54-V406, A55-V406, L56-V406, T57-V406, I58-V406, W59-V406, Q60-V406, T61-V406, T62-V406, R63-V406, V64-V406, S65-V406, H66-V406, L67-V406, D68-V406, K69-V406, E70-V406, L71-V406, K72-V406, S73-V406, L74-V406, K75-V406, R76-V406, V77-V406, V78-V406, D39-V406, N80-V406, L81-V406, Q82-V406, Q83-V406, R84-V406, L85-V406, G86-V406, I87-V406, N88-V406, Y89-V406, L90-V406, D91-V406, E92-V406, F93-V406, D94-V406, E95-V406, F96-V406, Q97-V406, K98-V406, E99-V406, Y100-V406, E101-V406, N102-V406, A103-V406, L104-V406, I105-V406, D106-V406, Y107-V406, P108-V406, K109-V406, K110-V406, V111-V406, D112-V406, G113-V406, L114-V406, T115-V406, D116-V406, E117-V406, E118-V406, D119-V406, D120-V406, D121-V406, D122-V406, G123-V406, D124-V406, G125-V406, L126-V406, D127-V406, S128-V406, I129-V406, A130-V406, D131-V406, D132-V406, E133-V406, D134-V406, D135-V406, D136-V406, V137-V406, S138-V406, Y139-V406, S140-V406, S141-V406, V142-V406, D143-V406, D144-V406, V145-V406, G146-V406, A147-V406, D148-V406, Y149-V406, E150-V406, D151-V406, Y152-V406, T153-V406, D154-V406, M155-V406, L156-V406, N157-V406, K158-V406, L159-V406, N160-V406, N161-V406, A162-V406, H163-V406, T164-V406, G165-V406, T166-V406, T167-V406, P168-V406, T169-V406, S170-V406, E171-V406, T172-V406, T173-V406, A174-V406, E175-V406, G176-V406, E177-V406, G178-V406, E179-V406, T180-V406, D181-V406, S182-V406, A183-V406, S184-V406, S185-V406, A186-V406, S187-V406, N188-V406, D189-V406, D190-V406, N191-V406, V192-V406, F193-V406, D194-V406, D195-V406, F196-V406, T197-V406, S198-V406, Y199-V406, N200-V406, A201-V406, H202-V406, K203-V406, K204-V406, K205-V406, Q206-V406, E207-V406, R208-V406, K209-V406, S210-V406, R211-V406, S212-V406, I213-V406, A214-V406, D215-V406, V216-V406, R217-V406, N218-V406, E219-V406, E220-V406, Q221-V406, N222-V406, I223-V406, Q224-V406, G225-V406, N226-V406, H227-V406, T228-V406, E229-V406, L230-V406, Q231-V406, E232-V406, K233-V406, S234-V406, S235-V406, N236-V406, E237-V406, A238-V406, T239-V406, S240-V406, K241-V406, E242-V406, R243-V406, M244-V406, H245-V406, S246-V406, R247-V406, H248-V406, R249-V406, H250-V406, L251-V406, L252-V406, V253-V406, S254-V406, K255-V406, G256-V406, E257-V406, S258-V406, L259-V406, L260-V406, S261-V406, A262-V406, R263-V406, S264-V406, E265-V406, D266-V406, S267-V406, R268-V406, P269-V406, A270-V406, A271-V406, H272-V406, F273-V406, H274-V406, L275-V406, S276-V406, S277-V406, R278-V406, R279-V406, R280-V406, H281-V406, Q282-V406, G283-V406, S284-V406, M285-V406, G286-V406, Y287-V406, H288-V406, G289-V406, D290-V406, M291-V406, Y292-V406, I293-V406, G294-V406, N295-V406, D296-V406, N297-V406, E298-V406, R299-V406, N300-V406, S301-V406, Y302-V406, Q303-V406, G304-V406, H305-V406, F306-V406, Q307-V406, T308-V406, R309-V406, D310-V406, G311-V406, V312-V406, I313-V406, T314-V406, V315-V406, T316-V406, N317-V406, T318-V406, G319-V406, L320-V406, Y321-V406, Y322-V406, V323-V406, Y324-V406, A325-V406, Q326-V406, I327-V406, C328-V406, Y329-V406, N330-V406, N331-V406, S332-V406, H333-V406, D334-V406, Q335-V406, N336-V406, G337-V406, F338-V406, I339-V406, V340-V406, F341-V406, Q342-V406, G343-V406, D344-V406, T345-V406, P346-V406, F347-V406, L348-V406, Q349-V406, C350-V406, L351-V406, N352-V406, T353-V406, V354-V406, P355-V406, T356-V406, N357-V406, M358-V406, P359-V406, H360-V406, K361-V406, V362-V406, H363-V406, T364-V406, C365-V406, H366-V406, T367-V406, S368-V406, G369-V406, L370-V406, I371-V406, H372-V406, L373-V406, E374-V406, R375-V406, N376-V406, E377-V406, R378-V406, I379-V406, H380-V406, L381-V406, K382-V406, D383-V406, I384-V406, H385-V406, N386-V406, D387-V406, R388-V406, N389-V406, A390-V406, V391-V406, L392-V406, R393-V406, E394-V406, G395-V406, N396-V406, N397-V406, R398-V406, S399-V406, and/or Y400-V406 of SEQ ID NO:4. Polynucleotide sequences encoding these polypeptides are also provided. The present invention also encompasses the use of these N-terminal DmTNFv1 deletion polypeptides as immunogenic and/or antigenic epitopes as described elsewhere herein.

In preferred embodiments, the following C-terminal DmTNFv1 deletion polypeptides are encompassed by the present invention: M1-V406, M1-K405, M1-F404, M1-I403, M1-G402, M1-F401, M1-Y400, M1-S399, M1-R398, M1-N397, M1-N396, M1-G395, M1-E394, M1-R393, M1-L392, M1-V391, M1-A390, M1-N389, M1-R388, M1-D387, M1-N386, M1-H385, M1-I384, M1-D383, M1-K382, M1-L381, M1-H380, M1-I379, M1-R378, M1-E377, M1-N376, M1-R375, M1-E374, M1-L373, M1-H372, M1-I371, M1-L370, M1-G369, M1-S368, M1-T367, M1-H366, M1-C365, M1-T364, M1-H363, M1-V362, M1-K361, M1-H360, M1-P359, M1-M358, M1-N357, M1-T356, M1-P355, M1-V354, M1-T353, M1-N352, M1-L351, M1-C350, M1-Q349, M1-L348, M1-F347, M1-P346, M1-T345, M1-D344, M1-G343, M1-Q342, M1-F341, M1-V340, M1-I339, M1-F338, M1-G337, M1-N336, M1-Q335, M1-D334, M1-H333, M1-S332, M1-N331, M1-N330, M1-Y329, M1-C328, M1-I327, M1-Q326, M1-A325, M1-Y324, M1-V323, M1-Y322, M1-Y321, M1-L320, M1-G319, M1-T318, M1-N317, M1-T316, M1-V315, M1-T314, M1-L313, M1-V312, M1-G311, M1-D310, M1-R309, M1-T308, M1-Q307, M1-F306, M1-H305, M1-G304, M1-Q303, M1-Y302, M1-S301, M1-N300, M1-R299, M1-E298, M1-N297, M1-D296, M1-N295, M1-G294, M1-I293, M1-Y292, M1-M291, M1-D290, M1-G289, M1-H288, M1-Y287, M1-G286, M1-M285, M1-S284, M1-G283, M1-Q282, M1-H281, M1-R280, M1-R279, M1-R278, M1-S277, M1-S276, M1-L275, M1-H274, M1-F273, M1-H272, M1-A271, M1-A270, M1-P269, M1-R268, M1-S267, M1-D266, M1-E265, M1-S264, M1-R263, M1-A262, M1-S261, M1-L260, M1-L259, M1-S258, M1-E257, M1-G256, M1-K255, M1-R254, M1-V253, M1-L252, M1-L251, M1-H250, M1-R249, M1-H248, M1-R247, M1-S246, M1-H245, M1-M244, M1-R243, M1-E242, M1-K241, M1-S240, M1-T239, M1-A238, M1-E237, M1-N236, M1-S235, M1-S234, M1-K233, M1-E232, M1-Q231, M1-L230, M1-E229, M1-T228, M1-H227, M1-N226, M1-G225, M1-Q224, M1-I223, M1-N222, M1-Q221, M1-E220, M1-E219, M1-N218, M1-R217, M1-V216, M1-D215, M1-A214, M1-I213, M1-S212, M1-R211, M1-S210, M1-K209, M1-R208, M1-E207, M1-Q206, M1-K205, M1-K204, M1-K203, M1-H202, M1-A201, M1-N200, M1-Y199, M1-S198, M1-T197, M1-F196, M1-D195, M1-D194, M1-F193, M1-V192, M1-N191, M1-D190, M1-D189, M1-N188, M1-S187, M1-A186, M1-S185, M1-S184, M1-A183, M1-S182, M1-D181, M1-T180, M1-E179, M1-G178, M1-E177, M1-G176, M1-E175, M1-A174, M1-T173, M1-T172, M1-E171, M1-S170, M1-T169, M1-P168, M1-T167, M1-T166, M1-G165, M1-T164, M1-H163, M1-A162, M1-N161, M1-N160, M1-L159, M1-K158, M1-N157, M1-L156, M1-M155, M1-D154, M1-T153, M1-Y152, M1-D151, M1-E150, M1-Y149, M1-D148, M1-A147, M1-G146, M1-V145, M1-D144, M1-D143, M1-V142, M1-S141, M1-S140, M1-Y139, M1-S138, M1-V137, M1-D136, M1-D135, M1-D134, M1-E133, M1-D132, M1-D131, M1-A130, M1-I129, M1-S128, M1-D127, M1-L126, M1-G125, M1-D124, M1-G123, M1-D122, M1-D121, M1-D120, M1-D119, M1-E118, M1-E117, M1-D116, M1-T115, M1-L114, M1-G1.13, M1-D112, M1-V111, M1-K110, M1-K109, M1-P108, M1-Y107, M1-D106, M1-I105, M1-L104, M1-A103, M1-N102, M1-E101, M1-Y100, M1-E99, M1-K98, M1-Q97, M1-T96, M1-E95, M1-D94, M1-F93, M1-E92, M1-D91, M1-I90, M1-Y89, M1-N88, M1-I87, M1-G86, M1-L85, M1-R84, M1-Q83, M1-Q82, M1-L81, M1-N80, M1-D79, M1-V78, M1-V77, M1-R76, M1-K75, M1-L74, M1-S73, M1-K72, M1-L71, M1-E70, M1-K69, M1-D68, M1-L67, M1-H66, M1-S65, M1-V64, M1-R63, M1-T62, M1-T61, M1-Q60, M1-W59, M1-I58, M1-T57, M1-L56, M1-A55, M1-L54, M1-I53, M1-A52, M1-V51, M1-V50, M1-I49, M1-G48, M1-L47, M1-G46, M1-I45, M1-F44, M1-G43, M1-L42, M1-V41, M1-L40, M1-P39, M1-I38, M1-L37, M1-Q36, M1-R35, M1-T34, M1-R33, M1-R32, M1-Q31, M1-A30, M1-T29, M1-A28, M1-T27, M1-S26, M1-T25, M1-A24, M1-K23, M1-A22, M1-P21, M1-I720, M1-G19, M1-D18, M1-D17, M1-N16, M1-A15, M1-S14, M1-T13, M1-P12, M1-T11, M1-I10, M1-F9, M1-P8, and/or M1-K7 of SEQ ID NO:4. Polynucleotide sequences encoding these polypeptides are also provided. The present invention also encompasses the use of these C-terminal DmTNFv1 deletion polypeptides as immunogenic and/or antigenic epitopes as described elsewhere herein.

Alternatively, preferred polypeptides of the present invention may comprise polypeptide sequences corresponding to, for example, internal regions of the DmTNFv1 polypeptide (e.g., any combination of both N- and C-terminal DmTNFv1 polypeptide deletions) of SEQ ID NOA. For example, internal regions could be defined by the equation: amino acid NX to amino acid CX, wherein NX refers to any N-terminal deletion polypeptide amino acid of DmTNFv1 (SEQ ID NO:4), and where CX refers to any C-terminal deletion polypeptide amino acid of DmTNFv1 (SEQ ID NO:4). Polynucleotides encoding these polypeptides are also provided. The present invention also encompasses the use of these polypeptides as an immunogenic and/or antigenic epitope as described elsewhere herein.

In preferred embodiments, the following DmTNFv1 TNF domain amino acid substitutions are encompassed by the present invention: wherein L313 is substituted with either an A, C, D, E, F, G, H, I, K, M, N, P, Q, R, S, T, V, W, or Y; wherein T314 is substituted with either an A, C, D, E, F, G, H, I, K, L, M, N, P, Q, R, S, V, W, or Y; wherein V315 is substituted with either an A, C, D, E, F, G, H, I, K, L, M, N, P, Q, R, S, T, W, or Y; wherein T316 is substituted with either an A, C, D, E, F, G, H, I, K, L, M, N, P, Q, R, S, V, W, or Y; wherein N317 is substituted with either an A, C, D, E, F, G, H, I, K, L, M, P, Q, R, S, T, V, W, or Y; wherein T318 is substituted with either an A, C, D, E, F, G, H, I, K, L, M, N, P, Q, R, S, V, W, or Y; wherein G319 is substituted with either an A, C, D, E, F, H, I, K, L, M, N, P, Q, R, S, T, V, W, or Y; wherein L320 is substituted with either an A, C, D, E, F, G, H, I, K, M, N, P, Q, R, S, T, V, W, or Y; wherein Y321 is substituted with either an A, C, D, E, F, G, H, I, K, L, M, N, P, Q, R, S, T, V, or W; wherein Y322 is substituted with either an A, C, D, E, F, G, H, I, K, L, M, N, P, Q, R, S, T, V, or W; wherein V323 is substituted with either an A, C, D, E, F, G, H, I, K, L, M, N, P, Q, R, S, T, W, or Y; wherein Y324 is substituted with either an A, C, D, E, F, G, H, I, K, L, M, N, P, Q, R, S, T, V, or W; wherein A325 is substituted with either a C, D, E, F, G, H, I, K, L, M, N, P, Q, R, S, T, V, W, or Y; wherein Q326 is substituted with either an A, C, D, E, F, G, H, I, K, L, M, N, P, R, S, T, V, W, or Y; wherein I327 is substituted with either an A, C, D, E, F, G, H, K, L, M, N, P, Q, R, S, T, V, W, or Y; wherein C328 is substituted with either an A, D, E, F, G, H, I, K, L, M, N, P, Q, R, S, T, V, W, or Y; and/or wherein Y329 is substituted with either an A, C, D, E, F, G, H, I, K, L, M, N, P, Q, R, S, T, V, or W of SEQ ID NO:4, in addition to any combination thereof. The present invention also encompasses the use of these DmTNFv1 TNF domain amino acid substituted polypeptides as immunogenic and/or antigenic epitopes as described elsewhere herein.

In preferred embodiments, the following DmTNFv1 TNF domain conservative amino acid substitutions are encompassed by the present invention: wherein L313 is substituted with either an A, I, or V; wherein T314 is substituted with either an A, G, M, or S; wherein V315 is substituted with either an A, I, or L; wherein T316 is substituted with either an A, G, M, or S; wherein N317 is substituted with a Q; wherein T318 is substituted with either an A, G, M, or S; wherein G319 is substituted with either an A, M, S, or T; wherein L320 is substituted with either an A, I, or V; wherein Y321 is either an F, or W; wherein Y322 is either an F, or W; wherein V323 is substituted with either an A, I, or L; wherein Y324 is either an F, or W; wherein A325 is substituted with either a G, I, L, M, S, T, or V; wherein Q326 is substituted with a N; wherein I327 is substituted with either an A, V, or L; wherein C328 is a C; and/or wherein Y329 is either an F, or W of SEQ ID NO:4 in addition to any combination thereof. Other suitable substitutions within the DmTNFv1 TNF domain are encompassed by the present invention and are referenced elsewhere herein. The present invention also encompasses the use of these DmTNFv1 TNF domain conservative amino acid substituted polypeptides as immunogenic and/or antigenic epitopes as described elsewhere herein.

The DmTNFv1 polypeptide has been shown to comprise three glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa Ser/Tr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74;134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention: QNIQGNHTELQEKS (SEQ ID NO:44), AQICYNNSHDQNGF (SEQ ID NO:45), and/or LREGNNRSYFGIFK (SEQ ID NO:46). Polynucleotides encoding these polypeptides are also provided. The present invention also encompasses the use of these DmTNFv1 asparagine glycosylation site polypeptides as immunogenic and/or antigenic epitopes as described elsewhere herein.

The DMTNFV1 polypeptides of the present invention were determined to comprise several phosphorylation sites based upon the Motif algorithm (Genetics Computer Group, Inc.). The phosphorylation of such sites may regulate some biological activity of the DMTNFV1 polypeptide. For example, phosphorylation al specific sites may be involved in regulating the proteins ability to associate or bind to other molecules (e.g., proteins, ligands, substrates, DNA, etc.).

The DMTNFV1 polypeptide was predicted to comprise seven PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: MTAETLKPFITP (SEQ ID NO:46), LTIWQTTRVSHLD (SEQ ID NO:47), DKELKSLKRVVDN (SEQ ID NO:48), SSNEATSKERMHS (SEQ ID NO:49), GESLLSARSEDSR (SEQ ID NO:50), AHFHLSSRRRHQG (SEQ ID NO:51), and/or HFHLSSRRRHQGS (SEQ ID NO:52). Polynucleotides encoding these polypeptides are also provided. The present invention also encompasses the use of these DMTNFV1 PKC phosphorylation site polypeptides as immunogenic and/or antigenic epitopes as described elsewhere herein.

Consistent with the DmTNFv1 polypeptide representing a TNT superfamily member, the DMTNFV1 polypeptide was predicted to comprise a TNF family domain using the Motif algorithm (Genetics Computer Group, Inc.). The following cytokines can be grouped into a family on the basis of sequence, functional, and structural similarities: Tumor Necrosis Factor (TNF) (also known as cachectin or TNF-alpha), is a cytokine which has a wide variety of functions. It can cause cytolysis of certain tumor cell lines, it is involved in the induction of cachexia, it is a potent pyrogen, causing fever by direct action or by stimulation of interleukin-1 secretion, finally, it can stimulate cell proliferation and induce cell differentiation under certain conditions; Lymphotoxin-alpha (LT-alpha) and lymphotoxin-beta (LT-beta), two related cytokines produced by lymphocytes and which are cytotoxic for a wide range of tumor cells in vitro and in vivo; T cell antigen gp39 (CD40L), a cytokine which seems to be important in B-cell development and activation; CD27L, a cytokine which plays a role in T-cell activation. It induces the proliferation of costimulated T cells and enhances the generation of cytolytic T cells; CD30L, a cytokine which induces proliferation of T cells; FASL, a cytokine involved in cell death; 4-1BBL, an inducible T cell surface molecule that contributes to T-cell stimulation; OX40L, a cytokine that co-stimulates T cell proliferation and cytokine production; TNF-related apoptosis inducing ligand (TRAIL), a cytokine that induces apoptosis; TNF-alpha is synthesized as a type II membrane protein which then undergoes post-translational cleavage liberating the extracellular domain. CD27L, CD30L, CD40L, FASL, LT-beta, 4-1BBL and TRAIL also appear to be type II membrane proteins. LT-alpha is a secreted protein. All these cytokines seem to forth homotrimeric (or heterotrimeric in the case of LT-alpha/beta) complexes that are recognized by their specific receptors.

The TNF domain represents the most conserved region within the TNF family. This domain is located in a beta-strand in the central section of these proteins and has the following consensus pattern: [LV]-x-[LIVM]-x(3)-G-[LIVMF]-Y-[LIVMFY] (2)-x(2)-[QEKHL]-[LIVMGT]-x-[LIVMFY], wherein "x" is equals any amino acid.

Additional information related to the TNF domain and/or TNF domain containing proteins may be found by reference to the following publications which are hereby incorporated herein by reference in their entirety: Peitsch M. C., Jongeneel C. V., Int. Immunol. 5:233–238(1993); Farrah T., Smith C. A., Nature 358:26-26(1992); Bazan J. F., Curr. Biol. 3:603–606(1993); Beutler B., Cerami A, Biochemistry, 27:7575–7582(1988); Vileek J., Lee T. H., J. Biol. Chem. 266:7313–7316(1991); Browning J. L., Ngam-Ek A., Lawton P., Demarinis J., Tizard R., Chow E. P., Hession C., O'Brine-Greco B., Foley S. F., Ware C. F., Cell 72:847–856 (1993); Suda T., Takahashi T., Golstein P., Nagata S, Cell 75:1169–1178(1993); Baum P. R., Gayle R. B. III, Ramsdell F., Srinivasan S., Sorensen R. A., Watson M. L., Seldin M. F., Baker E., Sutherland G. R.; Clifford K. N., Alderson M. R., Goodwin R. G., Fanslow W. C., EMBO J. 13:3992 4001(1994); and Wiley S. R., Schooley K., Smolak P. J., Din W. S., Huang C. -P., Nicholl J. K., Sutherland G. R., Davis-Smith T., Rauch C., Smith C. A., Goodwin R. G., Immunity 3:673–682(1995).

In preferred embodiments, the following TNF domain polypeptide is encompassed by the present invention:

TRDGVLTVTNTGLYYVYAQICYNNSHD (SEQ ID NO:53). Polynucleotides encoding this polypeptide are also provided. The present invention also encompasses the use of this DMTNFV1 TNF domain polypeptide as an immunogenic and/or antigenic epitope as described elsewhere herein.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1207 of SEQ ID NO:3, b is an integer between 15 to 1221, where both a and b correspond to the positions of nucleotide residues shown in SEQ ID NO:3, and where b is greater than or equal to a+14.

Features of the Polypeptide Encoded by Gene No:3

The polypeptide of this gene provided as SEQ ID NO:6 (FIGS. 3A–C), encoded by the polynucleotide sequence according to SEQ ID NO:5 (FIGS. 3A–C), and/or encoded by the polynucleotide contained within the clone, DmTNFv2, has significant homology at the nucleotide and amino acid level to the human osteoprotegerin protein (Osteoprotegerin; Genbank Accession No. gi|12643360; SEQ ID NO:7), the human hCD27 ligand protein (hCD27L; Genbank Accession No. gi|P32970; SEQ ID NO:55), the human CD30 ligand protein (hCD30L; Genbank Accession No. gi|P32971; SEQ ID NO:56); the human TRAIL protein (hTRAIL; Genbank Accession No. gi|P50591; SEQ ID NO:57); the human ectodysplasmin_A protein (hEctodysplasmin_A; Genbank Accession No. gi|Q92838; SEQ ID NO:8), and the mouse ectodysplasmin_A protein (mEctodysplasmin_A; Genbank Accession No. gi|NP_034229; SEQ ID NO:9). An alignment of the DmTNFv2 polypeptide with these proteins is provided in FIGS. 6A–S.

The DmTNFv2 polypeptide was determined to share 21.4% identity and 35.7% similarity with the human osteoprotegerin protein (Osteoprotegerin; Genbank Accession No. gi|12643360; SEQ ID NO:7), to share 12.5% identity and 37.5% similarity with the human hCD27 ligand protein (hCD27L; Genbank Accession No. gi|P32970; SEQ If) NO:55), to share 20% identity and 26.7% similarity with the human CD30 ligand protein (hCD30L; Genbank Accession No. gi|P32971; SEQ ID NO:56); to share 24.1% identity and 33.9% similarity with the human TRAIL protein (hTRAIL; Genbank Accession No. gi|P50591; SEQ ID NO:57); to share 22.4% identity and 29.1% similarity with the human ectodysplasmin_A protein (hEctodysplasmin_A; Genbank Accession No. gi|Q92838; SEQ ID NO:8), and to share 21.6% identity and 29.2% similarity with the mouse ectodysplasmin_A protein (mEctodysplasmin A; Genbank Accession No. gi|NP_034229; SEQ ID NO:9) as shown in FIG. 11.

Expression profiling designed to measure the steady state mRNA levels encoding the DmTNF polypeptide showed predominately high expression levels in Drosophila embryos, significantly in larvae, and to a lesser extent, in adult (as shown in FIG. 3).

Moreover, in situ hybridization of Drosophila embryos at various developmental stages indicated that DmTNF gene expression was upregulated in the dorsal region of the developing embryo (stage 4/5) at a time coincident with the activation of Rel activity in the ventral region only. Specifically, DmTNF was expressed only in areas where Rel proteins are not activated. The results, in conjunction with the results provided elsewhere herein, suggest DmTNF is negatively regulated by the Rel activation pathway in embryogenesis.

Based upon the observed homology, the polypeptide of the present invention may share at least some biological activity with tumor necrosis family members, specifically with CD27L, CD30L and TRAIL, and preferably with the tumor necrosis factor family members referenced elsewhere herein.

The DmTNFv2 polypeptide was determined to comprise a signal sequence from about amino acid 1 to about amino acid 52 of SEQ ID NO:6 (FIGS. 3A–C) according to the SPScan computer algorithm (Genetics Computer Group suite of programs). Based upon the predicted signal peptide cleavage site, the mature DmTNFv2 polypeptide is expected to be from about amino acid 53 to about amino acid 409 of SEQ ID NO:6 (FIGS. 3A–C). As this determination was based upon the prediction from a computer algorithm, the exact physiological cleavage site may vary, as discussed more particularly herein. In this context, the term "about" should be construed to mean 1, 2, 3, 4, 5, 6, 7, 8, 9, 10, 11, 12, 13, 14, 15, 16, 17, 18, 19, or 20 more amino acids in either the N- or C-terminal direction of the above referenced polypeptide. Polynucleotides encoding these polypeptides are also provided.

In addition to the mature polypeptide above, the polynucleotides encoding the mature polypeptide are also encompassed by the present invention. Specifically, from about nucleotide position 790 to about nucleotide position 1860 of SEQ ID NO:5 (FIGS. 3A–C).

Similarly, several members of the TNF family, such as, for example, CD27L, CD30L and TRAIL, in addition to the etodysplasin-A protein, are type II transmembrane proteins. Hydrophobicity plot analysis using Kyte-Doolittle Hydropathy algorithm suggests that DmTNFv2 is also a type II transmembrane protein (e.g., potentially secreted protein), with a short intracellular domain at the NH2 terminal of DmTNFv2 and a long extracellular domain at the COOH terminal of DmTNFv2 as shown in FIG. 7.

In terms of general utility of the novel DmTNFV2 of the present invention, gene expression of DmTNFv2 suggests it is important in immunomodulation and metabolic biology in Drosophila, and potentially humans. Biochemical pathways are highly conserved from Drosophila to man; therefore, studies in Drosophila are very relevant to human biology. Through tools common to Drosophila research the biological significance and biochemical pathways of DmTNFv2 can be elucidated. Loss of function mutations in DmTNFv2 will be identified and transgenic flies can be generated to overexpress DmTNFv2 and mutant forms in specific tissues. These types of experiments may be used to identify the DmTNFv2 receptor, its signaling pathway and the biological functions of DmTNFv2.

Similar to other receptor systems being investigated (e.g., CD40/CD40L, 4-1BB/4-1BBL, Fas/FasL) it is contemplated by the present invention that the interaction between the novel DmTNFv2 (or human homologues found using the novel DmTNFv2 of the present invention) and its receptor may serve as a novel target for immunosuppressive, anti-inflammatory and/or immunostimulatory drug development.

The present invention relates to the nucleic acid sequence or a fragment thereof (referred to herein as a "polynucleotide") of the novel DmTNFv2 as shown above (SEQ ID NO:5), as well as to the amino acid sequence of the DmTNFv2 (SEQ ID NO:6), and biologically active portions thereof.

The present invention further releases to a tumor necrosis factor molecule polypeptide, DmTNFv2 which has the deduced amino acid sequence as shown in SEQ ID NO:6, as well as fragments, analogs and derivatives of such polypeptide.

DmTNFv2 polynucleotide and polypeptides, including variants of fragments thereof, can be used for the generation of mutant phenotypes in animal models or in living cells. Preferably, such phenotypes are genetically modified to either express or misexpress the DmTNFv2 gene, for example using transposon mutagenesis, RNA interference, chemical mutagenesis, or other genetic techniques. As discussed elsewhere herein, the expression of the DmTNFv2 protein may be driven by a heterologous promoter that is tissue-specific, developmentally specific, or inducible, enabling the effects of the expression of mis-expression can be observed in specific tissues, at certain developmental stages, or at specified times, respectively. Such mutant phenotypes are useful for studying the regulation of DmTNFv2, and the use of DmTNFv2 as a drug target in an effort to identify potential therapeutic compounds. Due to the ability to carry out large scale, systemic genetic screens, the use of Drosophila has great utility for analyzing the expression and mis-expression of DmTNFv2, TNF proteins, and/or TNF homologs. Additionally, the DmTNFv2 pathway protein may be linked to one or more selectable markers that allows detection of expression. For example, the expression of the DmTNFv2 results in an identifiable phenotype.

DmTNFv2 polynucleotide and polypeptides, including variants or fragments thereof, are useful for screening molecules that modulate DmTNFv2, or the DmTNFv2 pathway.

In addition, DmTNFv2 polynucleotide and polypeptides, including variants or fragments thereof, are useful in the elucidation of biological pathways, particularly TNF pathways (Margolis, J. and Duyk, G. Nat Biotechnol. (1998)16: 311, Matthews D. and Kopcynski, J (2001) Drug Disc. Today 6: 141–149). DmTNFv2 polynucleotide and polypeptides including variants or fragments thereof, are useful for identifying other TNF family members.

The homology to the human osteoprotegerin ligand protein, combined with the observed expression in Drosophila embryos, suggests the DmTNFv2 polynucleotides and polypeptides of the present invention have uses which include treating, ameliorating, and/or preventing diseases and disorders related to aberrant osteoprotegerin ligand function. Moreover, the DmTNFv2 polynucleotides and polypeptides of the present invention may be useful for augmenting the ability of dendritic cells to stimulate naive t-cell proliferation, in regulating interaction between t cells and dendrictic cells modulating the regulation of the t cell-dependent immune response, in addition to, potentially enhancing bone-resorption in humoral hypercalcemia of malignancy, in animals, preferably humans. DmTNFv2 may also be useful in modulating immune responses, and/or ameliorating or preventing morphological aberrations in insects, preferably in flies, such as Drosophila.

In addition, the negative regulation of DmTNF by Rel strongly suggests DmTNF polynucleotides and polypeptides of the present invention have uses which include modulating the innate immune response in invertebrates, particularly flies, and most preferably in Drosophila. Moreover, the specific expression in embryos also suggests DmTNF polynucleotides and polypeptides of the present invention have uses which include modulating development and/or patterning during embryogenesis in invertebrates, particularly flies, and most preferably in Drosophila. p As noted above, the DmTNFv2 polypeptide was also determined to share significant homology with both the human and mouse ectodysplasmin_A protein. Mutations within ectodysplasin-A in mice has been shown in result in a Tabby phenotype (i.e., no sweat glands). Ectodysplasin-A has been shown to function in epithelial morphogenesis and promotes cell-matrix adhesion. In addition, mutations in the human ectodysplasmin-A has been directly implicated in X-linked anhidrotic (hypohidrotic) ectodermal dysplasia (Kere, J., et al., Nat. Genet. 13 (4), 409–416 (1996)). This disorder results in sparse hair (artrichosis or hypotrichosis), abnormal or missing teeth and the inability to sweat due to the absence of sweat glands in humans.

Therefore, DmTNFv2 polynucleotides and polypeptides, including fragments and /or antagonists thereof, may have uses which include modulating epithelial morphogenesis, cell-matrix adhesion, in flies, preferably Drosophila, and potentially in other organisms as well, preferably mammals, such as humans, mice, and rats. Moreover, DmTNFv2 polypeptides and polypeptides, including fragments and/or antagonists thereof, may have uses which include treating, ameliorating, and/or preventing X-linked anhidrotic (hypohidrotic) ectodermal dysplasia, including X-linked anhidrotic (hypohidrotic) ectodermal dysplasia-like disorders, such as sparse hair, abnormal or missing teeth, and sweat gland aberrations, in animals, preferably insects, and potentially in humans.

In preferred embodiments, the following N-terminal DmTNFv2 deletion polypeptides are encompassed by the present invention: M1-V409, T2-V409, A3-V409, E4-V409, T5-V409, P8-V409, L6-V409, K7-V409, F9-V409, I10-V409, T11-V409, P12-V409, T13-V409, S14-V409, A15-V409, N16-V409, D17-V409, D18-V409, G19-V409, F20-V409, P21-V409, A22-V409, K23-V409, A24-V409, T25-V409, S26-V409, T27-V409, A28-V409, T29-V409, A30-V409, Q31-V409, R32-V409, R33-V409, T34-V409, R35-V409, Q36-V409, L37-V409, I38-V409, P39-V409, L40-V409, V41-V409, L42-V409, G43-V409, F44-V409, I45-V409, G46-V409, L47-V409, G48-V409, L49-V409, V50-V409, V51-V409, A52-V409, I53-V409, L54-V409, A55-V409, L56-V409, T57-V409, I58-V409, W59-V409, Q60-V409, T61-V409, T62-V409, R63-V409, V64-V409, S65-V409, H66-V409, L67-V409, D68-V409, K69-V409, E70-V409, L71-V409, K72-V409, S73-V409, L74-V409, K75-V409, R76-V409, V77-V409, V78-V409, D79-V409, N80-V409, L81-V409, Q82-V409, Q83-V409, R84-V409, L85-V409, G86-V409, I87-V409, N88-V409, Y89-V409, L90-V409, D91-V409, E92-V409, F93-V409, D94-V409, E95-V409, F96-V409, Q97-V409, K98-V409, E99-V409, Y100-V409, E101-V409, N102-V409, A103-V409, L104-V409, I105-V409, D106-V409, Y107-V409, P108-V409, K109-V409, K110-V409, V111-V409, D112-V409, G113-V409, L114-V409, T115-V409, D116-V409, E117-V409, E118-V409, D119-V409, D120-V409, D121-V409, D122-V409, G123-V409, D124-V409, G125-V409, L126-V409, D127-V409, S128-V409, I129-V409, A130-V409, D131-V409, D132-V409, E133-V409, D134-V409, D135-V409, D136-V409, V137-V409, S138-V409, Y139-V409, S140-V409, S141-V409, V142-V409, D143-V409, D144-V409, V145-V409, G146-V409, A147-V409, D148-V409, Y149-V409, E150-V409, D151-V409, Y152-V409, T153-V409, D154-V409, M155-V409, L156-V409, N157-V409, K158-V409, L159-V409, N160-V409, N161-V409, A162-V409, H163-V409, T164-V409, G165-V409, T166-V409, T167-V409, P168-V409, T169-V409, S170-V409, E171-V409, T172-V409, T173-V409, A174-V409, E175-V409, G176-V409, E177-V409, G178-V409, E179-V409, T180-V409, D181-V409, S182-V409, A183-V409, S184-V409, S185-V409, A186-V409, S187-V409, N188-V409, D189-V409, D190-V409, N191-V409, V192-V409, F193-V409, D194-V409, D195-V409, F196-V409, T197-V409, S198-V409, Y199-V409, N200-V409, A201-V409, H202-V409, K203-V409, K204-V409, K205-V409, Q206-V409, E207-V409, R208-V409, K209-V409, S210-V409, R211-V409, S212-V409, I213-V409, A214-V409, D215-V409, V216-V409, R217-V409, N218-V409, E219-V409, E220-V409, Q221-V409, N222-V409, I223-V409, Q224-V409, G225-V409, N226-V409, H227-V409, T228-V409, E229-V409, L230-V409, Q231-V409, E232-V409, K233-V409, S234-V409, S235-V409, N236-V409, E237-V409, A238-V409, T239-V409, S240-V409, K241-V409, E242-V409, S243-V409, P244-V409, A245-V409, P246-V409, L247-V409, H248-V409, H249-V409, R250-V409, R251-V409, R252-V409, M253-V409, H254-V409, S255-V409, R256-V409, H257-V409, R258-V409, H259-V409, L260-V409, L261-V409, V262-V409, R263-V409, K264-V409, A265-V409, R266-V409, S267-V409, E268-V409, D269-V409, S270-V409, R271-V409, P272-V409, A273-V409, A274-V409, H275-V409, F276-V409, H277-V409, L278-V409, S279-V409, S280-V409, R281-V409, R282-V409, R283-V409, H284-V409, Q285-V409, G286-V409, S287-V409, M288-V409, G289-V409, Y290-V409, H291-V409, G292-V409, D293-V409, M294-V409, Y295-V409, I296-V409, G297-V409, N298-V409, D299-V409, N300-V409, E301-V409, R302-V409, N303-V409, S304-V409, Y305-V409, Q306-V409, G307-V409, H308-V409, F309-V409, Q310-V409, T311-V409, R312-V409, D313-V409, G314-V409, V315-V409, L316-V409, T317-V409, V318-V409, T319-V409, N320-V409, T321-V409, G322-V409, L323-V409, Y324-V409, Y325-V409, V326-V409, Y327-V409, A328-V409, Q329-V409, I330-V409, C331-V409, Y332-V409, N333-V409, N334-V409, S335-V409, H336-V409, D337-V409, Q338-V409, N339-V409, G340-V409, F341-V409, I342-V409, V343-V409, F344-V409, Q345-V409, G346-V409, D347-V409, T348-V409, P349-V409, F350-V409, L351-V409, Q352-V409, C353-V409, L354-V409, N355-V409, T356-V409, V357-V409, P358-V409, T359-V409, N360-V409, M361-V409, P362-V409, H363-V409, K364-V409, V365-V409, H366-V409, T367-V409, C368-V409, H369- encoding these polypeptides are also provided. The present invention also encompasses the use of these N-terminal DmTNFv2 deletion polypeptides as immunogenic and/or antigenic epitopes as described elsewhere herein.

In preferred embodiments, the following C-terminal DmTNFv2 deletion polypeptides are encompassed by the present invention: M1-V409, M1-408, M1-F407, M1-I406, M1-G405, M1-F404, M1-Y403, M1-S402, M1-R401, M1-N400, M1-N399, M1-G398, M1-E397, M1-R396, M1-L395, M1-V394, M1-A393, M1-N392, M1-R391, M1-D390, M1-N389, M1-H388, M1-I387, M1-D386, M1-K385, M1-L384, M1-H383, M1-I382, M1-R381, M1-E380, M1-N379, M1-R378, M1-E377, M1-L376, M1-H375, M1-I374, M1-L373, M1-G372, M1-S371, M1-T370, M1-H369, M1-C368, M1-T367, M1-H366, M1-V365, M1-K364, M1-H363, M1-P362, M1-M361, M1-N360, M1-T359, M1-P358, M1-V357, M1-T356, M1-N355, M1-L354, M1-C353, M1-Q352, M1-L351, M1-F350, M1-P349, M1-T348, M1-D347, M1-G346, M1-Q345, M1-F344, M1-V343, M1-I342, M1-F341, M1-G340, M1-N339, M1-Q338, M1-D337, M1-H336, M1-S335, M1-N334, M1-N333, M1-Y332, M1-C331, M1-I330, M1-Q329, M1-A328, M1-Y327, M1-V326, M1-Y325, M1-Y324, M1-L323, M1-G322, M1-T321, M1-N320, M1-T319, M1-V318, M1-T317, M1-L316, M1-V315, M1-G314, M1-D313, M1-R312, M1-T311, M1-Q310, M1-F309, M1-H308, M1-G307, M1-Q306, M1-Y305, M1-S304, M1-N303, M1-R302, M1-E301, M1-N300, M1-D299, M1-N298, M1-G297, M1-I296, M1-Y295, M1-M294, M1-D293, M1-G292, M1-H291, M1-Y290, M1-G289, M1-M288, M1-S287, M1-G286, M1-Q285, M1-H284, M1-R283, M1-R282, M1-R281, M1-S280, M1-S279, M1-L278, M1-H277, M1-F276, M1-H275, M1-A274, M1-A273, M1-P272, M1-R271, M1-S270, M1-D269, M1-E268, M1-S267, M1-R266, M1-A265, M1-K264, M1-R263, M1-V262, M1-L261, M1-L260, M1-H259, M1-R258, M1-H257, M1-R256, M1-S255, M1-H254, M1-M253, M1-R252, M1-R251, M1-R250, M1-H249, M1-H248, M1-L247, M1-P246, M1-A245, M1-P244, M1-S243, M1-E242, M1-K241, M1-S240, M1-T239, M1-A238, M1-E237, M1-N236, M1-S235, M1-S234, M1-K233, M1-E232, M1-Q231, M1-L230, M1-E229, M1-T228, M1-H227, M1-N226, M1-G225, M1-Q224, M1-I223, M1-N222, M1-Q221, M1-E220, M1-E219, M1-N218, M1-R217, M1-V216, M1-D215, M1-A214, M1-I213, M1-S212, M1-R211, M1-S210, M1-K209, M1-R208, M1-E207, M1-Q206, M1-K205, M1-K204, M1-K203, M1-H202, M1-A201, M1-N200, M1-Y199, M1-S198, M1-T197, M1-F196, M1-D195, M1-D194, M1-F193, M1-V192, M1-N191, M1-D190, M1-D189, M1-N188, M1-S187, M1-A186, M1-S185, M1-A183, M1-S182, M1-D181, M1-T180, M1-E179, M1-G178, M1-E177, M1-G176, M1-E175, M1-A174, M1-T173, M1-T172, M1-E171, M1-S170, M1-T169, M1-P168, M1-T167, M1-T166, M1-G165, M1-T164, M1-H163, M1-A162, M1-N161, M1-L159, M1-K158, M1-N157, M1-L156, M1-M155, M1-D154, M1-T153, M1-Y152, M1-D151, M1-E150, M1-Y149, M1-D148, M1-A147, M1-G146, M1-V145, M1-D144, M1-D143, M1-V142, M1-S141, M1-S140, M1-Y139, M1-S138, M1-V137, M1-D136, M1-D135, M1-D134, M1-E133, M1-D132, M1-D131, M1-A130, M1-I129, M1-S128, M1-D127, M1-L126, M1-G125, M1-D124, M1-G123, M1-D122, M1-D121, M1-D120, M1-D119, M1-E118, M1-E117, M1-D116, M1-T115, M1-L114, M1-G113, M1-D112, M1-V111, M1-K110, M1-K109, M1-P108, M1-Y107, M1-D106, M1-I105, M1-L104, M1-A103, M1-N102, M1-E101, M1-Y100, M1-E99, M1-K98, M1-Q97, M1-F96, M1-E95, M1-D94, M1-F93, M1-E92, M1-D91, M1-L90, M1-Y89, M1-N88, M1-I87, M1-G86, M1-L85, M1-R84, M1-Q83, M1-Q82, M1-L81, M1-N80, M1-D79, M1-V78, M1-V77, M1-R76, M1-K75, M1-L74, M1-S73, M1-K72, M1-L71, M1-E70, M1-K69, M1-D68, M1-L67, M1-H66, M1-S65, M1-V64, M1-R63, M1-T62, M1-T61, M1-Q60, M1-W59, M1-I58, M1-T57, M1-L56, M1-A55, M1-L54, M1-I53, M1-A52, M1-V51, M1-V50, M1-L49, M1-G48, M1-L47, M1-G46, M1-I45, M1-F44, M1-G43, M1-L42, M1-V41, M1-L40, M1-P39, M1-I38, M1-L37, M1-Q36, M1-R35, M1-T34, M1-R33, M1-R32, M1-Q31, M1-A30, M1-T29, M1-A28, M1-T27, M1-S26, M1-T25, M1-A24, M1-K23, M1-A22, M1-P21, M1-F20, M1-G19, M1-D18, M1-D17, M1-N16, M1-A15, M1-S14, M1-T13, M1-P12, M1-T11, M1-I10, M1-F9, M1-P8, and/or M1-K7 of SEQ ID NO:6. Polynucleotide sequences encoding these polypeptides are also provided. The present invention also encompasses the use of these C-terminal DmTNFv2 deletion polypeptides as immunogenic and/or antigenic epitopes as described elsewhere herein.

Alternatively, preferred polypeptides of the present invention may comprise polypeptide sequences corresponding to, for example, internal regions of the DmTNFv2 polypeptide (e.g., any combination of both N- and C- terminal DmT- NFv2 polypeptide deletions) of SEQ ID NO:6. For example, internal regions could be defined by the equation: amino acid NX to amino acid CX, wherein NX refers to any N-terminal deletion polypeptide amino acid of DmTNFv2 (SEQ ID NO:6), and where CX refers to any C-terminal deletion polypeptide amino acid of DmTNFv2 (SEQ ID NO:6). Polynucleotides encoding these polypeptides are also provided. The present invention also encompasses the use of these polypeptides as an immunogenic and/or antigenic epitope as described elsewhere herein.

In preferred embodiments, the following DmTNFv2 TNF domain amino acid substitutions are encompassed by the present invention: wherein L316 is substituted with either an A, C, D, E, F, G, H, I, K, M, N, P, Q, R, S, T, V, W, or Y; wherein T317 is substituted with either an A, C, D, E, F, G, H, I, K, L, M, N, P, Q, R, S, V, W, or Y; wherein V318 is substituted with either an A, C, D, E, F, G, H, I, K, L, M, N, P, Q, R, S, T, W, or Y; wherein T319 is substituted with either an A, C, D, E, F, G, H, I, K, L, M, N, P, Q, R, S, V, W, or Y; wherein N320 is substituted with either an A, C, D, E, F, G, H, I, K, L, M, P, Q, R, S, T, V, W, or Y; wherein T321 is substituted with either an A, C, D, E, F, G, H, I, K, L, M, N, P, Q, R, S, V, W, or Y; wherein G322 is substituted with either an A, C, D, E, F, H, I, K, L, M, N, P, Q, R, S, T, V, W, or Y; wherein L323 is substituted with either an A, C, D, E, F, G, H, I, K, L, M, N, P, Q, R, S, T, V, W, or Y; wherein Y324 is substituted with either an A, C, D, E, F, G, H, I, K, L, M, N, P, Q, R, S, T, V, or W; wherein Y325 is substituted with either an A, C, D, E, F, G, H, I, K, L, M, N, P, Q, R, S, T, V, or W; wherein V326 is substituted with either an A, C, D, E, F, G, H, I, K, L, M, N, P, Q, R, S, T, V, W, or Y; wherein Y327 is substituted with either an A, C, D, E, F, G, H, I, K, L, M, N, P, Q, R, S, T, V, or W; wherein A328 is substituted with either an C, D, E, F, G, H, I, K, L, M, N, P, Q, R, S, T, V, W, or Y; wherein Q329 is substituted with either an A, C, D, E, F, G, H, I, K, L, M, N, P, R, S, T, V, W, or Y; wherein I330 is substituted with either an A, C, D, E, F, G, H, I, K, L, M, N, P, Q, R, S, T, V, W, or Y; wherein C331 is substituted with either an A, D, E, F, G, H, I, K, L, M, N, P, Q, R, S, T, V, W, or Y; and/or wherein Y332 is substituted with either an A, C, D, E, F, G, H, I, K, L, M, N, P, Q, R, S, T, V, or W; of SEQ ID NO:6, in addition to any combination thereof. The present invention also encompasses the use of these DmTNFv2 TNF domain amino acid substituted polypeptides as immunogenic and/or antigenic epitopes as described elsewhere herein.

In preferred embodiments, the following DmTNFv2 TNF domain conservative amino acid substitutions are encompassed by the present invention; wherein L316 is substituted with either an A, I, or V; wherein T317 is substituted with an A, G, M, or S; wherein V318 is substituted with either an A, I, or L; wherein T319 is substituted with either an A, G, M, or S; wherein N320 is substituted with a Q; wherein T321 is substituted with either an A, G, M, or S; wherein G322 is substituted with either an A, M, S, or T; wherein L323 is substituted with either an A, I, or V; wherein Y324 is either an F, or W; wherein Y325 is either an F, or W; wherein V326 is substituted with either an A, I, or L; wherein Y327 is either an F, or W; wherein A328 is substituted with either a G, I, L, M, S, T, or V; wherein Q329 is substituted with a N; wherein I330 is substituted with either an A, V, or L; wherein C331 is a C; and/or wherein Y332 is either an F, or W of SEQ ID NO:6 in addition to any combination thereof. Other suitable substitutions within the DmTNFv2 TNF domain are encompassed by the present invention and are referenced elsewhere herein. The present invention also encompasses the use of these DmTNFv2 TNF domain conservative amino acid substituted polypeptides as immunogenic and/or antigenic epitopes as described elsewhere herein.

The DmTNFv2 polypeptide has been shown to comprise three glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-[P]-[ST]-{P}, wherein N represents the glycosylation site. However, it is well known that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention: QNIQGNHTELQEKS (SEQ ID NO:54), AQICYNNSHDQNGF (SEQ ID NO:55), and/or LREGNNRSYFGIFK (SEQ ID NO:56). Polynucleotides encoding these polypeptides are also provided. The present invention also encompasses the use of these DmTNFv2 asparagine glycosylation site polypeptides as immunogenic and/or antigenic epitopes as described elsewhere herein.

DMTNFV2 polypeptides of the present invention were determined to comprise several phosphorylation sites based upon the Motif algorithm (Genetics Computer Group, Inc.). The phosphorylation of such sites may regulate some biological activity of the DMTNFV2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the DMTNFV2 polypeptide to associate with other potassium channel alpha subunits, beta subunits, or its ability to modulate potassium channel function.

The DMTNFV2 polypeptide was predicted to comprise six PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1989); which are hereby incorporated by reference herein.

In preferred embodiments, the following PKC phosphorylation site polypeptides are encompassed by the present invention: MTAETLKPFITP (SEQ ID NO:57), LTTWQTTRVSHLD (SEQ ID NO:58), DKELKSLKRVVDN (SEQ ID NO:59), SSNEATSKESPAP (SEQ ID NO:60), AHFHLSSRRRHQG (SEQ ID NO:61), and/or HFHLSSRRRHQGS (SEQ ID NO:62). Polynucleotides encoding these polypeptides are also provided. The present invention also encompasses the use of these DMTNFV2 PKC phosphorylation site polypeptide as immunogenic and/or antigenic epitopes as described elsewhere herein.

Consistent with the DmTNFv2 polypeptide representing a TNF superfamily member, the DMTNFV2 polypeptide was predicted to comprise a TNF family domain using the Motif algorithm (Genetics Computer Group, Inc.). The following cytokines can be grouped into a family on the basis of sequence, functional, and structural similarities: Tumor Necrosis Factor (TNF) (also known as cachectin or TNF-alpha), is a cytokine which has a wide variety of functions. It can cause cytolysis of certain tumor cell lines, it is involved in the induction of cachexia, it is a potent pyrogen, causing fever by direct action or by stimulation of interleukin-1 secretion, finally, it can stimulate cell proliferation and induce cell differentiation under certain conditions; Lymphotoxin-alpha (LT-alpha) and lymphotoxin-beta (LT-beta), two related cytokines produced by lymphocytes and which are cytotoxic for a wide range of tumor cells in vitro and in vivo; T cell antigen gp39 (CD40L), a cytokine which seems to be important in B-cell development and activation; CD27L, a cytokine which plays a role in T-cell activation. It induces the proliferation of costimulated T cells and enhances the generation of cytolytic T cells; CD30L, a cytokine which induces proliferation of T cells; FASL, a cytokine involved in cell death; 4-1BBL, an inducible T cell surface molecule that contributes to T-cell stimulation; OX40L, a cytokine that co-stimulates T cell proliferation and cytokine production; TNF-related apoptosis inducing ligand (TRAIL), a cytokine that induces apoptosis; TNF-alpha is synthesized as a type II membrane protein which then undergoes post-translational cleavage liberating the extracellular domain. CD27L, CD30L, CD40L, FASL, LT-beta, 4-1BBL and TRAIL also appear to be type II membrane proteins. LT-alpha is a secreted protein. All these cytokines seem to form homotrimeric (or heterotrimeric in the case of LT-alpha;beta) complexes that are recognized by their specific receptors.

The TNF domain represents the most conserved region within the TNF family. This domain is located in a beta-strand in the central section of these proteins and has the following consensus pattern: [LV]-x-[LIVM]-x(3)-G-[LIVMF]-Y-[LIVMFY](2)-x(2)-[QEKHL]-[LIVMGT]-x-[LIVMFY], wherein "x" is equals any amino acid.

Additional information related to the TNF domain and/or TNF domain containing proteins may be found by reference to the following publications which are hereby incorporated herein by reference in their entirety: Peitsch M. C., Jongeneel C. V., Int. Immunol. 5:233–238(1993); Farrah T., Smith C. A., Nature 358:256–26(1992); Bazan J. F., Curr. Biol. 3:603–606(1993); Beutler B., Cerami A., Biochemistry, 27:7575–7582(1988); Vilcek J., Lee T. H., J. Biol. Chem. 266:7313–7316(1991); Browning J. L., Ngam-Ek A., Lawton P., Demarinis J., Tizard R., Chow E. P., Hession C., O'Brine-Greco B., Foley S. F., Ware C. F., Cell 72:847–856 (1993); Suda T., Takahashi T., Golstein P., Nagata S, Cell 75:1169–1178(1993); Baum P. R., Gayle R. B. III, Ramsdell F., Srinivasan S., Sorensen R. A., Watson M. L., Seldin M. F., Baker E., Sutherland G. R., Clifford K. N., Alderson M. R., Goodwin R. G., Fanslow W. C., EMBO J. 13:3992–4001 (1994); and Wiley S. R., Schooley K., Smolak P. J., Din W. S., Huang C.-P., Nicholl J. K., Sutherland G. R., Davis-Smith T., Rauch C., Smith C. A., Goodwin R. G., Immunity 3:673–682(1995).

In preferred embodiments, the following TNF domain polypeptide is encompassed by the present invention: TRDGVLTVTNTGLYYVYAQICYNNSHD (SEQ ID NO:63). Polynucleotides encoding this polypeptide is also provided. The present invention also encompasses the use of this DMTNFV2 TNF domain polypeptide as an immunogenic and/or antigenic epitope as described elsewhere herein.

Many polynucleotide sequences, such as EST sequences, are publicly available and accessible through sequence databases. Some of these sequences are related to SEQ ID NO:b 5and may have been publicly available prior to conception of the present invention. Preferably, such related polynucleotides are specifically excluded from the scope of the present invention. To list very related sequence would be cumbersome. Accordingly, preferably excluded from the present invention are one or more polynucleotides comprising a nucleotide sequence described by the general formula of a–b, where a is any integer between 1 to 2134 of SEQ ID NO:5, b is an integer between 15 to 2148, where both a and b correspond to the positions of nucleotide residues shown in SEQ ID NO:5, and where b is greater than or equal to a+14.

TABLE I

| Gene No. | Clone ID | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|
| 1. | DmTNF | XXXX | 1 | 2166 | 652 | 1878 | 2 | 409 |
| 2. | DmTNFv1 | XXXX | 3 | 1221 | 1 | 1218 | 4 | 406 |
| 3. | DmTNFv2 | pOT2 | 5 | 2148 | 634 | 1860 | 6 | 409 |

Table 1 summarizes the information corresponding to each "Gene No." described above. The nucleotide sequence identified as "NT SEQ ID NO:X" represents the nucleic acid sequence of the gene identified as "Clone ID".

"Total NT Seq. Of Clone" refers to the total number of nucleotides in the clone contig identified by "Gene No." The clone may contain all or most of the sequence of SEQ ID NO:X. The nucleotide position of SEQ ID NO:X of the putative start codon (methionine) is identified as "5' NT of Start Codon of ORF." As some of these sequences were identified and determined by bioinformatic methods, a physical clone may or may not exist (DmTNF and DmTNFv1). In such circumstances, where a clone exists for a variant of such a clone (DmTNFv2), the variant may be modified using known mutagenesis techniques to arrive at a clone that corresponds to said sequence (DmTNF and DMTNFV1).

The translated amino acid sequence, beginning with the methionine, is identified as "AA SEQ ID NO:Y," although other reading frames can also be easily translated using known molecular biology techniques. The polypeptide produced by these alternative open reading frames are specifically contemplated by the present invention.

The total number of amino acids within the open reading frame of SEQ ID NO:Y is identified a s"Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acids sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides the generated nucleotide sequence identified as SEQ ID NO:X and the predicted translated amino acid sequence identified as SEQ ID NO:Y.

The present invention also relates to the genes corresponding to SEQ ID NO:X, or SEQ ID NO:Y. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologs of genes corresponding to SEQ ID NO:X, SEQ ID NO:Y, or relying on the sequence from the sequences disclosed. For example, allelic variants and/or species homologs may be isolated and identified by making suitable probes or primers which correspond to the 5',3', or internal regions of the sequences provided herein and screening a suitable nucleic acid source for allelic variants and/or the desires homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:X. The present invention also provides a polypeptide comprising, or alternatively consisting of, the sequence identified as SEQ ID NO. The present invention also provide polynucleotides encoding a polypeptide comprising, or alternatively consisting of the polypeptide sequence of SEQ ID NO:Y.

Preferably, the present invention is directed to a polynucleotide comprising, or alternatively consisting of, the sequence identified as SEQ ID NO:X: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:X, and/or the nucleic acid sequence encoding the sequence disclosed as SEQ ID NO:Y.

The present invention also encompasses polynucleotide capable of hybridizing, preferably under reduced stringency conditions, more preferably under stringent conditions, and most preferably under highly stringent conditions, to polynucleotides described herein. Examples of stringency conditions are shown in Table 2 below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 2

| Stringency Condition | Polynucleotide Hybrid± | Hybrid Length (bp) ‡ | Hybridization Temperature and Buffer† | Wash Temperature and Buffer† |
|---|---|---|---|---|
| A | DNA:DNA | > or equal to 50 | 65° C.; 1xSSC - or –42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC - or –45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC - or –50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC - or –45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC - or –45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC - or –40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC - or –40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC - or –42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC - or –45° C.; 6xSSC, 50% formamide | 60° C.; 2xSSC |
| R | RNA:RNA | <50 | Tr*; 4xSSC | Tr*; 4xSSC |

‡: The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., CLUSTALW, GAP, etc).
†: SSPE (1xSSPE is 0.15 M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hybridizations and washes may additionally include 5X Denhardt's reagent, .5–1.0% SDS, 100 ug/ml denatured, fragmented salmon sperm DNA, 0.5% sodium pyrophosphate, and up to 50% formamide.
*Tb – Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6($\log_{10}$[Na+]) + 0.41(% G + C) – (600/N), where N is the number of bases in the hybrid, and [Na+] is the concentration of sodium ions in the hybridization buffer ([NA+] for 1xSSC = .165 M).
±: The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology 1995, F. M., Ausubel et al., eds, John Wiley and Sons, Inc., sections 2.10 and 6.3–6.4; which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, N.Y., 1989; Ehrlich et al., Science, 252:1643–1650, (1991); and "PCR Protocols, A Guide to Methods and Applications", Eds., Innis et al., Academic Press, New York, (1990).

Signal Sequences

The present invention also encompasses mature forms of the polypeptide comprising, or alternatively consisting of, the polypeptide sequence of SEQ ID NO:2, SEQ ID NO:4, SEQ ID NO:6, the polypeptide encoded by the polynucleotide described as SEQ ID NO:1, SEQ ID NO:3, and/or SEQ ID NO:5. The present invention also encompasses polynucleotides encoding mature forms of the present invention, such as, for example the polynucleotide sequence of SEQ ID NO:1, SEQ ID NO:3, and/or SEQ ID NO:6.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues –13 to +2, where +1 indicates the amino terminus of the secreted protein. The accuracy of predicting the cleavage points of known mammalian secretory proteins for each of these methods is in the range of 75–80% (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998;6:122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one or ordinary skill would appreciate, however, cleavage site sometimes vary from organism to organism and cannot be predicted with absolute certainty. Accordingly, the polypeptide of the present invention may contain a signal sequence. Polypeptides of the invention which comprise a signal sequence have a N-terminus beginning within 5 residues (i.e.,+ or –5 residues, or preferably at the –5, –4, –3, –2, –1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1, SEQ ID NO:3, and/or SEQ ID NO:6, in a mammalian cell (e.g., COS cells, as described below). These polypeptides, and the polynucleotides encoding such polypeptides, are contemplated by the present invention.

DmTNF Variants and Fragments

The high degree of structural homology in the presumptive extracellular TNF domain has important implications for engineering derivative (e. g. mutant) forms of these DmTNF genes for tests of function in vitro and in vivo, and for genetic dissection or manipulation of the DmTNF pathway in transgenic insects or insect cell lines. Soluble forms of human DmTNF have been generated to identify the relevant TNF receptor, signaling pathways and biological function (see Example 6). Soluble mutant forms are extremely useful for determining the effects of DmTNF in assays of interest. Thus, forms of DmTNF that include only the extracellular portion (e.g., mature form) and not the transmembrane region (e.g., signal sequence) can be generated based upon extensive characterization of mammalian TNFs, and are thus likely to result in soluble forms of DmTNF proteins.

The fragment or derivative of any of the DmTNF proteins is preferably "functionally active" meaning that the DmTNF protein derivative or fragment exhibits one or more functional activities associated with a full-length wild-type DmTNF protein comprising the amino acid sequence of any of SEQ ID NO: 2, 4, or 6. As one example, a fragment or derivative may have antigenicity such that it can be used in immunoassays, for immunization, for inhibition of DmTNF activity, etc., as discussed further below regarding generation of antibodies to DmTNF proteins. Preferably, a functionally active DmTNF fragment or derivative is one that displays one or more biological activities associated with DmTNF proteins such as regulation of immune response (Locksley et al. (2001) Cell: 487:501). The functional activity of DmTNF proteins, derivatives and fragments can be assayed by various methods known to one skilled in the art (Current Protocols in Protein Science (1998) Coligan et al. etds., John Wiley & Sons, Inc., Somerset.

Analogs of the novel DmTNF of the present invention are also within the scope of the present invention. Analogs can differ from the naturally occurring DmTNF of the present invention in amino acid sequence or in ways that do not involve sequence, or both. Non-sequence modifications include in vivo and in vitro chemical derivatization of the DmTNF of the present invention. Non-sequence modifications include changes in acetylation, methylation, phosphorylation, carboxylation, or glycosylation.

Preferred analogs include the novel DmTNF of the present invention (or biologically active fragments thereof) whose sequences differ from the wild-type sequence by one or more conservative amino acid substitutions or by one or more non-conservative amino acid substitutions, deletions or insertions which do not abolish the biological activity of the DmTNF of the present invention. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activ-

TABLE III

Conservative Amino Acid Substitutions

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, B-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4,or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

The present invention encompasses polypeptide variants. Such variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5 or 1–2 amino acids are substituted, deleted, or added in any combination are also ity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1A. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein functions. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The present invention also encompasses "humanized" forms of the DmTNF polypeptides. Another type of derivative of the subject nucleic acid sequences includes the corresponding humanized sequences. A humanized nucleic acid sequence is one in which one or more codons has been substituted with a codon that is more commonly used in human genes. Preferably, a sufficient number of codons have been substituted such that a higher level expression is achieved in mammalian cells than what would otherwise be achieved without the substitutions. Codons that are more commonly used in human genes are known (Wada et al., Nucleic Acids Research (1990) 18 (Suppl.): 2367–2411). Also, a detailed discussion of the humanization of nucleic acid sequences is provided in U.S. Pat. No. 5,874,304 to Zolotukhin et al. Similarly, other nucleic acid derivatives can be generated with codon usage optimized for expression in other organisms, such as yeasts, bacteria, and plants, where it is desired to engineer the expression of DmTNF pathway proteins by using specific codons chosen according to the preferred codons used in highly expressed genes in each organism.

Fragments of the DmTNF of the present invention are also within the scope of Applicant's invention. Fragments of the protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Digestion with "end-nibbling" endonucleases can thus generate DNA's which encode an array of fragments. DNA's which encode fragments of the DmTNF protein can also be generated by random shearing, restriction digestion or a combination of the above-discussed methods.

Fragments can also be chemically synthesized using techniques known in the art such as conventional Merrifield solid phase f-Moc or t-Boc chemistry.

Amino acid sequence variants of the DmTNF protein of the present invention can be prepared by random mutagenesis of DNA which encodes a protein or a particular domain or region of the protein. Useful methods are known in the art, e.g., PCR mutagenesis and saturation mutagenesis. A library of random amino acid sequence variants can also be generated by the synthesis of a set of degenerate oligonucleotides sequences, a process known and practiced by those skilled in the art.

Non-random or directed mutagenesis techniques can be used to provide specific sequences or mutations in specific regions. These techniques can be used to create variants which include, e.g., deletions, insertions, or substitutions of residues of the known amino acid sequence of the DmTNF protein of the present invention. The sites for mutation can be modified individually or in series, e.g., by (1) substituting first with conserved amino acids then with more radical choices depending upon results achieved; (2) deleting the target residue; or (3) inserting residues of the same or a different class (e.g., hydrophobic or hydrophilic) adjacent to the located site, or a combination of options (1)–(3). Alanine scanning mutagenesis is a useful method for identification of certain functional residues or regions of a desired protein that are preferred locations or domains for mutagenesis. Oligonucleotide-mediated mutagenesis, cassette mutagenesis, and combinatorial mutagenesis are useful methods known to those skilled in the art for preparing substitution, deletion, and insertion variants of DNA.

Characterization of DmTNF Polypeptides

TNF molecules have been implicated in playing a role in many cellular activities including cell death and proliferation (reviewed by Ashkenazi, A and Dixit, V M. (1998) Science 281: 1305–1308) A variety of methods may be used to examine whether the DmTNF proteins of the present invention also modulate apoptosis activity. One method is the terminal deoxynucleotidyl transferase-mediated digoxigenin-11-dUTP nick end labeling (TUNEL) assay which measures the nuclear DNA fragmentation characteristic of apoptosis (Lazebnik et al., Nature (1994) 371: 346–347: White et al. Science (1994) 264: 677–683). Additionally, commercial kits can be used for detection of apoptosis (ApoAlertO available from Clontech (Palo Alto, Calif.).

Apoptosis may also be assayed by a variety of staining methods. Acridine orange can be used to detect apoptosis in cultured cells (Lucas et al. Blood (1998) 15: 4730–41) and in intact Drosophila tissues, which can also be stained with Nile Blue (Abrams et al., Development (1993) 117: 29–43). Another assay that can be used to detect DNA laddering employs ethidium bromide staining and electrophoresis of DNA on an agarose gel (Civielli et al., Int. J. Cancer (1995) 27: 673–679: Young J. Biol. Chem. (1998) 273: 25198–25202).

Proliferating cells may be identified by bromodeoxyuhdine (BRDU) incorporation into cells undergoing DNA synthesis and detection by an anti-BRDU antibody (Hoshino et al., Int. J. Cancer (1986) 38: 369; Campana et al., J. Immunol. Meth. (1988) 107: 79). This assay can be used to reproducibly identify S-phase cells in Drosophila embryos (Edgar and O'Farrell, Cell (1990) 62: 469–480) and invaginal discs (Secombe et al. Genetics (1998) 149: 1867–1882). S-phase DNA syntheses can also be quantified by measuring [3H]-thymidine incorporation using a scintillation counter (Chen. Oncogene (1996) 13: 1395–403; Jeoung, J. Biol. Chem. (1995) 270:18367–73). Cell proliferation may be measured by counting samples of a cell population over time for example using a hemacytometer and Trypan-blue staining.

The DNA content and/or mitotic index of the cells may be measured based on the DNA ploidy value of the cell using a variety of methods known in the art such as a propidum iodide assay (Turner et (il. Prostate (1998) 34: 175–81) or Feulgen staining using a computerized microdensitometry staining system (Bacus, Am. J. Pathol. (1989) 135: 783–92).

The effect of DmTNF overexpression or loss-of-function on Drosophila cell proliferation can be assayed in vivo using an assay in which clones of cells with altered gene expression are generated in the developing wing disc of Drosophila (Neufeld et al. Cell (1998) 93: 1183–93). The clones coexpress GFP which allows the size and DNA content of the mutant and wild-type cells from dissociated discs to be compared by FACS analysis.

Generation and Genetic Analysis of Animals and Cell Lines with Altered Expression of DmTNF Gene. Both genetically modified Drosophila models (i.e. in vivo models), and in vitro models such as genetically engineered cell lines expressing or misexpressing DmTNF genes, are useful for the functional analysis of these proteins. Model systems that display detectable phenotypes, can be used for the identification and characterization of DmTNF genes or other genes of interest and/or phenotypes associated with the mutation or mis-expression of DmTNF. The term "mis-expression" as used herein encompasses mis-expression due to gene mutations. Thus, a mis-expressed DmTNF protein may be one having an amino acid sequence that differs from wild-type (i. e. it is a derivative of the normal protein). A mis-expressed DmTNF protein may also be one in which one or more N-or C-terminal amino acids have been deleted, and thus is a "fragment" of the normal protein. As used herein 'mis-expression' also includes ectopic expression (e. g. by altering the normal spatial or temporal expression), over-expression (e. g. by multiple gene copies), underexpression, non-expression (e. g. by gene knockout or blocking expression that would otherwise normally occur), and further, expression in ectopic tissues.

The in vivo and in vitro models may be genetically engineered or modified so that they 1) have deletions and/or insertions of DmTNF genes, 2) harbor interfering RNA sequences derived from a DmTNF gene, 3) have had an endogenous DmTNF gene mutated (e. g. contain deletions, insertions, rearrangements, or point mutations in the DmTNF gene), and/or 4) contain transgenes for mis-expression of wild-type or mutant forms of a DmTNF gene. Such genetically modified vivo and in vitro models are useful for identification of genes and proteins that are involved in the synthesis, activation, control, etc. of DmTNF, and also downstream effectors of DmTNF function, genes regulated by DmTNF. The model systems can be used for testing potential pharmaceutical and compounds that interact with DmTNF, for example by administering the compound to the model system using any suitable method (c., direct contact ingestion injection, etc.) and observing any changes in phenotype, for example, defective movement, lethality, etc. Various genetic engineering and expression modification methods which can be used are well-known in the art, including chemical mutagenesis, transposon mutagenesis, antisense RNAi, dsRNAi, and transgene-mediated mis-expression.

Generating Loss-of-function Mutations by Mutagenesis. Loss-of-function mutations in an insect DmTNF gene can be generated by any of several mutagenesis methods known in the art (Ashburner. In Drosophila melanogaster: A Laboratory Manual (1989). Cold Spring Harbor, N.Y., Cold Spring Harbor Laboratory Press: pp. 299–418; Fly pushing: The Theory and Practice of Drosophila melanogaster Genetics (1997) Cold Spring Harbor Press, Plainview, N.Y., hereinafter "Fly Pushing"). Techniques for producing mutations in a gene or genome include use of radiation (e. g., X-ray, UV, or gamma ray); chemicals (e. g., EMS, MMS, ENU, formaldehyde, etc.), and insertional mutagenesis by mobile elements including dysgenesis induced by transposon insertions, or transposon-mediated deletions, for example, male recombination, as described below.

Other methods of altering expression of genes include use of transposons (e. g., P element, EP-type "overexpression trap" element, mariner element, pigg, Bac transposon, hermes, minos, sleeping beauty, etc.) to misexpress genes; antisense; double-stranded RNA interference; peptide and RNA aptamers; directed deletions; homologous recombination; dominant negative alleles; and intrabodies.

Transposon insertions lying adjacent to a DmTNF gene can be used to generate deletions of flanking genomic DNA, which if induced in the germline are stably propagated in subsequent generations. The utility of this technique in generating deletions has been demonstrated and is well-known in the art. One version of the technique using collections of P element transposon induced recessive lethal mutations (P lethals) is particularly suitable for rapid identification of novel, essential genes in Drosophila (Cooley et al., Science (1988) 239: 1121–1128; Spralding et al. PNAS (1995) 92: 0824–10830). Since the sequence of the P elements are known, the genomic sequence flanking each transposon insert is determined either by plasmid rescue (Hamilton et al. PNAS (191) 88: 2731–2735), or by inverse polymerase chain reaction (Rehm. http://www.fruitfly.org/methods/). A more recent version of the transposon insertion technique in male Drosophila using P elements is known as P-mediated male recombination (Preston and Engels, Genetics (1996) 144: 1611–1638).

Generating Loss-of-function Phenotypes Using RNA-based Methods. DmTNF genes may be identified and/or characterized by generating loss-of-function phenotypes in animals of interest through RNA-based methods, such as antisense RNA (Schubiger and Edgar, Methods in Cell Biology (1994) 44: 697–713). One form of the antisense RNA method involves the injection of embryos with an antisense RNA that is partial homologous to the gene of interest (in this case the DmTNF gene). Another form of the antisense RNA method involves expression of an antisense RNA partially homologous to the gene of interest by operably joining a portion of the gene of interest in the antisense orientation to a powerful promoter that can drive the expression of large quantities of antisense RNA, either generally throughout the animal or in specific tissues. Antisense NA-generated loss-of-function phenotypes have been reported previously for several Drosophila genes including cactus, pecanex, and Kruppel (LaBonne et al., Dev. Biol., (1989) 136 (1): 1–16; Schuh and Jackle, Genome (1989) 31 (1): 422–425; Geistera., Cell (1992) 71 (4): 613–621).

Loss-of-function phenotypes can also be generated by cosuppression methods (Bingham, Cell (1997) 90 (3): 385–387; Smyth. Curr. Biol. (1997) 7 (12): 793–795; Que and Jorgensen, Dev. Genet. (1998) 22 (1): 100–109). Cosuppression is a phenomenon of reduced gene expression produced by expression or injection of a sense strand RNA corresponding to a partial segment of the gene of interest. Cosuppression effects have been employed extensively in plants and C. elegans to generate loss-of-function phenotypes.

Cosuppression in Drosopllila has been shown where reduced expression of the Adh gene was induced from a white-Adh transgene (Pal-Bhadra et al. Cell (1997) 90 (3): 479–490).

Another method for generating loss-of-function phenotypes is by double-stranded RNA interference (dsRNAi). This method is based on the interfering properties of doublestranded RNA derived from the coding regions of gene and has proven to be of great utility in genetic studies of C. elegans (Fire et al., Nature (1998) 391: 806–811), and can also be used to generate loss-of-function phenotypes in Drosophila (Kennerdell and Carthew, Cell (1998) 95: 1017–1026; Misquitta and Patterson PNAS (1999) 96: 1451–1456).

Complementary sense and antisense RNAs derived from a substantial portion of a gene of interest, such as DmTNF gene are synthesized in vitro, annealed in an injection buffer, and introduced into animals by injection or other suitable methods such as by feeding, soaking the animals in a buffer containing the RNA, etc. Progeny of the dsRNA treated animals are then inspected for phenotypes of interest (PCT publication no. WO99/32619). dsRNAi can also be achieved by causing simultaneous expression in vivo of both sense and antisense RNA from appropriately positioned promoters operably fused to DmTNF sequences. Alternatively, the living food of an animal can be engineered to express sense and antisense RNA, and then fed to the animal. For example, C. elegans can be fed engineered E. coli, Drosophila can be fed engineered baker's yeast, and insects such as Lepidoptera and other plant-eating animals 273: 14309–14314). It has been demonstrated that RNA aptamers can inhibit protein function in Drosophila (Shi et al., Proc. Natl. Acad. Sci USA (19999) 96: 10033–10038).

Accordingly, RNA aptamers can be used to decrease the expression of DmTNF protein or derivative thereof, or a protein that interacts with the DmTNF protein.

Transgenic animals can be generated to test peptide or RNA aptamers in vivo (Kolonin and Finley, supra) For example, transgenic Drosophila lines expressing the desired aptamers may be generated by P element mediated transformation (discussed below). The phenotypes of the progeny expressing the aptamers can then be characterized.

Generating Loss of Function Phenotypes Using Intrabodies. Intracellularly expressed antibodies, or intrabodies, are single-chain antibody molecules designed to specifically bind and inactivate target molecules inside cells.

Intrabodies have been used in cell assays and in whole organisms such as Drosophila (Chen et al., Hum. Gen. Ther. (1994) 5: 595–601: Hassanzadeh et al. Febs Lett. (1998) 16 (1, 2): 75–80 and 81–86). Inducible expression vectors can be constructed with intrabodies that react specifically with DmTNF protein. These vectors can be introduced into model organisms and studied in the same manner as described above for aptamers.

Transgenesis. Typically, transgenic animals are created that contain gene fusions of the coding regions of the DmTNF gene (from either genomic DNA or cDNA) or genes engineered to encode antisense RNAs, cosuppression RNAs, interfering dsRNA, RNA aptamers, peptide aptamers, or intrabodies operably joined to a specific promoter and transcriptional enhancer whose regulation has been well characterized, preferably heterologous promoters/enhancers (i.e. promoters/enhancers that are non-native to the DmTNF genes being expressed).

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are also particularly useful for inserting sequences into a gene of interest so that the encoded protein is not property expressed, creating a "knock-out" animal of-function phenotype. Techniques are well-established for the use of P element in Drosophila (Rubin and Spradling, Science (1982) 218: 348–53-, U.S. Pat. No. 4,670,388).

Additionally, transposable elements that function in a variety of species, have been identified, such as PiggyBac (Thibault et al. Insect Mol Biol (1999) 8 (1): 119–23), hobo, and hermes.

P elements, or marked P elements, are preferred for the isolation of loss-of-function mutations in Drosophila DmTNF genes because of the precise molecular mapping of these genes, depending on the availability and proximity of preexisting P element insertions for use as a localized transposon source (Hamilton and Zinn, Methods in Cell Biology (1994) 44: 81–94; and Wolfner and Goldberg, Methods in Cell Biology (1994) 44: 33–80).

Typically, modified P elements are used which contain one or more elements that allow detection of animals containing the P element. Most often, marker genes are used that affect the eye color of Drosophila, such as derivatives of the Drosophila white or rosv genes (Rubin and Spradling, supra; and Klemenz et al., Nucleic Acids Res. (1987) 15 (10): 3947–3959). However, in principle any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4: 167–171), and lacZ sequences fused to a weak general promoter to detect the presence of enhancers with a developmental expression pattern of interest (Bellen et al., Genes Dev. (1989) 3 (9): 1288–1300). Other examples of marked P elements useful for mutagenesis have been reported (Nucleic Acids Research (1998) 26: 85–88; and http://flybase.bio.indiana.edu).

A preferred method of transposon mutagenesis in DroopMa employs the "local hopping" method (Tower et al. (Genetics (1993) 133: 347–359). Each new P insertion line can be tested molecularly for transposition of the P element into the gene of interest (e. g. DmTNF) by assays based on PCR. For each reaction, one PCR primer is used that is homologous to sequences contained within the P element and a second primer is homologous to the coding region or flanking regions of the gene of interest. Products of the PCR reactions are detected by agarose gel electrophoresis. The sizes of the resulting DNA fragments reveal the site of P element insertion relative to the gene of interest.

Alternatively, Southern blotting and restriction mapping using DNA probes derived from genomic DNA or cDNAs of the gene of interest can be used to detect transposition events that rearrange the genomic DNA of the gene. P transposition events that map to the gene of interest can be asserted for phenotypic effects in heterozygous or homozygous mutant Drosophila.

In another embodiment, Drosophila lines carrying P insertions in the gene of interest, can be used to generate localized deletions using known methods (Kaiser, Bioassays (1990) 12 (6): 297–301; Harnessing the power of Drosophila genetics, In Drosophila melanogaster: Practical Uses in Cell and Molecular Biology, Goldstein and Fyrberg, Eds. Academic Press, Inc. San Diego, Calif.). This is particularly useful if no P element transpositions are found that disrupt the gene of interest. Briefly, flies containing P elements inserted near the gene of interest are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny are screened by molecular techniques to identify deletion events that remove genomic sequence from the gene of interest, and assessed for phenotypic effects in heterozygous and homozygous mutant Drosophila.

Recently a transgenesis system has been described that may have universal applicability in all eye-bearing animals and which has been proven effective in delivering transgenes to diverse insect species (Berghammer et al., Nature (1999) 402: 370–371). This system includes: an artificial promoter active in eye tissue of all animal species, preferably containing three Pax6 binding sites positioned upstream of a TATA box (3xP3; Sheng et al., Genes Devel. (1997) 11: 1122–1131); a strong and visually detectable marker gene, such as GFP or other autofluorescent protein genes (Pasher et al., Gene (1992) 111: 229–233; U.S. Pat. No. 5,491,084); and promiscuous vectors capable of delivering transgenes to a broad range of animal species, for example transposon-based vectors derived from Hermes, PiggyBac, or mariner, or vectors based on pantropic VSV; pseudotyped retroviruses (Bums et (il., In Vitro Cell Dev Biol Anim (1996) 32: 78–84-., Jordan et al., Insect Mol Biol (1998) 7: 215–222; U.S. Pat. No. 5,670,345). Since the same transgenesis system can be used in a variety of phylogenetically diverse animals, comparative functional studies are greatly facilitated which is especially helpful in evaluating new applications to pest management.

In addition to creating loss-of-function phenotypes, transposable elements can be used to incorporate DmTNF, or fragments or derivatives thereof, as an additional gene into any region of an animals genome resulting in misexpression (including over-expression) of the gene. A preferred vector designed specifically for mis-expression of genes in transgenic Drosophila is derived from pGMR (Hay et b Development (1994) 120: 2121–2129), is 9 Kb long, and contains: an origin of replication for-E. coli; an ampicillin resistance gene; P element transposon 3' and 5'ends to mobilize the inserted sequences; a White marker gene; an expression unit comprising the TATA region of hsp70 enhancer; and the 3'untranslated region of a-tubulin gene. The expression unit contains a first multiple cloning site (MCS) designed for insertion of an enhancer and a second MCS located 500 bases downstream, designed for the insertion of a gene of interest. As an alternative to transposable elements, homologous recombination or gene targeting techniques can be used to substitute a heterologous DmTNF gene or fragment or derivative for one or both copies of the animal's homologous gene. The transgene can be under the regulation of either an exogenous or an endogenous promoter element, and be inserted as either a minigene or a large genomic fragment. Gene function can be analyzed by ectopic expression, using, for example, Drosophila (Brand et al., Methods in Cell Biology (1994) 44: 635–654).

Examples of well-characterized heterologous promoters that may be used to create transgenic Drosophila include heat shock promoters/enhancers such as the hsp70 and/hsp83 genes. Eye tissue specific promoters/enhancers include eyeless (Mozer and Benzer, Development (1994) 120: 1049–1058), sevenless (Bowtell et crl., PNAS (1991) 88 (15): 68536857), and glass-responsive promoters/enhancers (Quiring et al., Science (1994) 265: 785789). Wing tissue specific enhancers/promoters can be derived from the dpp or vestigal genes (Staehling-Hampton et al., Cell Growth Differ. (1994) 5 (6): 585–593; Kim et al., Nature (1996) 382: 133–138). Finally, where it is necessary to restrict the activity of dominant active or dominant negative transgenes to regions where DmTNF is normally active, it may be useful to use endogenous DmTNF promoters.

In Drosophila binary control systems that employ exogenous DNA are useful when testing the mis-expression of genes in a wide variety of developmental stage-specific and tissue-specific patterns. Two examples of binary exogenous regulatory systems include the UAS/GAL4 system from yeast (Hay et al. PNAS (1997) 94 (10): 5195–5200; Ellis et al., Development (1993) 119 (3): 855–865), and the "Tet system" derived from E. coli (Bello et al., Development (1998) 125: 2193–2202). The UAS/GAL4 system is a well-established and powerful method of mis-expression which employs the UAS (; upstream regulatory sequence for control of promoters by the yeast GAL4 transcriptional activator protein (Brand and Perrimon, Development (1993) 118 ('): 401–15). In this approach, transgenic Drosophila, termed "target" lines, are generated where the gene of interest to be mis-expressed is operably fused to an appropriate promoter controlled by UAS. Transgenic Drosophila strains, termed "driver" lines, are generated where the GAL4 coding region is operably fused to promoters/enhancers that direct the expression of the GAL4 activator protein in specific tissues, such as the eve, wing, nervous system, out, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of pre-existing driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food. Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a DmTNF gene has lethal or deleterious effects when mis-expressed at an early stage in development, such as the embryonic or larval stages, the function of the gene in the adult can still be assessed by adding tetracycline to the food during early stages of development and removing tetracycline later so as to induce mis-expression only at the adult stage.

Dominant negative mutations, by which the mutation causes a protein to interfere with the normal function of a wild-type copy of the protein, and which can result in loss-of function or reduced-function phenotypes in the presence of a normal copy of the gene, can be made using known methods (Hershkowitz. Nature (1987) 329: 219–222). In the case of active monomeric proteins, overexpression of an inactive form, achieved, for example, by linking the mutant gene to a highly active promoter, can cause competition for natural substrates or ligands sufficient to significantly reduce net activity of the normal protein.

Alternatively, changes to active site residues can be made to create a virtually irreversible association with a target.

Assays for Change in Gene Expression. Various expression analysis techniques may be used to identify genes which are differentially expressed between a cell line or an animal expressing a wild type DmTNF gene compared to another cell line or animal expressing a mutant DmTNF gene. Such expression profiling techniques include differential display, serial analysis of gene expression (SAGE), transcript profiling coupled to a gene database query, nucleic acid array technology, subtractive hybridization, and proteome analysis (e. g. mass-spectrometry and two dimensional protein gels). Nucleic acid array technology may be used to determine the genome-wide expression pattern in a normal animal for comparison with an animal having a mutation in the DmTNF gene. Gene expression profiling can also be used to identify other genes or proteins that may have a functional relation to DmTNF. The genes are identified by detecting changes in their expression levels following mutation, over-expression, underexpression, mis-expression or knock-out, of the DmTNF gene.

Phenotypes Associated With DmTNF Gene Mutations. After isolation of model animals carrying mutated or mis-expressed DmTNF genes or inhibitor RNAs, animals are carefully examined for phenotypes of interest. For analysis of DmTNF genes that have been mutated, animal models that are both homozygous and heterozygous for the altered DmTNF gene are analyzed. Examples of specific phenotypes that may be investigated include lethality; sterility; feeding behavior, tumor formation, perturbations in neuromuscular function including alterations in motility, and alterations in sensitivity to pharmaceuticals. Some phenotypes more specific to flies include alterations in: adult behavior such as, flight ability, walking, grooming, phototaxis, mating or egg-laying; alterations in the responses of sensory organs, changes in the morphology, size or number of adult tissues such as, eyes, wings, legs, bristles, antennae, gut, fat body, gonads, and musculature, larval tissues such as mouth parts, cuticles, internal tissues or invaginal discs; or larval behavior such as feeding, molting, crawling, or puparian formation; or development defects in any germline or embryonic tissues.

Genomic sequences containing a DmTNF gene can be used to engineer an existing mutant insect line, using the transgenesis methods previously described, to determine whether the mutation is in the DmTNF gene. Briefly, transformants are crossed for complementation testing to an existing or newly created panel of insect lines whose mutations have been mapped to the vicinity of the gene of interest (Fly Pushing, supra). If a mutant line is discovered to be rescued by the genomic fragment, as judged by complementation of the mutant phenotype, then the mutant fine likely harbors a mutation in the DmTNF gene. This prediction can be further confirmed by sequencing the DmTNF gene from the mutant line to identify the lesion in the DmTNF gene.

Identification of Genes That Modify DmTNF Genes. The characterization of new phenotypes created by mutations or misexpression in DmTNF genes enables one to test for genetic interactions between DmTNF genes and other genes that may participate in the same, related, or interacting genetic or biochemical pathway(s).

Individual genes can be used as target points in large-scale genetic modifier screens as described in more detail below. Alternatively, RNAi methods can be used to simulate loss of-function mutations in the genes being analyzed. It is of particular interest to investigate whether there are any interactions of DmTNF genes with other well-characterized genes, particularly genes involved in regulation of the cell cycle or apoptosis.

Genetic Modifier Screens. A genetic modifier screen using invertebrate model organisms is a particularly preferred method for identifying genes that interact with DmTNF genes, because large numbers of animals can be systemically screened making it more possible that interacting genes will be identified in Drosophila, a screen of up to about 10,000 animals is considered to be a pilot-scale screen. Moderate-scale screens usually employ about 10,000 to about 50,000 flies, and large-scale screens employ greater than about 50,000 flies. In a genetic modifier screen, animals having a mutant phenotype due to a mutation in or misexpression of the DmTNF gene are further mutagenized, for example by chemical mutagenesis or transposon mutagenesis.

The procedures involved in typical Drosophila genetic modifier screens are well known in the art (Wolfner and Goldberg, Methods in Cell Biology (1994) 44: 33–80; and Karim et al. Genetics (1996) 143: 315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are presumed to have mutations in other genes, called "modifier genes", that participate in the same phenotype-generating pathway. These progeny are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Standard techniques used for the mapping of modifiers that come from a genetic screen in Drosophila include meiotic mapping with visible or molecular genetic markers; male-specific recombination mapping relative to P-element insertions; complementation analysis with deficiencies, duplications, and lethal P-element insertions, and cytological analysis of chromosomal aberrations (Fly Pushing, supra). Genes corresponding to modifier mutations that fail to complement a lethal P-element may be cloned by plasmid rescue of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated with DmTNF genes using methods described above. Also, the new modifier mutations can be tested for interactions with genes in other pathways that are not believed to be related to regulation of cell cycle or apoptosis.

New modifier mutations that exhibit specific genetic interactions with other genes implicated in cell cycle regulation or apoptosis, and not with genes in unrelated pathways, are of particular interest.

The modifier mutations may also be used to identify "complementation groups". Two modifier mutations are considered to fall within the same complementation group if animals carrying both mutations in trans exhibit essentially the same phenotype as animals that are homozygous for each mutation individually and generally are lethal when in trans to each other (Fly Pushing, xpra). Generally, individual complementation groups defined in this way correspond to individual genes.

When DmTNF modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of DmTNF genes, human and rodent homologs of the modifier genes are of particular interest.

Although the above-described Drosophila genetic modifier screens are quite powerful and sensitive, some genes that interact with DmTNF genes may be missed in this approach, particularly if there is functional redundancy of those genes. This is because the vast majority of the mutations generated in the standard mutagenesis methods will be loss of-function mutations, whereas gain-of-function mutations that could reveal genes with functional redundancy will be relative rare. Another method of genetic screening in Drosophila has been developed that focuses specifically on systematic gain-of-function genetic screens (Rorth et al., Development (1998) 125: 1049–1057). This method is based on a modular mis-expression system utilizing components of the GAL4/UAS system (described above) where a modified P element, termed an "enhanced P" (EP) element, is genetically engineered to contain a GAL4-responsive UAS element and promoter. Any other transposons can also be used for this system. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL4-regulated promoter, and increased expression or mis-expression of the randomly tagged gene can be induced by crossing in a GAL4 driver gene.

Systematic gain-of-function genetic screen for modifiers of phenotypes induced by mutation or mis-expression of a DmTNF gene can be performed by crossing several thousand Drosophila EP lines individually into a genetic background containing a mutant or mis-expressed DmTNF gene, and further containing an appropriate GAL4 driver transgene. It is also possible to remobilize the EP elements to obtain novel insertions. The progeny of these crosses are then analyzed for enhancement or suppression of the original mutant phenotype as described above. Those identified as having mutations that interact with the DmTNF gene can be tested further to verify the reproducibility and specificity of this genetic interaction.

EP insertions that demonstrate a specific genetic interaction with a mutant or mis-expressed DmTNF gene, have a physically tagged new gene which can be identified and sequenced using PCR or hybridization screening methods, allowing the isolation of the genomic DNA adjacent to the position of the EP element insertion.

Identification of Molecules that Interact With DmTNF. A variety of methods can be used to identify or screen for molecules, such as proteins or other molecules that interact with DmTNF protein, or derivatives or fragments thereof. The assays may employ purified DmTNF protein, or cell lines or a model organism such as Drosophila that has been genetically engineered to express DmTNF protein. Suitable screening methodologies are well known in the art to test for proteins and other molecules that interact with a gene/protein of interest (see PCT International Publication No. WO 96/34099). The newly identified interacting molecules may provide new targets for pharmaceutical agents. Any of a variety of exogenous molecules, both naturally occurring and/or synthetic (e. g., libraries of small molecules or peptides, or phage display libraries), may be screened for binding capacity. In a typical binding experiment the DmTNF protein or fragment is mixed with candidate molecules under conditions conducive to binding, sufficient time is allowed for any binding to occur, and assays are performed to test for bound complexes. A variety of assays to find interacting proteins are known in the art, for example, immunoprecipitation with an antibody that binds to the protein in a complex followed by analysis by size fractionation of the immunoprecipitated proteins (e. g. by denaturing or nondenaturing polyacrylamide gel electrophoresis) Western analysis, nondenaturing gel electrophoresis, etc.

Two-hybrid assay systems. A preferred method for identifying interacting proteins is a two-hybrid assay system or variation thereof (Fields and Song, Nature (1989) 340: 945–'46; U.S. Pat. No. 5,283,173; for review see Brent and Finley, Annu. Rev. Genet. (1997) 31: 663–704). The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with DmTNF protein, the "bait" is preferably a DmTNF protein, expressed as a fusion protein to a DNA binding domain; and the "prey" protein is a protein to be tested for ability to interact with the bait, and is expressed as a fusion protein to a transcription activation domain. The prey proteins can be obtained from recombinant biological libraries expressing random peptides.

The bait fusion protein can be constructed using any suitable DNA binding domain, such as the E. coli LexA repressor protein, or the yeast GAL4 protein (Bartel et al., BioTechniques (1993) 14: 920–924, Chasman et al., Mol. Cell. Biol. (1989) 9: 4746–4749; Ma et al. Cell (1987) 48: 847–853; Ptashne et al. Nature (1990) 346: 329–331). The prey fusion protein can be constructed using any suitable activation domain such as GAL4, VP16, etc. The preys may contain useful moieties such as nuclear localization signals (Ylikomia. EMBOJ. (1992) 11: 3681–3694; Dinawall and Laskey, Trends Biochem. Sci. (1991) 16: 479–481), or epitope tags (Allen et al., Trends Biochem. Sci. Trends Biochem. Sci. (1995) 20: 511–516) to facilitate isolation of the encoded proteins. Any reporter gene can be used that has a detectable phenotype such as reporter genes that allow cells expressing them to be selected by growth on appropriate medium (e. g. HIS3, LEU2 described by Chien et al., PNAS (1991) 88: 9572–9582; and Gyuris et al., Cell (1993) 75: 791–803). Other reporter genes, such as LacZ and GFP, allow cells expressing them to be visually screened (Chien et al., supra).

Although the preferred host for two-hybrid screening is the yeast, the host cell in which the interaction assay and transcription of the reporter gene occurs can be any cell, such as mammalian (e. g. monkey, mouse, rat, human, bovine, etc.), chicken, bacterial, or insect cells. Various vectors and host strains for expression of the two fusion protein populations in yeast can be used (U.S. Pat. No. 5,468,614; Bartel et al. Cellular Interactions in Development (1993) Hartley, ed. Practical Approach Series xviii. IRL: Press at Oxford University Press, New York, N.Y., pp. 153–179; and Fields and Stemglanz, Trends In Genetics (1994) 10: 286–292). As an example of a mammalian system, interaction of activation tagged VP16 derivatives with a GAL4-derived bait drives expression of reporters that direct the synthesis of hygromycin B phosphotransferase, chloramphenicol acetyltransferase, or CD4 cell surface antigen (Fearon et al. PNAS (1992) 89: 7958–7962).

As another example, interaction of VP16-tagged derivatives with GAL4-derived baits drives the synthesis of SV40 T antigen, which in turn promotes the replication of the prey plasmid, which carriers an SV40 origin (Vasavada et al. PNAS (1991) 88: 10686–10690).

Typically, the bait DmTNF gene and the prey library of chimeric genes are combined by mating the two yeast strains on solid or liquid media for a period of approximately 6–8 hours. The resulting diploids contain both kinds of chimeric genes, i. e., the DNA-binding domain fusion and the activation domain fusion. Transcription of the reporter gene can be detected by a linked replication assay in the case of SV40 T antigen (Vasavada et al., supra) or using immunoassay methods (Alam and Cook, Anal. Biochem. (1990) 188: 245–254).

The activation of other reporter genes like URA3, HIS3, LYS2 or LEU2 enables the cells to grow in the absence of uracil, histidine, lysine, or leucine, respectively, and hence serves as a selectable marker. Other types of reporters are monitored by measuring a detectable signal. For example, GFP and LacZ have gene products that are fluorescent and chromogenic, respectively.

After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotide primers specific for the coding region of the DNA binding domain or activation domain. If a shuttle (yeast to E. coli) vector is used to express the fusion proteins, the DNA sequences encoding the proteins can be isolated by transformation of E. coli using the yeast DNA and recovering the plasmids from E. coli. Alternatively, the yeast vector can be isolated, and the insert encoding the fusion protein subcloned into a bacterial expression vector, for growth of the plasmid in E. coli.

Also within the scope of the present invention is a process for modulating the activity of the DmTNF of the present invention, directly or through the receptor for the DmTNF disclosed herein. The term "modulating" encompasses enhancement, diminishment, activation or inactivation of the activity of the DmTNF disclosed herein. Ligands to the receptor of the DmTNF of the present invention, including peptides, proteins, small molecules, and antibodies, that are capable of binding to the receptor and modulating its activity are encompasses herein. Also encompassed herein are molecules that bind to the DmTNF disclosed herein (e.g., antibodies specific for the DmTNF of the present invention). These compounds are useful in modulating the activity of the DmTNF and/or the receptor for DmTNF, and in treating DmTNF-associated disorders. "DmTNF-associated disorders" refers to any disorder or disease state in which the DmTNF protein plays a regulatory role in the metabolic pathway of that disorder or disease. Such disorders or diseases may include rheumatoid arthritis and transplant rejection. As used herein the term "treating" refers to the alleviation of symptoms of a particular disorder in a patient, the improvement of an ascertainable measurement associated with a particular disorder, or the prevention of a particular immune, inflammatory or cellular response (such as transplant rejection).

Screening

The present invention also relates to methods of screening. Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case binding of the DmTNF of the present invention to its receptor. Techniques known in the art are amenable to high through-put analysis for screening large numbers of sequences created, e.g., by random mutagenesis techniques.

Two hybrid assays can be used to identify modulators of the interaction a receptor and the DmTNF of the present invention. These modulators may include agonists or antagonists. In one approach to screening assays, the candidate protein or peptides are displayed on the surface of a cell or viral particle, and the ability of particular cells or viral particles to bind an appropriate receptor protein via the displayed product is detected in a "panning assay". In a similar fashion, a detectably labeled ligand can be used to score for potentially functional peptide homologues. Fluorescently labeled ligands, e.g., receptors, can be used to detect homologue which retain ligand-binding activity. The use of fluorescently labeled ligand allows cells to be visually inspected and separated under fluorescence microscope or to be separated by a fluorescence-activated cell sorter.

High through-put assays can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a receptor and the DmTNF of the present invention can be used to identify antagonists from a group of peptide fragments isolated through one of the primary screens. Therefore, methods for generating fragments and analogs and testing them for activity are known in the art. Once a sequence of interest is identified, it is routine for one skilled in the art to obtain agonistic or antagonistic analogs, fragments, and/or ligands.

Drug screening assays are also provided in the present invention. By producing purified and recombinant DmTNF of the present invention, or fragments thereof, one skilled in the art can use these to screen for drugs which are either agonists or antagonists of the normal cellular function or their role in cellular signaling. In one embodiment, the assay evaluates the ability of a compound to modulate binding between a receptor and the DmTNF of the present invention. The term "modulating" encompasses enhancement, diminishment, activation or inactivation of the receptor for DmTNF. Assays useful to identify a receptor to the DmTNF of the present invention are encompassed herein. A variety of assay formats will suffice and are known by those skilled in the art.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as primary screens in that they can be generated to permit rapid development and relatively easy detection of an alteration in a molecular target which is mediated by a test compound.

Antibodies

The invention also includes antibodies specifically reactive with the DmTNF of the present invention, or a portion thereof. Anti-protein/anti-peptide antisera or monoclonal antibodies can be made by standard known procedures. A mammal such as a mouse, a hamster or rabbit can be immunized with an immunogenic form of the peptide. Techniques for conferring immunogenicity on a protein or peptide include conjugation to carriers or other techniques known in the art. An immunogenic portion of the DmTNF of the present invention can be administered in the presence of adjuvant. The progress of immunization can be monitored by detection of antibody titers in plasma or serum.

The term "antibody" as used herein is intended to include fragments thereof which are also specifically reactive with the DmTNF of the present invention. Antibodies can be fragmented using conventional techniques and the fragments screened for utility in the same manner as whole antibodies. For example F(ab')2 fragments can be generated by treating antibody with pepsin. The resulting F(ab')2 fragment can be treated to reduce disulfide bridges to produce Fab' fragments. The antibody of the present invention is further intended to include chimeric and humanized molecules that recognize and bind to the DmTNF of the present invention.

Both monoclonal and polyclonal antibodies directed against the DmTNF of the present invention, and antibody fragments such as Fab', sFv and F(ab')2, can be used to block the action of the DmTNF of the present invention and allow study of the role of a particular DmTNF of the present invention. Alternatively, such antibodies can be used therapeutically to block the DmTNF of the present invention in a subject mammal, e.g., a human. In a preferred embodiment a therapeutic compositions comprising an antibody of the present invention can also comprise a pharmaceutically acceptable carrier, solvent or diluent, and be administered by systems known in the art.

Antibodies which specifically bind to the DmTNF of the present invention, or fragments thereof, can also be used in immunohistochemical staining of tissue samples in order to evaluate the abundance and pattern expression of the DmTNF of the present invention. Antibodies can be used diagnostically in immunoprecipitation, immunoblotting, and enzyme linked immunosorbent assay (ELISA) to detect and evaluate levels of the DmTNF of the present invention in tissue or bodily fluid.

Antibodies and Immunoassay DmTNF proteins encoded by any of SEQ ID NOs and derivatives and fragments thereof, such as those discussed above, may be used as an immunogen to generate monoclonal or polyclonal antibodies and antibody fragments or derivatives (e.g. chimeric, single chain, Fab fragments). For example, fragments of a DmTNF protein, preferably those identified as hydrophilic, are used as immunogens for antibody production using art known methods such as by hybridomas; production of monoclonal antibodies in germ-free animals (PCT/US90/02545); the use of human hybridomas (Cole et al., PNAS (1983) 80: 2026–2030; Cole et al., in Monoclonal Antibodies and Cancer Therapy (1985) Alan R. Liss, pp. 77–96), and production of humanized antibodies (Jones et al., Nature (1986) 321: 522–525; U.S. Pat. No. 5,530,101). In a particular embodiment, DmTNF polypeptide fragments provide specific antigens and/or immunogens, especially when coupled to carrier proteins.

For example, peptides are covalently coupled to keyhole limpet antigen (KLH) and the conjugate is emulsified in Freund's complete adjuvant. Laboratory rabbits are immunized according to conventional protocol and bled. The presence of specific antibodies is assayed by solid phase immunosorbent assays using immobilized corresponding polypeptide.

Specific activity or function of the antibodies produced may be determined by convenient cell-based, or assays, such as in vitro binding assays, etc. Binding affinity may be assayed by determination of equilibrium constants of antigen-antibody association (usually at least about $10^7$ M-1, preferably at least about $10^8$ M-1, more preferably at least about $10^9$ M). Examples below further describes the generation of anti-DMDmTNF antibodies.

Immunoassays can be used to identify proteins that interact with or bind to DmTNF protein. Various assays are available for testing the ability of a protein to bind to or compete with binding to a wild-type DmTNF protein or for binding to an anti-DmTNF protein antibody. Suitable assays include radioimmunoassays, ELISA (enzyme linked immunosorbent assay), immunoradiometric assays, gel diffusion precipitin reactions, immunodiffusion assays, in, sitar immunoassays (e. using colloidal gold, enzyme or radioisotope labels), western blots, precipitation reactions, agglutination assays (e. g., gel agglutination assays, hemaglutination assays), complement fixation assays, immunofluorescence assays, protein A assays, immunoelectrophoresis assays, etc.

Further polypeptides of the invention relate to antibodies and T-cell antigen receptors (TCR) which immunospecifically bind a polypeptide, polypeptide fragment, or variant of SEQ ID NO:2, 4, 6, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin, including birds and mammals. Preferably, the antibodies are murine (e.g., mouse and rat), donkey, ship rabbit, goat, guinea pig, camel, horse, chicken, or possibly human. As used herein, "human" antibodies include antibodies having the amino acid sequence of an immunoglobulin and include antibodies isolated from immunoglobulin libraries or from animals transgenic for one or more immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–60 (1991); U.S. Pat. Nos. 4,474,893; 4,714,681; 4,925,648; 5,573,920; 5,601,819; Kostelny et al., J. Immunnol 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acids residues, or listed in the Tables and Figures. Antibodies which specifically bind any epitope or polypeptide of the present invention may also be excluded. Therefore, the present invention includes antibodies that specifically bind polypeptides of the present inventiobn, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with human, murine, rat and/or rabbit homologs of Drosophila proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 19^{-5}$ M, $10^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preverably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biologial activities of the ligand-mediated receptor actiovation, for example, by inducing dimerization of the receptor. The antibodies may be specified as agonists, antagonists or inverse agonists for biolgical activities comprising the specifc biological activities of the peptides of the invention disclosed herein. The above antibody agonists can be made using methods known in the art. See, e.g., PCT publication WO 96/40281; U.S. Pat. No. 5,811,097; Deng et al., Blood 92(6);1981–1988 (1998); Chen et al., Cancer Res. 58(16):3668–3678 (1998); Harrop et al., J. Immunol. 161 (4):1786–1794 (1998); Zhu et al., Cancer Res. 58(15) :3209–3214 (1998); Yoon et al., J. Immunol. 160(7) :3170–3179 (1998); Prat et al., J. Cell. Sci. 111(Pt2) :237–247 (1998); Pitard et al., J. Immunol. Methods 205(2) :177–190 (1997); Liautard et al., Cytokine 9(4):233–241 (1997); Carson et al., Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleodes, or toxins, See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivation by known protecting/ blocking groups, proteolytic cleavage, linkage to a cellular ligand or other protein, etc. any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, 2$^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include that are not limited to, Freund's (complete and incomplete), mineral gels such as aluminum hydroxide, surface active substances such as lysolecithin, pluronic polyols, polyanions, peptides, oil emulsions, keyhole limpe: hemocyanins, dinitrophenol, and potentially useful ajuvants such as BCG (bacille Calmette-Guerin) and corynebacterium parvum. Such adjuvants are also well known in the art. For the purposes of the invention, "immunizing agent" may be defined as a polypeptide of the invention, including fragments, variatns, and/or derivatives thereof, in addition to fusions with heterologous polypeptides and other forms of the polypeptides described herein.

Typically, the immunizing agent and/or adjuvant will be injected in the mammal by mulitple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methologoy, or other methods known to the skilled artisan. Examples of such immunogenic proteins include, but are not skilled to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, peptides, oil emulsions, keyhole limpet hemocyanin, dinitrophenol, and potentially useful human adjuvants such as BCG (bacille Calmette-Guerin) and Corynebacterium parvum. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hydbridoma methods, such as those described by Kohler and Milstein, Nature, 256:495 (1975) and U.S. Pat. No. 4,375,110, by Harlow, et al., Antibodies: A Laboratory Manual, (Cold spring Harbor Laboratory Press, $2^{nd}$ ed. (988), by Hammerline, et al., Monoclonal Antibodies and T-Cell Hybridomas (Elsevier, N.Y., (1981)), or other methods known to the artisan. Other examples of methods which may be employed for producing monoclonal antibodies includes, but art not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survial of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va.

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hydriboma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or mycloma cells that do not otherwise produce immunoglubulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method invovles recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phase display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., Drosophila, human, or murine). Phase expressing an antigen binding domain that binds the antigen of interest can be selected or identified with antigen, e.g., using labeled antigen or antigen bound or captured to a solid surface or bead. Phase used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22342; Mullinax et al., BioTechniques 12(6) :864–869 (1992); and Sawai et al., AJRI 34:26–34 (1995); and Better et al., Science 240:1041–1043 (1988) (said references incorporated by reference in their entireites). Examples of techniques which can be used to produce signle-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5)L:437–444; (1989) and Nissinoff, J. Immunol. 147(8)2429–2438 (1991)). For example, antibodies which bind to and competitively inhibit polypeptide mulitimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligans/receptors, and thereby block its biological activity.

The antibodies of the present invention may be bispecific antibodies. Bispecific antibodies are monoclonal antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusins. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym, 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. N. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably an antibody that binds to a polypeptide having the amino acid sequence of SEQ ID NO:2, 4, or 6.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonunucleotides, and them amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using a synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions. The framework regions may be naturally occurring or consensus framework regions. Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra eta al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibodiy, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In a preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms suchu as bacteria (e.g., *E. coli*, *B subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cells systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and bidning to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa california nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted n the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codom must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Method in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example CRL7030 and Hs578Bst.

For long-term, high-yield production of recombinant proteins, stable expression is preferred. For example, cell lines which stably express, the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowery et al., Cell 22:817 (1980)) genes can be employed in tk- hgprt- or aprt- cells, respectively. Also, antimetabolite resistance can be used as the basis of selection for the following genes: dhfr, which confers reistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequence for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypetides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptide to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said reference incorporated by reference by their entireties).

As discussed, supra, the polypeptides corresponding to a polypeptide, polypeptide fragment, or a variant of SEQ ID NO:2, 4, or 6 may be fused or conjugated to the above antibody portions to increase the in vivo half life of the polypeptides or for use in immunoassays using methods known in the art. Further, the polypeptides corresponding to SEQ ID NO: 2, 4, or 6 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins (EP 394,827; Traunecker et al., Nature, 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-hisitidine peptide, such as the tag provided in a pQE vector (QIAGEN, Inc. 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clincial testing procedure to, e.g., determine the efficacy of a given treatment regiment. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; eamples of suitable prosthetic group compexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as a brin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agnet, e.g., TNF-alpha, TNF-beta, AIM I (See, International Publication No. WO 97/33899), AIM II (See, International Publication No. WO 97/34911), or Fas Ligand (Takahashi et al., Int. Immunol., 6:1567–1574 (1994)).

Antibodies may also be attached to sold supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting OF Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological Ad Clinical Applications, Pinchera et al. (eds.), pp. 475–506 (1985); "Analysis, Resultsm, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjuates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered along or in combination with cytotoxic factor(s) and/or cytokine(s) can be used as a therapeutic Uses for Antibodies Directed Against Polypeptides of the Invention The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the samle is a tissue (e.g., embryo, larvae, animal, etc.), biological fluid (e.g., blood, urine, semen, saliva, etc.), biological extract (e.g., tissue or cellular homogenate, etc.), a protein microchip (e.g., See Arenkov P, et al., Anal Biochem, 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either hetergeneous or homogenous phases (Zola, Monoclonal Antibodies: A Manual of Techniques, CRC Press, Inc., (1987), pp147–158). The antibodies used in the diagnostic assays can be labeled with a detectable moiety. The detectable moiety should be capable of producing, either directly or indirectly, a detectable signal. For example, the detectable moeity may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green flourescent protein, horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobolized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. the translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassay, ELISA (enzyme linked immunosorbent assay), "sandwich" immunoassays, immunoprecipitation assays, precipitin reactions, get diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Gene Therapy and Antibody-based Gene Therapy

Gene constructs of the present invention can also be used as part of a gene therapy protocol to deliver nucleic acids encoding the DmTNF of the present invention, or an agonist or antagonist form of a DmTNF protein or peptide. The invention features expression vectors for in vivo transfection and expression of a DmTNF. Expression constructs of the DmTNF of the present invention, may be administered in any biologically effective carrier, e.g., any formulation or composition capable of effectively delivering the DmTNF gene to cells in vivo. Approaches include insertion of the subject gene in viral vectors including recombinant retroviruses, adenoviruses, adeno-associated viruses, and herpes simplex virus-1, or recombinant bacterial or eukaryotic plasmids. Viral vectors transfect cells directly; an advantage of infection of cells with a viral vector is that a large proportion of the targeted cells can receive the nucleic acid. Several viral delivery systems are known in the art and can be utilized by one practicing the present invention.

In addition to viral transfer methods, non-viral methods may also be employed to cause expression of the DmTNF in the tissue of an insect or animal. Most non-viral methods of gene transfer rely on normal mechanisms used by mammalian cells for the uptake and intracellular transport of macromolecules. Exemplary gene delivery systems of this type include liposomal derived systems, poly-lysine conjugates, and artificial viral envelopes. DNA of the present invention may also be introduced to cell(s) by direct injection of the gene construct or electroporation.

In clinical settings, the gene delivery systems for the therapeutic DmTNF gene (or homolog thereof identified using all or a portion of the gene disclosed herein) can be introduced into a patient by any of a number of methods, each of which is known in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. In a most preferred embodiment, antibody based gene therapy is useful for inhibiting a protein of interest (e.g., the proteins of the present invention) to facilitate the elucidation of biological pathways, characterize gene function, and/or to create a desirable phenotypic background for studies of other proteins and/or pathways. Gene therapy refers to therapy performed by the administration to an organism of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into Drosophila are known in the art and are discussed herein (e.g., P-element, transposon mediated, etc.).

Alternatively, viral vectors that contains nucleic acid sequences encoding an antibody of the invention are used. For example, a retroviral vector can be used (see Miller et al., Meth. Enzymol. 217:581–599 (1993)). The retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Diagnosis and Imaging With Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder (e.g., phenotype), comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit.

Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced inbetween such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existance of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:65), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of the coding region of a repeating series of up to nine arginine amino acids to a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivitized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann N Y Acad Sci. 1999;886:233–5), or HC toxin (Tonukari N J, et al., Plant Cell. 2000 February; 12(2):237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a *Pichea* yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methioine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivatization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly (vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivatization include saccharides that can be attached to the polypeptides of the invention via alkylation or acylation reactions.

Moreover, the invention also encompasses derivatization of the polypeptides of the present invention, for example, with lipids (including cationic, anionic, polymerized, charged, synthetic, saturated, unsaturated, and any combination of the above, etc.), stabilizing agents.

The invention encompasses derivatize of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galactocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines; erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivitized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivatization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 4, or 6 (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication No: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478, 925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription, factors. Preferably, the cis-acting DNA sequence elements and transacting transcription factors are operable in mammals. Further, the trans-acting transcription factors of such "artificial" promoters could also be "artificial" or chimeric in design themselves and could act as activators or repressors to said "artificial" promoter.

Identification of Potential Drug Targets. Once new DmTNF genes or DmTNF interacting genes are identified, they can be assessed as potential drug or pesticide targets using animal models such as Drosophila or other insects, or using cells that express endogenous DmTNF, or that have been engineered to express DmTNF.

Assays of Compounds on Insects Potential. Insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection.

Insecticides are typically very hydrophobic molecules and must commonly be dissolved in organic solvents, which are allowed to evaporate in the case of methanol or acetone, or at low concentrations can be included to facilitate uptake (ethanol, dimethyl sulfoxide).

The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from pupanum). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior locomotion, and molting may be observed. For application on adults, behavior and neurological defects are observed, and effects on fertility are noted. Any deleterious effect on insect survival, motility and fertility indicates that the compound has utility in controlling pests.

For a chronic exposure assay, adults are placed on vials containing the compounds for 48 hours, then transferred to a clean container and observed for fertility, neurological defects, and death.

Assay of Compounds using Cell Cultures. Compounds that modulate (e.g. block or enhance) DmTNF activity may be tested on cells expressing endogenous normal or mutant DmTNFs, and/or on cells transfected with vectors that express DmTNF, or derivatives or fragments of DmTNF. The compounds are added at varying concentration and their ability to modulate the activity of DmTNF genes is determined using any of the assays for tumor suppressor genes described above (e.g. by measuring transcription activity, apoptosis, proliferation/cell cycle and/or transformation). Compounds that selectively modulate DmTNF are identified as potential drug candidates having DmTNF specificity.

Identification of small molecules and compounds as potential pharmaceutical compounds from large chemical libraries requires high-throughput screening (HTS) methods (Bolger, Drug Discovery Today (1999) 4: 251–253). Several of the assays mentioned herein can lend themselves to such screening methods. For example, cells or cell lines expressing wild type or mutant DmTNF protein or its fragments, and a reporter gene can be subjected to compounds of interest, and depending on the reporter genes, interactions can be measured using a variety of methods such as color detection, fluorescence detection (e.g. GFP), autoradiography, scintillation analysis. etc.

Agricultural Uses of Insect DmTNF Sequences. Insect DmTNF genes may be used in controlling agriculturally important pest species. For example, the proteins, genes, and RNAs disclosed herein, or their fragments may have activity in modifying the growth, feeding and/or reproduction of crop-damaging insects, or insect pests of farm animals or of other animals. In general, effective pesticides exert a disabling activity on the target pest such as lethality, sterility, paralysis, blocked development, or cessation of feeding. Such pests include egg, larval, juvenile and adult forms of flies, mosquitoes, fleas, moths, beetles, cicadia, grasshoppers, aphids and crickets.

The functional analyses of insect DmTNF genes described herein has revealed roles for these genes and proteins in controlling apoptosis, response to DNA damaging agents, and protection of cells of the germline. Since overexpression of DmTNF induces apoptosis in Drosophila, the insect DmTNF genes and proteins in an activated form have application as "cell death" genes which if delivered to or expressed in specific target tissues such as the gut, nervous system, or gonad, would have a use in controlling insect pests. Alternatively, since DmTNF plays a role in response to DNA damaging agents such as X-rays, interference with DmTNF function in insects has application in sensitizing insects to DNA damaging agents for sterilization. For example, current methods for controlling pest populations through the release of irradiated insects into the environment (Knipling, J Econ Ent (1955) 48: 459–462; Knipling (1979) U. S. Dept. Agric. Handbook No. 512) could be improved by causing expression of dominant negative forms of DmTNF genes, proteins, or RNAs in insects and most preferably germline tissue of insects or by exposing insects, to chemical compounds which block DmTNF function.

Mutational analysis of insect DmTNF proteins may also be used in connection with the control of agriculturally-important pests. In this regard, mutational analysis of insect DmTNF genes rational approach to determine the precise biological function of this class of proteins in invertebrates. Further, mutational analysis coupled with large-scale systematic genetic modifier screens provides a means to identify and validate other potential pesticide targets that might be constituents of the DmTNF signaling pathway.

Tests for pesticidal activities cart be any method known in the art. Pesticides comprising the nucleic acids of the insect DmTNF proteins may be prepared in a suitable vector for delivery to a plant or animal. Such vectors include Agrobacterium tumefaciens Ti plasmid-based vectors for the generation of transgenic plants (Horsch et al., Proc Natl Acad Sci U S A., (1986) 83 (8) 2571–2575; Fraley et al., Proc. Natl. Acad. Sci. USA (1983) 80: 4803), or recombinant cauliflower mosaic virus for the inoculation of plant cells or plants (U.S. Pat. No. 4,407,956); retrovirus based vectors for the introduction of genes into vertebrate animals (Bums et al., Proc. Natl. Acad. Sci. USA (1993) 90: 8033–37): and vectors based on transposable elements for incorporation into invertebrate animals using vectors and methods already described above. For example, transgenic insects can be generated using a transgene comprising a DmTNF gene operably fused to an appropriate inducible promoter, such as a tTA-responsive promoter, in order to direct expression of the tumor suppressor protein at an appropriate time in the life cycle of the insect. In this way, one may test efficacy as an insecticide in, for example, the larval phase of the life cycle (e.g., when feeding does the greatest damage to crops).

Recombinant or synthetic DmTNF proteins. RNAs or their fragments, in wild-type or mutant forms, can be assayed for insecticidal activity by injection of solutions of DmTNF proteins or RNAs into the hemolymph of insect larvae (Blackburn, et al., Appl. Environ. Microbiol. (1998) 64 (8): 3036–41; Bowen and Ensign, Appl. Environ. Microbiol. (1998) 64 (8): 3029–35). Further, transgenic plants that express DmTNF proteins or RNAs or their fragments can be tested for activity against insect pests (Estruch et al., Nat. Biotechnol).

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (broken wings, wounds, bums, incisions, or ulcers), age, disease including systemic cytokine damage.

Tissues that could be regenerated using the present invention include organs, muscle (smooth, skeletal or cardiac), vasculature (including vascular and lymphatics), nervous, and hematopoietic.

Moreover, a polynucleotide or polypeptide and/or agonist or antagonist of the present invention may increase regeneration of tissues difficult to heal. A polynucleotide or polypeptide and/or agonist or antagonist of the present invention could also be used prophylactically in an effort to avoid damage.

Similarly, nerve and brain tissue could also be regenerated by using a polynucleotide or polypeptide and/or agonist or antagonist of the present invention to proliferate and differentiate nerve cells.

Chemotaxis

A polynucleotide or polypeptide and/or agonist or antagonist of the present invention may have chemotaxis activity. A chemotaxic molecule attracts or mobilizes cells to a particular site in an organism, such as during inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane.

Preferred cells include cells from invertebrates, yeast, Drosophila, or *E. coli*, in addition to, mammals. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FAGS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniqucs 24(2): 308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members.

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a Drosophila cell, a the polypeptide of the present invention, the compound to be screened and 3[H] thymidine under cell culture conditions where the *Drosophila* cell would normally proliferate. A control assay may be performed in the absence of the compound to be screened and compared to the amount of proliferation in the presence of the compound to determine if the compound stimulates proliferation by determining the uptake of 3[H] thymidine in each case. The amount of cell proliferation is measured by liquid scintillation chromatography which measures the incorporation of 3[H] thymidine. Both agonist and antagonist compounds may be identified by this procedure.

In another method, *Drosophila* cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, CAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in an organisms, by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

Another aspect of the invention relates to the use of an isolated nucleic acids in "antisense" therapy. As used herein, "antisense" therapy refers to administration or in situ generation of oligonucleotides or their derivatives which specifically hybridize under cellular conditions, with the cellular mRNA and/or genomic DNA encoding the DmTNF of the present invention so as to inhibit expression of the encoded protein, e.g., by inhibiting transcription and/or translation. In general, "antisense" therapy refers to the range of techniques generally employed in the art, and includes any therapy which relies on specific binding to oligonucleotide sequences.

In specific embodiments, antagonists according to the present invention are nucleic acids corresponding to the sequences contained in SEQ ID NO: 1, 3, 5, or the complementary strand thereof. In one embodiment, antisense sequence is generated internally by the organism, in another embodiment, the antisense sequence is separately administered (see, for example, O'Connor, Neurochem., 56:560 (1991). Oligodeoxynucleolides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myc antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligonucleotide A similar procedure for in vivo use is described in WO 91/15580. Briefly, a pair of oligonucleotides for a given antisense RNA is produced as follows: A sequence complimentary to the first 15 bases of the open reading frame is flanked by an EcoRl site on the 5 end and a HindIII site on the 3 end. Next, the pair of oligonucleotides is heated at 90° C. for one minute and then annealed in 2X ligation buffer (20 mM TRIS HCl pH 7.5, 10 mM MgCl2, 10 MM dithiothreitol (DTT) and 0.2 mM ATP) and then ligated to the EcoRI/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the an, used for replication and expression in vertebrate cells. Expression of the sequence encoding a polypeptide of the invention, or fragments thereof, can be by any promoter known in the art to act invertebrate, preferably fly cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from b to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1999), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl, Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species. Such a use could affect an organisms ability (e.g., a fly, Drosophila, etc.) to be resistant to particular infections or ailments due to aberrations in a biotic association.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, fly hosts have symbiosis with enteric bacteria in their gastrointestinal tracts, or gut. Such symbiosis, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

The composition of the gut flora, for example, is based upon a variety of factors, which include, but are not limited to, the age, strain, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

In a preferred embodiment, a polynucleotides and polypeptides, including agonists, antagonists, and fragments thereof, are useful for inhibiting biotic associations with specific enteric symbiont organisms in an effort to control the population of such organisms.

Pheromones

In another embodiment, a polynucleotide or polypeptide and/or agonist or antagonist of the present invention may increase the organisms ability to synthesize, release, and/or respond to a pheromone, either directly or indirectly. Such a pheromone may, for example, alter the organisms behavior and/or metabolism. Such a use could profoundly influence an organisms ability (e.g., fly, Drosophila, etc.) to reproduce, an potentially increase its life cycle. The latter would be useful for creating new strains of organisms (e.g., transgenic Drosophila which constitutively or inducible express a polypeptide of the present invention) which are useful in ascertaining biological pathways, etc.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones, either directly or indirectly. Preferably, any of the pheromones, and/or volatiles released from the organism, or induced, by a polynucleotide or polypeptide and/or agonist or antagonist of the invention have behavioral effects on the organism.

References

Aderem A, Ulevitch R. J., Nature. 2000 Aug 17;406 (6797):782–7. Toll-like receptors in the induction of the innate immune response.

Anderson KV, Jurgens G, Nusslein-Volhard C., Cell. 1985 Oct;42(3):779–89. Establishment of dorsal-ventral polarity in the Drosophila embryo: genetic studies on the role of the Toll gene product.

Banner D W, D'Arcy A, Janes W, Gentz R, Schoenfeld H J, Broger C, Loetscher H, Cell 1993 May 7;73(3):431–45. Crystal structure of the soluble human 55 kd TNF receptor-human TNF beta complex: implications for TNF receptor activation, Belvin M and Anderson K. V., Annu Rev Cell Dev Biol (1996) 12: 393–416. A conserved signaling pathway: The Drosophila Toll:Dorsal pathway.

Brand A H, Perrimon N., Development. 1993 Jun;118(2):401–15. Targeted gene expression as a means of altering cell fates and generating dominant phenotypes.

Hay B A, Wolff T, Rubin G M, Development. 1994 Aug;120(8):2121–9. Expression of baculovirus P35 prevents cell death in Drosophila.

Hotamisligil G S, Shargill N S, Spiegelman B M, Science 1993 Jan 1;259(5091):87–91. Adipose expression of tumor necrosis factor-alpha: direct role in obesity-linked insulin resistance.

Khush, R. and Lemaitre, B. , Trends Genet. (2000) 16:442–449. Genes that fight infection: what the Drosophila genome says about animal immunity.

Lemaitre B, Nicolas E, Michaut L, Reichhart J M., Hoffmann J A., Cell. 1996 Sep 20;86(6)973–83. The dorsoventral regulatory gene cassette spatzle/Toll/cactus controls the potent antifungal response in Drosophila adults.

Locksley R M, Killeen N., and M J Lenardo, Cell (2001) Vol. 104, 487–501. The TNF and TNF Receptor Superfamilies: Integrating Mammalian Biology.

Maini R N, Taylor P C., Annu Rev Med. 2000;51:207–29. Anti-cytokine therapy for rheumatoid arthritis.

Matthews D J and Kopczynski J, Drug Discovery Today 2001 6(3) 141–149. Using model-system genetics for drug-based target discovery Margolis J, Duyk G., Nat Biotechnol. 1998 Apr;16(4):311. The emerging role of the genomics revolution in agricultural biotechnology.

Ollmann M, Young L M, Di Como C J, Karim F, Belvin M, Robertson S, Whittaker K, Demsky M, Fisher W W, Buchman A, Duyk G, Friedman L, Prives C, Kopczynski C. Cell, 2000 Mar 31;101(1):91–101. Drosophila p53 is a structural and functional homolog of the tumor suppressor p53.

Papadakis K A, Targan S. R., Inflamm Bowel Dis. 2000 Nov;6(4):303–13. The role of chemokines and chemokine receptors in mucosal inflammation.

Roberts, D. (1998) Drosophila: A practical approach (Second Ed.) Oxford Univ. Press.

Rubin G M, Spradling A C, Science. 1982 Oct 22;218 (4570):348–53. Genetic transformation of Drosophila with transposable element vectors.

Smith C A, Farrah T, Goodwin R G., Cell, 1994 Mar 25; 76(6):959–62. The TNF receptor superfamily of cellular and viral proteins: activation, costimulation, and death.

Tautz D, Pfeifle C., Chromosoma. 1989 Aug;98(2):81–5. A non-radioactive in situ hybridization method for the localization of specific RNAs in Drosophila embryos reveals translational control of the segmentation gene hunchback.

Tracey K J, Cerami A., Annu Rev Med. 1994;45:491–503. Tumor necrosis factor: a pleiotropic cytokine and therapeutic target.

Vassalli P, Annu Rev Immunol. 1992;10:411–52. The pathophysiology of tumor necrosis factors.

EXAMPLE 1

Identification of the Novel DmTNF Polynucleotides

DmTNF was identified by homology searches using the amino acid sequence of the TNF domain corresponding to the human Osteoprotegeron Ligand protein (OPGL) (SEQ ID NO:7) as a query against the public Drosophila genome sequence database. The BLAST2 algorithm was used for the searches (Altschul, S. F., Madden, T. L., Schaffer, A. A., Zhang, J., Zhang, Z., Miller, W., and Lipman, D. L., Nucleic Acid Res. 25, 3389–3402 (1997)). A conserved TNF domain was found in the public Drosophila genome database (contig AC005974; Genbank Accession No: AC005974).

The Drosophila genomic sequence AC005974 contains both coding and noncoding DNA sequences. The BLAST2 output only described a portion of the AC005974 coding region that matched to the OPGL molecule (see FIG. 5). To find out more information about the rest of the Drosophila TNF containing molecule (DmTNF), a gene prediction program called FGENESH was run on nucleotide sequence of AC005974. A putative gene was found in the sequence of AC005974 that was determined to contain the TNF domain. This putative gene sequence was 2166 nucleotide in length, encoding a putative protein of 409 amino acids (see FIGS. 1A–C; SEQ ID NO:1). This sequence is referred to as DmTNF herein.

This genomic DNA sequence analysis further suggested that there was a TNF domain containing molecule in the Drosophila genome. To confirm this finding, further research was conducted to clone the DmTNF cDNA. The short open reading frame corresponding to DmTNF was found to reside in region 46E1–46F6 on chromosome 2. No ESTs corresponding to this region were found in the Berkeley Drosophila Genome Project database (BDGP; http://www.fruitfly.org/blast/). However, the sequence was BLASTed through the Exelixis FlyTag database and found to match the FlyTag assembly c39638 (FlyTag™, Exelixis Pharmaceuticals, Inc. South San Francisco, Calif.). The region corresponding to the predicted DmTNF sequence within this assembly was determined to contain an open reading frame. The predicted polynucleotide sequence from this open reading frame, based upon the use of bioinformatic methods, is shown in FIGS. 2A–B (SEQ ID NO:3) and is referred to as DmTNFvl. The DmTNFvl polynucleotide sequence was then BLASTed against the Genbank database leading to the identification of Drosophila EST LP03784 (SEQ ID NO:10). The clone corresponding to EST LP03784 was purchased from Research Genetics (Huntsville, Ala.). Sequencing of the LP03784 clone suggested that it encoded a full-length bone fide TNF molecule (See FIGS. 3A–C; SEQ ID NO:5). The clone corresponding to this latter sequence is referred to as DmTNFv2. The DmTNF2 clone is believed to represent the true physiological form of the DmTNF gene, and was thus chosen for functional characterization as described herein.

EXAMPLE 2

Whole Mount RNA In Situ Hybridization of Drosophila Embryos Suggest that DmTNF is Negatively Regulated by Activation of Rel Proteins.

Dorsal/ventral embryonic patterning as an established model for Rel protein signaling in Drosophila represents an area of significant scientific interest. To date, all components found in this system have counterparts in mammalian systems (review see Khush, R, and Lemaitre, B. (2000) Trends in Genet. 16: 442–449). Evidence of a Rel protein signaling cascade in Drosophila was first discovered in screens for maternally expressed genes involved in embryonic dorsal/ventral polarity (reviewed by Belvin, and Anderson, K. (1996) Annu Rev Cell Dev Biol 12: 393–416.) The Dorsal gene encoded a Rel protein that was found in the cytoplasm of all cells of the early embryo. Activation of the Toll receptor in the ventral cells of the embryo caused a signal-dependent movement of the Dorsal protein to the nucleus where a ventral specific transcriptional program was activated. It has been shown that the components of the Toll-Dorsal signaling pathway are an essential part of the Drosophila innate immune response (Lemaitre et al., (1996) Cell 86:973–983). Furthermore, Toll-like receptors and activation of the Rel pathway are essential in the induction of the mammalian innate immune response (reviewed by Aderem, A. and Ulevitch, R. (2000) Nature 406:782–787).

Gene expression of DmTNF of the present invention was tested by in situ hybridization using DmTNF mRNA at several time points of embryonic development using the methods essentially as provided in Tautz D, Pfeifle C. Chromosoma., 98:81–5 (1989). The Fly LP03784 clone (SEQ ID NO:1) containing the full length DmTNF was linearized with EcoRl restriction enzyme and cRNA probe was generated using Sp6 polymerase and Dig RNA labeling kit (Cat. No. 1 175 025, Roche Molecular Biochemicals, Mannheim, Germany). The results indicate that DmTNF gene expression is upregulated in the dorsal region of the developing embryo (stage 4/5) at a time coincident with the activation of Rel activity in the ventral region only (as shown in FIG. 8). Also, expression was observed in mesoderm specific tissues at stage 10 of embryonic development. Thus, suggesting that DmTNF is negatively regulated by activation of Rel proteins.

EXAMPLE 3

Expression Profiling of Novel Drosophila Tumor Necrosis Factor Homolog, DmTNF

The steady-state DmTNF mRNA expression levels were analyzed by quantitative PCR using the standard SYBR Green PCR and RT-PCR reagent protocol according to the manufacturers instructions (PE Applied Biosystems, Foster City, Calif.). Briefly, polyA+ DmTNF mRNA from Drosophila embryos, larvae, and adult (Clontech. Palo Alto, Calif.) was isolated and subjected to real-time quantitative PCR using a PE 5700 instrument (Applied Biosystems, Foster City, Calif.) which detects the amount of DNA amplified during each cycle by the fluorescent output of SYBR green, a DNA binding dye specific for double strands. Reverse trancription (RT) reactions contained 15 ng mRNA per reaction. Random Hexamer was used for all RT reactions. 2 ul of the RT reaction was added to a PCR amplification mixture containing the template and primers in 50 ul. DmTNF primers were added to a final concentration of 600 nm each. Internal control rp49 gene primers were added to a final concentration of 300 nm each. PCR primer pairs directed to DmTNF as follows:

```
DmTNF-          ACCAGAACGGATTTATCGTCTTTC (SEQ ID NO:11)
forward primer

DmTNF-reverse   GTTGGTGGGCACCGTGTT       (SEQ ID NO:12)
primer
```

The specificity of the primer pair for its target was verified by performing a thermal denaturation profile at the end of the run which gave an indication of the number of different DNA sequences present by determining melting Tm. In the case of the DmTNF primer pair, only one DNA fragment was detected having a homogeneous melting point. Contributions of contaminating genomic DNA to the assessment of tissue abundance was controlled by performing the PCR with a first strand made with and without reverse transcriptase. In all cases, the contribution of material amplified in the reverse transcriptase controls was negligible. Small variations in the amount of cDNA used in each tube was determined by performing a parallel experiment using a primer pair for a gene expressed in equal amounts in all tissues, the *Drosophila* rp49 gene. Primer pairs for rp49 were as follows:

```
Rp49 forward    GACCATCCGCCCAGCATAC (SEQ ID NO:13)
primer

Rp49 reverse    ACTGGTGGCGGATGAAGTG (SEQ ID NO:14)
primer
```

These data were used to normalize the data obtained with the DmTNF primer pair. The PCR data was converted into a relative assessment of the difference in transcript abundance amongst the tissues tested and the data are presented in bar graph form. Transcripts corresponding to DmTNF are expressed highly in *Drosophila* embryos and larvae, with lower levels observed in adult tissue (as shown in FIG. 10).

EXAMPLE 4

Functional Analysis of DmTNF Polypeptides

The goal of these experiments is to identify a biological function of the DmTNF polypeptides of the present invention. In these experiments, Rel signaling in embryos is "turned off" by using Dorsal (rel protein) recessive mutant animals (dl1 mutants) that have no Dorsal function, and constitutively activate Rel signaling by using dominant activated Toll mutants (Tl3) (Anderson et al., (1985) Cell 42: 791–798). In these mutant backgrounds DmTNF levels are measured by in situ hybridization methods (same as Example 2). Fly culture and crosses were preformed according to standard protocols at placed at 25 degrees Celsius (Roberts, D. (1998) *Drosophila:* A practical approach). Genetic crosses obtained embryos from dl1 homozygous mutant females mated to mutant and nonmutant males. Embryos laid by those females lack d1 function and their embryos were collected for in situ hybridization. In the case of Tl3 mutants, genetic crosses consisted of males with the genotype mwh1 kniri-1 snk4 red1 e1 Tl3cal/Ms(3)R241/TM3, Sbl, and cross to female from Toll deficiency Df(3R) Tl-P, e1 cal/TM3, Ser1. In F1, collect females with mwh1 kniri-1 snk4 red1 e1 Tl3 ca1/TM3, Ser1. Collect their embryos for in situ hybridization (*Drosophila* mutants are publicly available through FlyBase, Bloomington, Ind.).

The results of genetic studies demonstrate the DmTNF is negatively regulated by the Rel activation pathway in embryogenesis. DmTNF is expressed only in areas where Rel proteins are not activated (see FIG. 8). This has been confirmed in mutant genetic studies, for example, in well-characterized Dorsal (Rel protein) loss of function mutants DmTNF is expressed throughout the embryo (see FIG. 9). Conversely, DmTNF gene expression is lost in constitutively active Toll receptor mutant where Dorsal is ubiquitously activated. Taken together, there is strong genetic evidence for the negative regulation of DmTNF via active Rel signal transduction.

EXAMPLE 5

The Mis-Expression of DmTNF Proteins

Low levels of overexpression of DmTNF in transgenic flies leads to lethality. Transgenic flies were generated using the Gal4/ UAS modular system (Brand, A. and Perrimon, N., Development. 1993 June;118(2):401–15.) DmTNF overexpression constructs were made by subcloning LD03784 cloned into a vector (pExpress-UAS) containing UAS-Gal4 binding sites upstream of a heat shock promoter (Ollman, M. (2000) Cell 101:91–101). Standard P-element-mediated germline transformation was used to generate 3 transgenic lines containing this construct (Rubin and Spradling, Science. 1982 Oct. 22;218(4570):348–53). UAS-DmTNF transgenic *Drosophilia* were crossed to flies containing an eye-development enhancer repeats. The pExpress vector is an adapted version of the pGMR which contains an alpha tubulin 3'UTR for increased protein stabilization and a modified multiple cloning site (Ollman, M. (2000) Cell 101:91–101). Transgenic flies were created from genetic crosses of UAS-DmTNF transgenic flies containing the GMR eye specific enhancer and heat shock promoter (Hay et al., (1994) Development 120:2121–2129) to express the GAL4 protein.

EXAMPLE 6

Cloning and Expression of dmTNF/mouse CD8 Fusion Protein

In order to express a soluble form of DmTNFv2 for functional studies, cDNA fragments encoding the predicted extracellular region of DmTNFv2 were obtained by PCR and cloned into a vector containing the coding sequence of the extracellular region of mouse CD8/Lyt2a (Hollenbaugh D, Grosmaire L S, Kullas C D, Chalupny N J, Braesch-Andersen S, Noelle, R J, Stamenkovic I, Ledbetter J A, Aruffo A., EMBO J Dec;11(12):4313–21, (1992)).

The oligonucleotide primers used for PCR were as follows:

```
DmTNFv2 5'    CGGAAAGATCTAACGCGTGTATCGCATCTGGACAAG (SEQ ID NO:21)
Primer

DmTNFv2 3'    GCCTCTAGAAATTTACACCTTGAAGATGCC        (SEQ ID NO:22)
Primer
```

Clontech Advantage polymerase was used according to the manufacturer's instructions. Approximately 0.4 ng of pBS-dmTNF plasmid was used as template in a 50 ul PCR reaction using the following cycling conditions: 1 cycle at 94° C./3 min., 55° C./1 min., 72° C./1 min; 22 cycles 94° C./1 min., 57° C./1 min. and a final elongation step at 72° C. for 5 min. The PCR products were digested with Bgl II and Xba I and ligated into BamHI and XbaI digested pCDM8 or pD18 vectors which encoded the mouse CD8 fusion partner. The DmTNF encoding region of the resulting vectors were sequenced to verify the absence of mutations. Proteins were expressed in COS cells that were transiently transfected with the vectors using the DEAE-dextran (Hollenbaugh, D and A. Aruffo., in Current Protocols in Immunology (Coligan, J E, Kruisbeek, A M, Marqulies, D H, Shevach, E M and Strober, W, eds) pp 10.19.1–10.19.11, John Wiley & Sons, Inc., Washington D.C. (1994)).

After overnight culture, the transfected cells were grown for an additional 24 h in the presence of $^{35}$S-Cys/Met containing medium. Proteins from the supernatant were immunoprecipitated with rat anti-mCD8 mAb 53-6 (Roche Biochemicals) and Protein A Sepharose beads. The precipitated proteins were separated by SDS-PAGE on an 8–16% gradient gel. After fixation and drying, the gel was exposed to film (see FIG. 12).

One skilled in the art could easily modify the exemplified studies to test the activity of polynucleotides of the invention, agonists, and/or antagonists of polynucleotides or polypeptides of the invention.

EXAMPLE 7

Generation of Anti-DmTNF Antibodies

Anti-DmTNF rabbit polyclonal and mouse monoclonal antibodies can be generated using standard methods by generating and purifying a full-length DmTNF protein fused to glutathione-S-transferase (GST) as antigen, for example. The DmTNF/mouse CD8/Lyt2a fusion protein described in Example 6 herein could also be used. Inclusion bodies of such a fusion peptide could then be purified by centrifugation using B-PER buffer (Pierce, Rockford, Ill.) and injected subcutaneously into rabbits and mice for immunization. A final boost for mouse monoclonal antibody production could be obtained via an intravenous injection of soluble GST-DmTNF produced by solubilization of GST-DmTNF in 6M GuHCI and dialysis into phosphate buffer containing 1M NaCI, if required. The DmTNF/mouse CD8/Lyt2a fusion protein of the present invention is soluble and would likely not require use of 6M GuHCl for solubilization. Hybridoma supernatants could then be screened by ELISA using a soluble 6XHIS-tagged DmTNF protein bound to Ni-NTA coated plates (Qiagen, Valencia, Calif.) and an anti-mouse IgG Fc-fragment specific secondary antibody.

Aside from the methods summarized above for creating anti-DmTNF antibodies, the following methods may also be utilized. The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in other organisms, it may be desirable to use antibodies that have been either modified or engineered to not elicit an immune response within the host organisms. For example, it would be desirable to use "humanized" chimeric anti-DmTNF monoclonal antibodies in humans. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant. An additional method of generating anti-DmTNF antibodies would be through the isolation of antibody fragments directed against DmTNF from a library of scFvs. Naturally occurring V-genes isolated from an organisms PBLs (e.g., human) are constructed into a library of antibody fragments which contain reactivities against DmTNF to which the donor may or may not have been exposed (see e.g., U.S. Pat. No. 5,885,793 incorporated herein by reference in its entirety).

Rescue of the Library. A library of scFvs is constructed from the RNA of the organisms PBLs (e.g., human) as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding of antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

EXAMPLE 8

DmTNF RNA Interference (RNAi) Experiments in Cell Culture

One exemplary method of assessing the biological function of a particular polypeptide in through the administration of antisense oligonucleotides directed against the mRNA of said polypeptide to either an organism or cell culture. Successful application of antisense oligonucleotides is often difficult in most organisms due to the presence of endogenous and/or systemic nucleases which act to degrade the administered oligonucleotides. The same is true for cells grown in cell culture. However, expression of double stranded RNA in transfected *Drosophila* cell lines does not appear to have the same limitations as in other organisms—thus enabling facile determination of biological function using antisense-based methodology. The application of RNAi in assessing the biological function of DmTNF is therefore encompassed by the present invention. Briefly, Preparation of the dsRNA template: PCR primers containing an upstream T7 RNA polymerase binding site and downstream DmTNF gene sequences could be designed such that the sequence could be amplified in a manner that would allow the generation of a DmTNF-derived dsRNA. PCR reactions could be performed using EXPAND High Fidelity (Boehringer Mannheim, Indianapolis, Ind.), for example, and the amplified products then purified.

DmTNF RNA could be generated from the PCR template using the Promega Large Scale RNA Production System (Madison, Wis.) following manufacturer's protocols. Ethanol precipitation of RNA would be performed and the RNA annealed by a first incubation at 68 C. for 10 min, followed by a second incubation at 37 C. for 30 min. The resulting dsRNA would then be stored at −80 C.

RNAi experiment in tissue culture: RNAi could be performed essentially as described previously (http://dixonlab. biochem. med. umich.edu/protocols/RNAiExpetiments. html). On day 1, cultures of *Drosophila* S2 cells are obtained that express pMT-HA-DmTNF expression plasmid and either 15 ptg of DmTNF dsRNA or no RNA is added to the medium. On the second day, CuSO4 is added to final concentrations of either 0, 7, 70 or 700 RM to all cultures. On the fourth day, an alamarBlue (Alamar Biosciences Inc., Sacramento, Calif.) staining assay is performed to measure the number of live cells in each culture, by measuring fluorescence at 590 nm.

EXAMPLE 9

Method of Creating N- and C-terminal Deletion Mutants Corresponding to the DmTNF, DmTNFv1, and DmTNFv2 Polypeptides of the Present Invention As described elsewhere herein, the present invention encompasses the creation of N- and C-terminal deletion mutants, in addition to any combination of N- and C-terminal deletions thereof, corresponding to the DmTNF, DmTNFv1, and DmTNFv2 polypeptides of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length DmTNF, DmTNFv1, or DmTNFv2 polypeptide sequence (as described in Example 9, for example), appropriate primers of about 15–25 nucleotides derived from the desired 5' and 3' positions of SEQ ID NO:1, SEQ ID NO:3, or SEQ ID NO:5 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the DmTNF I53 to V409 N-terminal deletion mutant, the following primers could be used to amplify a cDNA fragment corresponding to this deletion mutant:

```
5' Primer  5'-GCAGCAGCGGCCGCATTCTCGCACTAACGATCTGGCAG-3'  (SEQ ID NO:22)
              NotI 3' Primer  5'-GCAGCAGTCGACCACCTTGAAGATGCCAAAGTAGC-3'     (SEQ ID NO:23)
              SalI
```

For example, in the case of the DmTNF M1 to V315 C-terminal deletion mutant, the following primers could be used to amplify a cDNA fragment corresponding to this deletion mutant:

```
5' Primer  5'-GCAGCAGCGGCCGCATGACTGCCGAGACCCTCAAGCCG-3'  (SEQ ID NO:24)
              NotI 3' Primer  5'-GCAGCAGTCGACTACGCCATCGCGCGTTTGAAAGTG-3'    (SEQ ID NO:25)
              SalI
```

For example, in the case of the DmTNFv1 I53 to V406 N-terminal deletion mutant, the following primers could be used to amplify a cDNA fragment corresponding to this deletion mutant:

```
5' Primer  5'-GCAGCAGCGGCCGCATTCTCGCACTAACGATCTGGCAG-3'  (SEQ ID NO:22)
              NotI 3' Primer  5'-GCAGCAGTCGACCACCTTGAAGATGCCAAAGTAGC-3'     (SEQ ID NO:23)
              SalI
```

For example, in the case of the DmTNFv1 M1 to V312 C-terminal deletion mutant, the following primers could be used to amplify a cDNA fragment corresponding to this deletion mutant:

```
5' Primer 5'-GCAGCAGCGGCCGCATGACTGCCGAGACCCTCAAGCCG-3'  (SEQ ID NO:24)
             NotI 3' Primer 5'-GCAGCAGTCGACGACGCCATCGCGCGTTTGAAAGTG-3'    (SEQ ID NO:25)
             SalI
```

For example, in the case of the DmTNFv2 I53 to V409 N-terminal deletion mutant, the following primers could be used to amplify a cDNA fragment corresponding to this deletion mutant:

```
5' Primer 5'-GCAGCAGCGGCCGCATTCTCGCACTAACGATCTGGCAG-3'  (SEQ ID NO:22)
             NotI 3' Primer 5'-GCAGCAGTCGACCACCTTGAAGATGCCAAAGTAGC-3'     (SEQ ID NO:23)
             SalI
```

For example, in the case of the DmTNFv2 M1 to L316 C-terminal deletion mutant, the following primers could be used to amplify a cDNA fragment corresponding to this deletion mutant:

```
5'     5'-GCAGCAGCGGCCGCATGACTGCCGAGACCCTCAAGCCG-3'     (SEQ ID NO:24)
Primer NotI 3'     5'-GCAGCAGTCGACCAAGACGCCATCGCGCGTTTGAAAG-3'      (SEQ ID NO:25)
Primer SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of K+betaM5), 200 uM 4dNTPs, 1 uM primers, 0.25 U Taq DNA polymerase (PE), and standard Taq DNA polymerase buffer. Typical PCR cycling condition are as follows:

| | |
|---|---|
| 20–25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula:

$(S+(X*3))$ to $((S+(X*3))+25)$, wherein 'S' is equal to the nucleotide position of the initiating start codon of the DmTNF, DmTNFv1, or DmTNFv2 gene (SEQ ID NO:1, 3, or 5), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to the sense strand of SEQ ID NO:1, 3, or 5 as appropriate. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

$(S+(X*3))$ to $((S+(X*3))-25)$, wherein 'S' is equal to the nucleotide position of the initiating start codon of the DmTNF, DmTNFv1, or DmTNFv2 gene (SEQ ID NO:1, 3, or 5), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, 3, or 5 as appropriate. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

EXAMPLE 10

Regulation of Protein Secretion Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression e.g., tetracycline or rapamycin) (see, D. Bohl, et.al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promoter and signal sequence, independent from the other, could be either the endogenous promoter or signal sequence of a polypeptide of the present invention, or alternatively, could be a heterologous signal sequence and promoter.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

EXAMPLE 11

Alteration of Protein Glycosylation Sites to Enhance Secretion Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexamnder and Elder (1984), Science, 226:1328–1330; and Flack et al., (1994), J. Biol. Chem., 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intraceullular accumulation of glycosylation site variants (Machamer and Rose (1988), J. Biol Chem., 263:5955–5960; Gallagher et al., (1992), J. Viology., 66:7136–7145; Collier et al., (1993), Biochem., 32:7818–7823; Claffey et al., (1995) Biochemica et Biophysica Acta, 1246:1–9; Dube et al., (1988), J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E.coli, yeast, or viral organisms; or an E.coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics) or Motifs computer program (GCG Suite of programs). Once identified, the sites could be systematically deleted, or impaired, at the level of the DNA using mutagenesis methodology known in the art and available to the skilled artisan, preferrably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

EXAMPLE 12

Method of Enhancing the Biological Activity/ Functional Characteristics of Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Keat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91;10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatman) or could be purified using Microcon concentrators (Amicon) of the appropriate molecular weight cuttoff, or could use oligonucleotide purification columns (Qiagen), in addition to other methods known in the art. If using DE81 ion-exchange paper, the 10–50 bp fragments could be eluted from said paper using 1M NaCL, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris•HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C. for 60 s; 94 C. for 30 s, 50–55 C. for 30 s, and 72 C. for 30 s using 30–45 cycles, followed by 72 C. for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C. for 30 s, 50 C. for 30 s, and 72 C. for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then selected for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

EXAMPLE 13

Method of Determining Alterations in a Gene Corresponding to a Polynucleotide

RNA isolated from multiple flies from the same strain or individual flies presenting with a phenotype of interest (such as a disease) is to be isolated. cDNA is then generated from these RNA samples using protocols known in the art. (See, Sambrook.) The cDNA is then used as a template for PCR, employing primers surrounding regions of interest in SEQ ID NO:1, 3, or 5. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Isolated or engineered genomic clones are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tuczon, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.). Chromosome alterations of the genomic region hybridized by the probe are identified as insertions, deletions, and translocations. These alterations are used as a diagnostic marker for an associated disease.

EXAMPLE 14

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphate conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

EXAMPLE 15

Method of Isolating A Specific Clone.

In the case of DmTNFv2, two approaches can be used to isolate a particular clone from a sample of plasmid DNA(s). First, a plasmid is directly isolated by screening the clones using a polynucleotide probe corresponding to SEQ ID NO:5.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the at, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:5 (i.e., within the region of SEQ ID NO:5 bounded by the 5' NT and the 3' NT of the clone defined in Table 1) are synthesized and used to amplify the desired cDNA using the cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C for 1 min; annealing at 55 degree C for 1 min; elongation at 72 degree C for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

In the case of DmTNF and DmTNGv1, an isolated clone may be created using a combination of cloning and mutagenesis techniques within the skill of the trained artisan. Briefly, a clone corresponding to the DmTNF polynucleotide sequence (SEQ ID NO:1) could be created by site directed mutagenesis techniques using DmTNFv2 as a template. Likewise, a clone corresponding to the DmTNFv1 polynucleotide sequence (SEQ ID NO:3) could also be created by site directed mutagenesis techniques using DmTNFv2 as a template. Design of applicable primers and methods are known in the art (see for example, Mullis et al., Cold Spring Harbor Symp. Quant. Biol., 51:263, (1987), Ehrlich (ed), PCR Technology, Stockton Press, N.Y., 1989; Ehrlich et al., Science, 252:1643–1650, (1991); and "PCR Protocols, A Guide to Methods and Applications", Eds., Innis et al., Academic Press, New York, (1990). The mutatgenesis techniques, which may include, additions, deletions, frameshifts, substitutions, etc., of specific nucleotides, would be continued until the cloned sequence matched the polynucleotide sequence provided for DmTNF (FIGS. 1A–C; SEQ ID NO:1), or for DmTNFv1 (FIGS. 2A–B; SEQ ID NO:3).

EXAMPLE 16

Bacterial Expression of a Polypeptide.

A polynucleotide encoding a polypeptide of the present invention is amplified using PCR oligonucleotide primers corresponding to the 5' and 3' ends of the DNA sequence to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000Xg). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., spra). Proteins with a 6×His tag bind to the Ni-NTA resin with high affinity and can be purified in a simple one-step procedure (for details see: The QIA expressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM solution acetate pH 6 buffer plus 200 mM NaCl. The purified protein is stored at 4 degree C or frozen at −80 degree C.

EXAMPLE 17

Cloning and Expression of a Polypeptide in a Baculovirus Expression System.

In this example, the plasmid shuttle vector pAc373 is used to insert a polynucleotide into a baculovirus to express a polypeptide. A typical baculovirus expression vector contains the strong polyhedrin promoter of the Autographa californica nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence to synthesize insertion fragments. The primers used to amplify the cDNA insert should preferably contain restriction sites at the 5' end of the primers in order to clone the amplified product into the expression vector. Specifically, the cDNA sequence contained in the clone, including the AUG initiation codon and the naturally associated leader sequence identified elsewhere herein (if applicable), is amplified using the PCR protocol described in Example 9. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as Xl-1 Blue (Stratagene Cloning Systems, La Jolla, Calif.) cells are transformed with the ligtation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized bacuolvirus DNA ("BaculoGoldtm baculovirus DNA", Pharmingen, San Diego, Calif.), using the lipofection method described by Felgner et al., Proc. Natl. Acad. Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologoes Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gathersburg, page 9–10). After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available for Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

EXAMPLE 18

Expression of a Polypeptide in Mammalian Cells.

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) Murphy et al., Biochem J. 227:277–279 (1991); Bebbington et al., Bio/Technology 10:169–175 (1992). Using these markers, the mammalian cells are grown in selective medium and the cells with the highest resistance are selected. These cells lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Holla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Although the present invention has been described in some detail by way of illustration and example for purposes of clarity and understanding, it will be apparent that certain changes and modifications may be practiced within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

We claim:

1. An isolated nucleic acid molecule comprising a polynucleotide sequence selected from the group consisting of:
   (a) an isolated polynucleotide encoding a polypeptide comprising amino acids 1 to 409 of SEQ ID NO:6;
   (b) an isolated polynucleotide encoding a polypeptide comprising amino acids 2 to 409 of SEQ ID NO:6;
   (c) an isolated polynucleotide encoding a mature polypeptide comprising amino acids 53 to 409 of SEQ ID NO:6; and
   (d) an isolated polynucleotide which represents the complementary sequence of (a), (b), or (c).

2. The isolated nucleic acid molecule of claim 1, wherein said polynucleotide is (a).

3. The isolated nucleic acid molecule of claim 2, wherein said polynucleotide comprises nucleotides 634 to 1860 of SEQ ID NO:5.

4. The isolated nucleic acid molecule of claim 1, wherein said polynucleotide is (b).

5. The isolated nucleic acid molecule of claim 4, wherein said polynucleotide comprises nucleotides 637 to 1860 of SEQ ID NO:5.

6. The isolated nucleic acid molecule of claim 1, wherein said polynucleotide is (c).

7. The isolated nucleic acid molecule of claim 6, wherein said polynucleotide comprises nucleotides 790 to 1860 of SEQ ID NO:5.

8. The isolated nucleic acid molecule of claim 1, wherein said polynucleotide is (d).

9. A recombinant vector comprising a member of the group consisting of the isolated nucleic acid molecule of claim 1(a), (b), and (c).

10. A recombinant host cell comprising the vector sequence of claim 9.

11. A method of making an isolated polypeptide comprising:
    (a) culturing the recombinant host cell of claim 10 under conditions such that said polypeptide is expressed; and
    (b) recovering said polypeptide.

12. The isolated polynucleotide of claim 1 wherein said nucleic acid sequence further comprises a heterologous nucleic acid sequence.

13. The isolated polynucleotide of claim 12 wherein said heterologous nucleic acid sequence encodes a heterologous polypeptide.

14. The isolated polynucleotide of claim 13 wherein said heterologous polypeptide is the Fc domain of immunoglobulin.

15. A recombinant vector comprising the isolated nucleic acid molecule of claim 1(d).

16. A recombinant host cell comprising the vector sequence of claim 15.

17. An isolated polynucleotide encoding a polypeptide comprising amino acids 62 to 409 of SEQ ID NO:6.

18. The isolated nucleic acid molecule of claim 17, wherein said polynucleotide comprises nucleotides 817 to 1860 of SEQ ID NO:5.

19. The isolated nucleic acid molecule of claim 17, wherein said polynucleotide further comprises a polynucleotide encoding the extracellular region of the mouse CD8/Lyt2a polypeptide.

20. The isolated nucleic acid molecule of claim 18, wherein said polynucleotide further comprises a polynucleotide encoding the extracellular region of the mouse CD8/Lyt2a polypeptide.

21. An isolated polynucleotide encoding a polypeptide comprising at least 332 contiguous amino acids of the polypeptide provided as SEQ ID NO:6, wherein said polynucleotide encodes a polypeptide that induces apoptosis in a cell in which said polypeptide is recombinately expressed.

22. The isolated polynucleotide of claim 21, comprising at least 996 contiguous nucleotides of the polynucleotide sequence provided as SEQ ID NO:5.

* * * * *

UNITED STATES PATENT AND TRADEMARK OFFICE
CERTIFICATE OF CORRECTION

PATENT NO. : 7,037,676 B2  Page 1 of 1
APPLICATION NO. : 09/813329
DATED : May 2, 2006
INVENTOR(S) : Pamela M. Carroll et al.

It is certified that error appears in the above-identified patent and that said Letters Patent is hereby corrected as shown below:

Title Page Item (54)

Add -- ("DmTNFv2") -- after "MOLECULE"

The title should now read:

-- DROSOPHILA TUMOR NECROSIS FACTOR CLASS MOLECULE ("DmTNFv2")
        POLYNUCLEOTIDES AND VARIANTS THEREOF --

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,037,676 B2  Page 1 of 1
APPLICATION NO. : 09/813329
DATED : May 2, 2006
INVENTOR(S) : Pamela M. Carroll et al.

It is certified that error appears in the above-identified patent and that said Letters Patent is hereby corrected as shown below:

Title Page Item (54) and at Column 1, line 2

Add -- ("DmTNFv2") -- after "MOLECULE"

The title should now read:

-- DROSOPHILA TUMOR NECROSIS FACTOR CLASS MOLECULE ("DmTNFv2") POLYNUCLEOTIDES AND VARIANTS THEREOF --

This certificate supersedes the Certificate of Correction issued September 28, 2010.

Signed and Sealed this

Ninth Day of November, 2010

David J. Kappos
*Director of the United States Patent and Trademark Office*

SEQUENCE LISTING

<160> NUMBER OF SEQ ID NOS: 65

<210> SEQ ID NO 1
<211> LENGTH: 2166
<212> TYPE: DNA
<213> ORGANISM: Drosophila melanogastor
<220> FEATURE:
<221> NAME/KEY: CDS
<222> LOCATION: (652)..(1878)

<400> SEQUENCE: 1

| | |
|---|---|
| ccactgtgct gggaattcgg cacgaggcga acggacgttt aaagtgagaa agaaaccgg | 60 |
| taaatcagag atcccaagca agcgcgtgcg tgcatgatag cgaagaaaaa aagctatccg | 120 |
| tttcagttaa ctacttacca agattgaatt tcgccatcgg gcaaattact aaaaatacat | 180 |
| aagtgcaact cgtccactgt gtgttgtgtt ttttttttt ttttggttt tcgctgtgcc | 240 |
| tttatcgcaa acaagaactg ataaaactag aaaatatctt gagaaacttg ttttcgcgct | 300 |
| tttcttttgc taattgccga tcgcggaaga gaaaaacaag cagtagacaa aacaagtgtg | 360 |
| gtaatacaat ctgaaaaggg caccatcagc agcccgaggg gtttatctat atagatgtcg | 420 |
| cagcttatca tctcatgctg tctgtgaggt tgttctgtgt gctcgtgtag tatcttaaat | 480 |
| acatagagtg tgttcatata aagtgcgaca aagctcgatt ggaaacagct gtcgagtgcc | 540 |
| cttgagtggg tgggcaagat cgtcatcatc atcatcgtcg tcattatcaa cagaatcagc | 600 |
| atcagcatct ggaggccccg gatgctctaa gatcccagt gttcatcaat t atg act | 657 |
| | Met Thr |
| | 1 |

| | | | | | | | | | | | | | | | |
|---|---|---|---|---|---|---|---|---|---|---|---|---|---|---|---|
| gcc | gag | acc | ctc | aag | ccg | ttt | ata | acg | cca | acg | agt | gcc | aac | gat | gat | 705 |
| Ala | Glu | Thr | Leu | Lys | Pro | Phe | Ile | Thr | Pro | Thr | Ser | Ala | Asn | Asp | Asp | |
| | 5 | | | | 10 | | | | | 15 | | | | | | |

| ggt | ttt | ccg | gcc | aaa | gcg | acc | agc | acg | gcg | acc | gcc | cag | cga | cgc | acc | 753 |
|---|---|---|---|---|---|---|---|---|---|---|---|---|---|---|---|---|
| Gly | Phe | Pro | Ala | Lys | Ala | Thr | Ser | Thr | Ala | Thr | Ala | Gln | Arg | Arg | Thr | |
| 20 | | | | | 25 | | | | | 30 | | | | | | |

| cgc | cag | ctg | atc | ccc | ctg | gtt | ttg | ggg | ttc | atc | ggt | ctg | ggg | ctg | gtc | 801 |
|---|---|---|---|---|---|---|---|---|---|---|---|---|---|---|---|---|
| Arg | Gln | Leu | Ile | Pro | Leu | Val | Leu | Gly | Phe | Ile | Gly | Leu | Gly | Leu | Val | |
| 35 | | | | 40 | | | | | 45 | | | | | 50 | | |

| gtt | gcc | att | ctc | gca | cta | acg | atc | tgg | cag | aca | acg | cgt | gta | tcg | cat | 849 |
|---|---|---|---|---|---|---|---|---|---|---|---|---|---|---|---|---|
| Val | Ala | Ile | Leu | Ala | Leu | Thr | Ile | Trp | Gln | Thr | Thr | Arg | Val | Ser | His | |
| | | | | 55 | | | | | 60 | | | | | 65 | | |

| ctg | gac | aag | gag | ctg | aag | agc | ctg | aag | cga | gtc | gtc | gat | aat | ctc | cag | 897 |
|---|---|---|---|---|---|---|---|---|---|---|---|---|---|---|---|---|
| Leu | Asp | Lys | Glu | Leu | Lys | Ser | Leu | Lys | Arg | Val | Val | Asp | Asn | Leu | Gln | |
| | | | 70 | | | | | 75 | | | | | 80 | | | |

| cag | cgt | ttg | ggc | ata | aac | tat | ctg | gac | gag | ttc | gac | gag | ttc | caa | aag | 945 |
|---|---|---|---|---|---|---|---|---|---|---|---|---|---|---|---|---|
| Gln | Arg | Leu | Gly | Ile | Asn | Tyr | Leu | Asp | Glu | Phe | Asp | Glu | Phe | Gln | Lys | |
| | | 85 | | | | | 90 | | | | | 95 | | | | |

| gag | tac | gag | aat | gcc | ctc | atc | gac | tat | cca | aaa | aag | gtg | gat | ggc | ctc | 993 |
|---|---|---|---|---|---|---|---|---|---|---|---|---|---|---|---|---|
| Glu | Tyr | Glu | Asn | Ala | Leu | Ile | Asp | Tyr | Pro | Lys | Lys | Val | Asp | Gly | Leu | |
| | 100 | | | | | 105 | | | | | 110 | | | | | |

| acg | gat | gag | gag | gac | gac | gac | gat | ggc | gat | ggt | ctg | gat | tcc | att | gcg | 1041 |
|---|---|---|---|---|---|---|---|---|---|---|---|---|---|---|---|---|
| Thr | Asp | Glu | Glu | Asp | Asp | Asp | Asp | Gly | Asp | Gly | Leu | Asp | Ser | Ile | Ala | |
| 115 | | | | | 120 | | | | | 125 | | | | | 130 | |

| gac | gac | gag | gac | gac | gac | gtt | agc | tat | agc | tct | gtg | gat | gat | gtt | ggc | 1089 |
|---|---|---|---|---|---|---|---|---|---|---|---|---|---|---|---|---|
| Asp | Asp | Glu | Asp | Asp | Asp | Val | Ser | Tyr | Ser | Ser | Val | Asp | Asp | Val | Gly | |
| | | | | 135 | | | | | 140 | | | | | 145 | | |

| gca | gac | tac | gag | gac | tac | acc | gat | atg | tta | aat | aaa | ctc | aac | aat | gca | 1137 |
|---|---|---|---|---|---|---|---|---|---|---|---|---|---|---|---|---|
| Ala | Asp | Tyr | Glu | Asp | Tyr | Thr | Asp | Met | Leu | Asn | Lys | Leu | Asn | Asn | Ala | |
| | | | 150 | | | | | 155 | | | | | 160 | | | |

```
cat acc ggc acc acg ccc aca tct gag acc act gct gag ggc gag ggc      1185
His Thr Gly Thr Thr Pro Thr Ser Glu Thr Thr Ala Glu Gly Glu Gly
        165                 170                 175 gag acg gac agt gca tcc tca gcc tca aat gat gac aat gtg ttc gat      1233
Glu Thr Asp Ser Ala Ser Ser Ala Ser Asn Asp Asp Asn Val Phe Asp
    180                 185                 190 gac ttt acc agc tca gat gcc ctc aaa aag aag cag gag aga aaa tct      1281
Asp Phe Thr Ser Ser Asp Ala Leu Lys Lys Lys Gln Glu Arg Lys Ser
195                 200                 205                 210 cgc tcg att gcc gat gta cgc aat gag gag cag aat att caa gga aat      1329
Arg Ser Ile Ala Asp Val Arg Asn Glu Glu Gln Asn Ile Gln Gly Asn
            215                 220                 225 cac aca gag ctt cag gaa aag tca tcc aat gag gca gct tcc aaa gag      1377
His Thr Glu Leu Gln Glu Lys Ser Ser Asn Glu Ala Ala Ser Lys Glu
        230                 235                 240 agc cct gca gca ctt cac ctc cgt cgc aga atg cat tcc cgc cat cgc      1425
Ser Pro Ala Ala Leu His Leu Arg Arg Arg Met His Ser Arg His Arg
    245                 250                 255 cac ctc gta gtc cgc aaa gcc aga tcc gag gac tcg agg cca gca gcc      1473
His Leu Val Val Arg Lys Ala Arg Ser Glu Asp Ser Arg Pro Ala Ala
260                 265                 270 cat ttc cac ttg agc agc agg cgg cgt cac caa gaa agt atg ggc tac      1521
His Phe His Leu Ser Ser Arg Arg Arg His Gln Glu Ser Met Gly Tyr
275                 280                 285                 290 cat gga gat atg tac ata gaa aat gat agg gag aga tgc tct tat cag      1569
His Gly Asp Met Tyr Ile Glu Asn Asp Arg Glu Arg Cys Ser Tyr Gln
            295                 300                 305 gga cac ttt caa acg cgc gat ggc gta ttg acg gtg acc aat gca ggc      1617
Gly His Phe Gln Thr Arg Asp Gly Val Leu Thr Val Thr Asn Ala Gly
        310                 315                 320 cta tat tac gta tac gcc cag ata tgg ggc tac aac tcg cac gac cag      1665
Leu Tyr Tyr Val Tyr Ala Gln Ile Trp Gly Tyr Asn Ser His Asp Gln
    325                 330                 335 aac gga ttt atc gtc ttt caa gga gac act cca ttc ctg cag tgc ttg      1713
Asn Gly Phe Ile Val Phe Gln Gly Asp Thr Pro Phe Leu Gln Cys Leu
340                 345                 350 aac acg gtg ccc acc aac atg cca cat aag gtg cac acc tgc cac acg      1761
Asn Thr Val Pro Thr Asn Met Pro His Lys Val His Thr Cys His Thr
355                 360                 365                 370 agt ggt ctg atc cac ctg gaa cga aac gag agg atc cat ctg aag gac      1809
Ser Gly Leu Ile His Leu Glu Arg Asn Glu Arg Ile His Leu Lys Asp
            375                 380                 385 att cac aac gat cgc aat gca gtt ctg cgg gag gga aac aac cga agc      1857
Ile His Asn Asp Arg Asn Ala Val Leu Arg Glu Gly Asn Asn Arg Ser
        390                 395                 400 tac ttt ggc atc ttc aag gtg taaattggag agattatccc cggtcagaag         1908
Tyr Phe Gly Ile Phe Lys Val
    405 atggaatacc agtttaagct tttgtccccg cgactgctcg tgaatgcgat tcatcgccag    1968 cgtgaatcca ttagttcgta gtacctagtc ttagtcactc caaacctaat ctcaatcgga    2028 atcgtgcata ctgcattagt cagaagacgg aggaaaatca tatttatttt gtatatactc    2088 gttcgactct aaaagtgaa taaaaatata tgtagctatt aaaaaaaaaa aaaaaaaaa      2148 aaaaaaaaaa acctcgag                                                  2166

<210> SEQ ID NO 2
<211> LENGTH: 409
<212> TYPE: PRT
<213> ORGANISM: Drosophila melanogastor
```

```
<400> SEQUENCE: 2

Met Thr Ala Glu Thr Leu Lys Pro Phe Ile Thr Pro Thr Ser Ala Asn
1               5                   10                  15

Asp Asp Gly Phe Pro Ala Lys Ala Thr Ser Thr Ala Thr Ala Gln Arg
            20                  25                  30

Arg Thr Arg Gln Leu Ile Pro Leu Val Leu Gly Phe Ile Gly Leu Gly
        35                  40                  45

Leu Val Val Ala Ile Leu Ala Leu Thr Ile Trp Gln Thr Thr Arg Val
    50                  55                  60

Ser His Leu Asp Lys Glu Leu Lys Ser Leu Lys Arg Val Val Asp Asn
65                  70                  75                  80

Leu Gln Gln Arg Leu Gly Ile Asn Tyr Leu Asp Glu Phe Asp Glu Phe
                85                  90                  95

Gln Lys Glu Tyr Glu Asn Ala Leu Ile Asp Tyr Pro Lys Lys Val Asp
            100                 105                 110

Gly Leu Thr Asp Glu Glu Asp Asp Asp Gly Asp Gly Leu Asp Ser
            115                 120                 125

Ile Ala Asp Asp Glu Asp Asp Val Ser Tyr Ser Val Asp Asp
    130                 135                 140

Val Gly Ala Asp Tyr Glu Asp Tyr Thr Asp Met Leu Asn Lys Leu Asn
145                 150                 155                 160

Asn Ala His Thr Gly Thr Thr Pro Thr Ser Glu Thr Thr Ala Glu Gly
                165                 170                 175

Glu Gly Glu Thr Asp Ser Ala Ser Ser Ala Ser Asn Asp Asp Asn Val
            180                 185                 190

Phe Asp Asp Phe Thr Ser Ser Asp Ala Leu Lys Lys Lys Gln Glu Arg
            195                 200                 205

Lys Ser Arg Ser Ile Ala Asp Val Arg Asn Glu Glu Gln Asn Ile Gln
    210                 215                 220

Gly Asn His Thr Glu Leu Gln Glu Lys Ser Ser Asn Glu Ala Ala Ser
225                 230                 235                 240

Lys Glu Ser Pro Ala Ala Leu His Leu Arg Arg Met His Ser Arg
                245                 250                 255

His Arg His Leu Val Val Arg Lys Ala Arg Ser Glu Asp Ser Arg Pro
            260                 265                 270

Ala Ala His Phe His Leu Ser Ser Arg Arg His Gln Glu Ser Met
            275                 280                 285

Gly Tyr His Gly Asp Met Tyr Ile Glu Asn Asp Arg Glu Arg Cys Ser
    290                 295                 300

Tyr Gln Gly His Phe Gln Thr Arg Asp Gly Val Leu Thr Val Thr Asn
305                 310                 315                 320

Ala Gly Leu Tyr Tyr Val Tyr Ala Gln Ile Trp Gly Tyr Asn Ser His
            325                 330                 335

Asp Gln Asn Gly Phe Ile Val Phe Gln Gly Asp Thr Pro Phe Leu Gln
            340                 345                 350

Cys Leu Asn Thr Val Pro Thr Asn Met Pro His Lys Val His Thr Cys
        355                 360                 365

His Thr Ser Gly Leu Ile His Leu Glu Arg Asn Glu Arg Ile His Leu
    370                 375                 380

Lys Asp Ile His Asn Asp Arg Asn Ala Val Leu Arg Glu Gly Asn Asn
385                 390                 395                 400

Arg Ser Tyr Phe Gly Ile Phe Lys Val
```

-continued

```
                                405

<210> SEQ ID NO 3
<211> LENGTH: 1221
<212> TYPE: DNA
<213> ORGANISM: Drosophila melanogastor
<220> FEATURE:
<221> NAME/KEY: CDS
<222> LOCATION: (1)..(1218)

<400> SEQUENCE: 3 atg act gcc gag acc ctc aag ccg ttt ata acg cca acg agt gcc aac        48
Met Thr Ala Glu Thr Leu Lys Pro Phe Ile Thr Pro Thr Ser Ala Asn
 1               5                  10                  15 gat gat ggt ttt ccg gcc aaa gcg acc agc acg gcg acc gcc cag cga        96
Asp Asp Gly Phe Pro Ala Lys Ala Thr Ser Thr Ala Thr Ala Gln Arg
             20                  25                  30 cgc acc cgc cag ctg atc ccc ctg gtt ttg ggg ttc atc ggt ctg ggg       144
Arg Thr Arg Gln Leu Ile Pro Leu Val Leu Gly Phe Ile Gly Leu Gly
         35                  40                  45 ctg gtc gtt gcc att ctc gca cta acg atc tgg cag aca acg cgt gta       192
Leu Val Val Ala Ile Leu Ala Leu Thr Ile Trp Gln Thr Thr Arg Val
 50                  55                  60 tcg cat ctg gac aag gag ctg aag agc ctg aag cga gtc gtc gat aat       240
Ser His Leu Asp Lys Glu Leu Lys Ser Leu Lys Arg Val Val Asp Asn
 65                  70                  75                  80 ctc cag cag cgt ttg ggc ata aac tat ctg gac gag ttc gac gag ttc       288
Leu Gln Gln Arg Leu Gly Ile Asn Tyr Leu Asp Glu Phe Asp Glu Phe
                 85                  90                  95 caa aag gag tac gag aat gcc ctc atc gac tat cca aaa aag gtg gat       336
Gln Lys Glu Tyr Glu Asn Ala Leu Ile Asp Tyr Pro Lys Lys Val Asp
            100                 105                 110 ggc ctc acg gat gag gag gac gac gac gat ggc gat ggt ctg gat tcc       384
Gly Leu Thr Asp Glu Glu Asp Asp Asp Asp Gly Asp Gly Leu Asp Ser
        115                 120                 125 att gcg gac gac gag gac gac gac gtt agc tat agc tct gtg gat gat       432
Ile Ala Asp Asp Glu Asp Asp Asp Val Ser Tyr Ser Ser Val Asp Asp
    130                 135                 140 gtt ggc gca gac tac gag gac tac acc gat atg tta aat aaa ctc aac       480
Val Gly Ala Asp Tyr Glu Asp Tyr Thr Asp Met Leu Asn Lys Leu Asn
145                 150                 155                 160 aat gca cat acc ggc acc acg ccc aca tct gag acc act gct gag ggc       528
Asn Ala His Thr Gly Thr Thr Pro Thr Ser Glu Thr Thr Ala Glu Gly
                165                 170                 175 gag ggc gag acg gac agt gca tcc tca gcc tca aat gat gac aat gtg       576
Glu Gly Glu Thr Asp Ser Ala Ser Ser Ala Ser Asn Asp Asp Asn Val
            180                 185                 190 ttc gat gac ttt acc agc tac aat gcc cac aaa aag aag cag gag aga       624
Phe Asp Asp Phe Thr Ser Tyr Asn Ala His Lys Lys Lys Gln Glu Arg
        195                 200                 205 aaa tct cgc tcg att gcc gat gta cgc aat gag gag cag aat att caa       672
Lys Ser Arg Ser Ile Ala Asp Val Arg Asn Glu Glu Gln Asn Ile Gln
    210                 215                 220 gga aat cac aca gag ctt cag gaa aag tca tcc aat gag gca act tcc       720
Gly Asn His Thr Glu Leu Gln Glu Lys Ser Ser Asn Glu Ala Thr Ser
225                 230                 235                 240 aaa gag aga atg cat tcc cgc cat cgc cac ctc cta gtc cgc aaa ggt       768
Lys Glu Arg Met His Ser Arg His Arg His Leu Leu Val Arg Lys Gly
                245                 250                 255 gaa tct ctt ctt tca gcc aga tcc gag gac tcg agg cca gca gcc cat       816
Glu Ser Leu Leu Ser Ala Arg Ser Glu Asp Ser Arg Pro Ala Ala His
```

```
                  260                 265                 270
ttc cac ttg agc agc agg cgg cgt cac caa gga agt atg ggc tac cat     864
Phe His Leu Ser Ser Arg Arg Arg His Gln Gly Ser Met Gly Tyr His
        275                 280                 285 gga gat atg tac ata gga aat gat aac gag aga aac tct tat cag gga     912
Gly Asp Met Tyr Ile Gly Asn Asp Asn Glu Arg Asn Ser Tyr Gln Gly
    290                 295                 300 cac ttt caa acg cgc gat ggc gtc ttg acg gtg acc aat aca ggc cta     960
His Phe Gln Thr Arg Asp Gly Val Leu Thr Val Thr Asn Thr Gly Leu
305                 310                 315                 320 tat tac gta tac gcc cag ata tgc tac aac aac tcg cac gac cag aac    1008
Tyr Tyr Val Tyr Ala Gln Ile Cys Tyr Asn Asn Ser His Asp Gln Asn
                325                 330                 335 gga ttt atc gtc ttt caa gga gac act cca ttc ctg cag tgc ttg aac    1056
Gly Phe Ile Val Phe Gln Gly Asp Thr Pro Phe Leu Gln Cys Leu Asn
            340                 345                 350 acg gtg ccc acc aac atg cca cat aag gtg cac acc tgc cac acg agt    1104
Thr Val Pro Thr Asn Met Pro His Lys Val His Thr Cys His Thr Ser
        355                 360                 365 ggt ctg atc cac ctg gaa cga aac gag agg atc cat ctg aag gac att    1152
Gly Leu Ile His Leu Glu Arg Asn Glu Arg Ile His Leu Lys Asp Ile
370                 375                 380 cac aac gat cgc aat gca gtt ctg cgg gag gga aac aac cga agc tac    1200
His Asn Asp Arg Asn Ala Val Leu Arg Glu Gly Asn Asn Arg Ser Tyr
385                 390                 395                 400 ttt ggc atc ttc aag gtg taa                                        1221
Phe Gly Ile Phe Lys Val
            405

<210> SEQ ID NO 4
<211> LENGTH: 406
<212> TYPE: PRT
<213> ORGANISM: Drosophila melanogastor

<400> SEQUENCE: 4

Met Thr Ala Glu Thr Leu Lys Pro Phe Ile Thr Pro Thr Ser Ala Asn
1               5                   10                  15

Asp Asp Gly Phe Pro Ala Lys Ala Thr Ser Thr Ala Thr Ala Gln Arg
            20                  25                  30

Arg Thr Arg Gln Leu Ile Pro Leu Val Leu Gly Phe Ile Gly Leu Gly
        35                  40                  45

Leu Val Val Ala Ile Leu Ala Leu Thr Ile Trp Gln Thr Thr Arg Val
    50                  55                  60

Ser His Leu Asp Lys Glu Leu Lys Ser Leu Lys Arg Val Val Asp Asn
65                  70                  75                  80

Leu Gln Gln Arg Leu Gly Ile Asn Tyr Leu Asp Glu Phe Asp Glu Phe
                85                  90                  95

Gln Lys Glu Tyr Glu Asn Ala Leu Ile Asp Tyr Pro Lys Lys Val Asp
            100                 105                 110

Gly Leu Thr Asp Glu Glu Asp Asp Asp Gly Asp Gly Leu Asp Ser
        115                 120                 125

Ile Ala Asp Asp Glu Asp Asp Val Ser Tyr Ser Ser Val Asp Asp
    130                 135                 140

Val Gly Ala Asp Tyr Glu Asp Tyr Thr Asp Met Leu Asn Lys Leu Asn
145                 150                 155                 160

Asn Ala His Thr Gly Thr Thr Pro Thr Ser Glu Thr Thr Ala Glu Gly
                165                 170                 175
```

-continued

```
Glu Gly Glu Thr Asp Ser Ala Ser Ser Ala Ser Asn Asp Asn Val
                180                 185                 190

Phe Asp Asp Phe Thr Ser Tyr Asn Ala His Lys Lys Gln Glu Arg
            195                 200                 205

Lys Ser Arg Ser Ile Ala Asp Val Arg Asn Glu Glu Gln Asn Ile Gln
        210                 215                 220

Gly Asn His Thr Glu Leu Gln Glu Lys Ser Ser Asn Glu Ala Thr Ser
225                 230                 235                 240

Lys Glu Arg Met His Ser Arg His Arg His Leu Leu Val Arg Lys Gly
                245                 250                 255

Glu Ser Leu Leu Ser Ala Arg Ser Glu Asp Ser Arg Pro Ala Ala His
            260                 265                 270

Phe His Leu Ser Ser Arg Arg His Gln Gly Ser Met Gly Tyr His
        275                 280                 285

Gly Asp Met Tyr Ile Gly Asn Asp Asn Glu Arg Asn Ser Tyr Gln Gly
    290                 295                 300

His Phe Gln Thr Arg Asp Gly Val Leu Thr Val Thr Asn Thr Gly Leu
305                 310                 315                 320

Tyr Tyr Val Tyr Ala Gln Ile Cys Tyr Asn Asn Ser His Asp Gln Asn
                325                 330                 335

Gly Phe Ile Val Phe Gln Gly Asp Thr Pro Phe Leu Gln Cys Leu Asn
            340                 345                 350

Thr Val Pro Thr Asn Met Pro His Lys Val His Thr Cys His Thr Ser
        355                 360                 365

Gly Leu Ile His Leu Glu Arg Asn Glu Arg Ile His Leu Lys Asp Ile
    370                 375                 380

His Asn Asp Arg Asn Ala Val Leu Arg Glu Gly Asn Asn Arg Ser Tyr
385                 390                 395                 400

Phe Gly Ile Phe Lys Val
                405
```

<210> SEQ ID NO 5
<211> LENGTH: 2148
<212> TYPE: DNA
<213> ORGANISM: Drosophila melanogastor
<220> FEATURE:
<221> NAME/KEY: CDS
<222> LOCATION: (634)..(1860)

<400> SEQUENCE: 5

```
ggcacgaggc gaacggacgt ttaaagtgag aaaagaaacc ggtaaatcag agatcccaag      60
caagcgcgtg cgtgcatgat agcgaagaaa aaaagctatc cgtttcagtt aactacttac     120
caagattgaa tttcgccatc gggcaaatta ctaaaaatac ataagtgcaa ctcgtccact     180
gtgtgttgtg ttttttttt ttttttggt tttcgctgtg cctttatcgc aaacaagaac       240
tgataaaact agaaaatatc ttgagaaact tgttttcgcg cttttctttt gctaattgcc     300
gatcgcggaa gagaaaaaca agcagtagac aaaacaagtg tggtaataca atctgaaaag    360
ggcaccatca gcagcccgag gggtttatct atatagatgt cgcagcttat catctcatgc    420
tgtctgtgag gttgttctgt gtgctcgtgt agtatcttaa atacatagag tgtgttcata    480
taaagtgcga caaagctcga ttggaaacag ctgtcgagtg cccttgagtg ggtgggcaag    540
atcgtcatca tcatcatcgt cgtcattatc aacagaatca gcatcagcat ctggaggccc    600
cggttgctct aagatcccca gtgttcatca att atg act gcc gag acc ctc aag    654
                                     Met Thr Ala Glu Thr Leu Lys
                                     1               5
```

-continued

| | |
|---|---|
| ccg ttt ata acg cca acg agt gcc aac gat gat ggt ttt ccg gcc aaa<br>Pro Phe Ile Thr Pro Thr Ser Ala Asn Asp Asp Gly Phe Pro Ala Lys<br>          10                    15                  20 | 702 |
| gcg acc agc acg gcg acc gcc cag cga cgc acc cgc cag ctg atc ccc<br>Ala Thr Ser Thr Ala Thr Ala Gln Arg Arg Thr Arg Gln Leu Ile Pro<br>    25                    30                    35 | 750 |
| ctg gtt ttg ggg ttc atc ggt ctg ggg ctg gtc gtt gcc att ctc gca<br>Leu Val Leu Gly Phe Ile Gly Leu Gly Leu Val Val Ala Ile Leu Ala<br>40                    45                    50                    55 | 798 |
| cta acg atc tgg cag aca acg cgt gta tcg cat ctg gac aag gag ctg<br>Leu Thr Ile Trp Gln Thr Thr Arg Val Ser His Leu Asp Lys Glu Leu<br>                  60                    65                    70 | 846 |
| aag agc ctg aag cga gtc gtc gat aat ctc cag cag cgt ttg ggc ata<br>Lys Ser Leu Lys Arg Val Val Asp Asn Leu Gln Gln Arg Leu Gly Ile<br>              75                    80                    85 | 894 |
| aac tat ctg gac gag ttc gac gag ttc caa aag gag tac gag aat gcc<br>Asn Tyr Leu Asp Glu Phe Asp Glu Phe Gln Lys Glu Tyr Glu Asn Ala<br>              90                    95                  100 | 942 |
| ctc atc gac tat cca aaa aag gtg gat ggc ctc acg gat gag gag gac<br>Leu Ile Asp Tyr Pro Lys Lys Val Asp Gly Leu Thr Asp Glu Glu Asp<br>105                    110                    115 | 990 |
| gac gac gat ggc gat ggt ctg gat tcc att gcg gac gac gag gac gac<br>Asp Asp Asp Gly Asp Gly Leu Asp Ser Ile Ala Asp Asp Glu Asp Asp<br>120                    125                    130                    135 | 1038 |
| gac gtt agc tat agc tct gtg gat gat gtt ggc gca gac tac gag gac<br>Asp Val Ser Tyr Ser Ser Val Asp Asp Val Gly Ala Asp Tyr Glu Asp<br>                  140                    145                    150 | 1086 |
| tac acc gat atg tta aat aaa ctc aac aat gca cat acc ggc acc acg<br>Tyr Thr Asp Met Leu Asn Lys Leu Asn Asn Ala His Thr Gly Thr Thr<br>                  155                    160                    165 | 1134 |
| ccc aca tct gag acc act gct gag ggc gag ggc gag acg gac agt gca<br>Pro Thr Ser Glu Thr Thr Ala Glu Gly Glu Gly Glu Thr Asp Ser Ala<br>          170                    175                    180 | 1182 |
| tcc tca gcc tca aat gat gac aat gtg ttc gat gac ttt acc agc tac<br>Ser Ser Ala Ser Asn Asp Asp Asn Val Phe Asp Asp Phe Thr Ser Tyr<br>185                    190                    195 | 1230 |
| aat gcc cac aaa aag aag cag gag aga aaa tct cgc tcg att gcc gat<br>Asn Ala His Lys Lys Lys Gln Glu Arg Lys Ser Arg Ser Ile Ala Asp<br>200                    205                    210                    215 | 1278 |
| gta cgc aat gag gag cag aat att caa gga aat cac aca gag ctt cag<br>Val Arg Asn Glu Glu Gln Asn Ile Gln Gly Asn His Thr Glu Leu Gln<br>                  220                    225                    230 | 1326 |
| gaa aag tca tcc aat gag gca act tcc aaa gag agc cct gca cca ctt<br>Glu Lys Ser Ser Asn Glu Ala Thr Ser Lys Glu Ser Pro Ala Pro Leu<br>          235                    240                    245 | 1374 |
| cac cac cgt cgc aga atg cat tcc cgc cat cgc cac ctc cta gtc cgc<br>His His Arg Arg Arg Met His Ser Arg His Arg His Leu Leu Val Arg<br>250                    255                    260 | 1422 |
| aaa gcc aga tcc gag gac tcg agg cca gca gcc cat ttc cac ttg agc<br>Lys Ala Arg Ser Glu Asp Ser Arg Pro Ala Ala His Phe His Leu Ser<br>    265                    270                    275 | 1470 |
| agc agg cgg cgt cac caa gga agt atg ggc tac cat gga gat atg tac<br>Ser Arg Arg Arg His Gln Gly Ser Met Gly Tyr His Gly Asp Met Tyr<br>280                    285                    290                    295 | 1518 |
| ata gga aat gat aac gag aga aac tct tat cag gga cac ttt caa acg<br>Ile Gly Asn Asp Asn Glu Arg Asn Ser Tyr Gln Gly His Phe Gln Thr<br>                  300                    305                    310 | 1566 |
| cgc gat ggc gtc ttg acg gtg acc aat aca ggc cta tat tac gta tac<br>Arg Asp Gly Val Leu Thr Val Thr Asn Thr Gly Leu Tyr Tyr Val Tyr | 1614 |

-continued

```
              315                 320                 325
gcc cag ata tgc tac aac aac tcg cac gac cag aac gga ttt atc gtc    1662
Ala Gln Ile Cys Tyr Asn Asn Ser His Asp Gln Asn Gly Phe Ile Val
        330                 335                 340 ttt caa gga gac act cca ttc ctg cag tgc ttg aac acg gtg ccc acc    1710
Phe Gln Gly Asp Thr Pro Phe Leu Gln Cys Leu Asn Thr Val Pro Thr
345                 350                 355 aac atg cca cat aag gtg cac acc tgc cac acg agt ggt ctg atc cac    1758
Asn Met Pro His Lys Val His Thr Cys His Thr Ser Gly Leu Ile His
360                 365                 370                 375 ctg gaa cga aac gag agg atc cat ctg aag gac att cac aac gat cgc    1806
Leu Glu Arg Asn Glu Arg Ile His Leu Lys Asp Ile His Asn Asp Arg
                380                 385                 390 aat gca gtt ctg cgg gag gga aac aac cga agc tac ttt ggc atc ttc    1854
Asn Ala Val Leu Arg Glu Gly Asn Asn Arg Ser Tyr Phe Gly Ile Phe
        395                 400                 405 aag gtg taaattggag agattatccc cggtcagaag atggaatacc agtttaagct    1910
Lys Val tttgtccccg cgactgctcg tgaatgcgat tcatcgccag cgtgaatcca ttagttcgta   1970
gtacctagtc ttagtcactc caaacctaat ctcaatcgga atcgtgcata ctgcattagt   2030
cagaagacgg aggaaaatca tatttatttt gtatatactc gttcgactct aaaaagtgaa   2090
taaaaatata tgtagctatt aaaaaaaaaa aaaaaaaaaa aaaaaaaaaa aactcgag     2148
```

<210> SEQ ID NO 6
<211> LENGTH: 409
<212> TYPE: PRT
<213> ORGANISM: Drosophila melanogastor

<400> SEQUENCE: 6

```
Met Thr Ala Glu Thr Leu Lys Pro Phe Ile Thr Pro Thr Ser Ala Asn
1               5                   10                  15

Asp Asp Gly Phe Pro Ala Lys Ala Thr Ser Thr Ala Thr Ala Gln Arg
            20                  25                  30

Arg Thr Arg Gln Leu Ile Pro Leu Val Leu Gly Phe Ile Gly Leu Gly
        35                  40                  45

Leu Val Val Ala Ile Leu Ala Leu Thr Ile Trp Gln Thr Thr Arg Val
    50                  55                  60

Ser His Leu Asp Lys Glu Leu Lys Ser Leu Lys Arg Val Val Asp Asn
65                  70                  75                  80

Leu Gln Gln Arg Leu Gly Ile Asn Tyr Leu Asp Glu Phe Asp Glu Phe
                85                  90                  95

Gln Lys Glu Tyr Glu Asn Ala Leu Ile Asp Tyr Pro Lys Lys Val Asp
            100                 105                 110

Gly Leu Thr Asp Glu Glu Asp Asp Asp Gly Asp Leu Asp Ser
        115                 120                 125

Ile Ala Asp Asp Glu Asp Asp Val Ser Tyr Ser Ser Val Asp Asp
    130                 135                 140

Val Gly Ala Asp Tyr Glu Asp Tyr Thr Asp Met Leu Asn Lys Leu Asn
145                 150                 155                 160

Asn Ala His Thr Gly Thr Thr Pro Thr Ser Glu Thr Thr Ala Glu Gly
                165                 170                 175

Glu Gly Glu Thr Asp Ser Ala Ser Ser Ala Ser Asn Asp Asp Asn Val
            180                 185                 190

Phe Asp Asp Phe Thr Ser Tyr Asn Ala His Lys Lys Gln Glu Arg
        195                 200                 205
```

-continued

Lys Ser Arg Ser Ile Ala Asp Val Arg Asn Glu Glu Gln Asn Ile Gln
210                 215                 220

Gly Asn His Thr Glu Leu Gln Glu Lys Ser Ser Asn Glu Ala Thr Ser
225                 230                 235                 240

Lys Glu Ser Pro Ala Pro Leu His His Arg Arg Met His Ser Arg
            245                 250                 255

His Arg His Leu Leu Val Arg Lys Ala Arg Ser Glu Asp Ser Arg Pro
            260                 265                 270

Ala Ala His Phe His Leu Ser Ser Arg Arg His Gln Gly Ser Met
            275                 280                 285

Gly Tyr His Gly Asp Met Tyr Ile Gly Asn Asp Glu Arg Asn Ser
290                 295                 300

Tyr Gln Gly His Phe Gln Thr Arg Asp Gly Val Leu Thr Val Thr Asn
305                 310                 315                 320

Thr Gly Leu Tyr Tyr Val Tyr Ala Gln Ile Cys Tyr Asn Asn Ser His
                325                 330                 335

Asp Gln Asn Gly Phe Ile Val Phe Gln Gly Asp Thr Pro Phe Leu Gln
                340                 345                 350

Cys Leu Asn Thr Val Pro Thr Asn Met Pro His Lys Val His Thr Cys
            355                 360                 365

His Thr Ser Gly Leu Ile His Leu Glu Arg Asn Glu Arg Ile His Leu
            370                 375                 380

Lys Asp Ile His Asn Asp Arg Asn Ala Val Leu Arg Glu Gly Asn Asn
385                 390                 395                 400

Arg Ser Tyr Phe Gly Ile Phe Lys Val
                    405

<210> SEQ ID NO 7
<211> LENGTH: 317
<212> TYPE: PRT
<213> ORGANISM: Drosophila melanogaster

<400> SEQUENCE: 7

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
                20                  25                  30

Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro

```
                     165                 170                 175
Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 8
<211> LENGTH: 391
<212> TYPE: PRT
<213> ORGANISM: Drosophila melanogaster

<400> SEQUENCE: 8

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
    130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Gly Pro Pro Gly
            180                 185                 190

Pro Pro Gly Pro Gln Gly Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220
```

```
Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
            245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
    370                 375                 380

Leu Gly Glu Ala Pro Ala Ser
385                 390

<210> SEQ ID NO 9
<211> LENGTH: 391
<212> TYPE: PRT
<213> ORGANISM: Mus musculus

<400> SEQUENCE: 9

Met Gly Tyr Pro Glu Val Glu Arg Arg Glu Pro Leu Pro Ala Ala Ala
1               5                   10                  15

Pro Arg Glu Arg Gly Ser Gln Gly Cys Gly Cys Arg Gly Ala Pro Ala
            20                  25                  30

Arg Ala Gly Glu Gly Asn Ser Cys Arg Leu Phe Leu Gly Phe Phe Gly
        35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Thr Glu Ser Arg Leu Gly Gly
65                  70                  75                  80

Pro Gly Ala Pro Gly Thr Ser Gly Thr Leu Ser Ser Pro Gly Ser Leu
            85                  90                  95

Asp Pro Val Gly Pro Ile Thr Arg His Leu Gly Gln Pro Ser Phe Gln
            100                 105                 110

Gln Gln Pro Leu Glu Pro Gly Glu Asp Pro Leu Pro Asp Ser Gln
        115                 120                 125

Asp Arg His Gln Met Ala Leu Leu Asn Phe Phe Pro Asp Glu Lys
    130                 135                 140

Ala Tyr Ser Glu Glu Ser Arg Arg Val Arg Arg Asn Lys Arg Ser
145                 150                 155                 160

Lys Ser Gly Glu Gly Ala Asp Gly Pro Val Lys Asn Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205
```

-continued

```
Pro Gly Thr Thr Val Met Gly Pro Gly Pro Pro Gly
    210             215             220
Pro Gln Gly Pro Pro Gly Leu Gln Gly Pro Ser Gly Ala Ala Asp Lys
225             230             235             240
Thr Gly Thr Arg Glu Asn Gln Pro Ala Val His Leu Gln Gly Gln
            245             250             255
Gly Ser Ala Ile Gln Val Lys Asn Asp Leu Ser Gly Gly Val Leu Asn
        260             265             270
Asp Trp Ser Arg Ile Thr Met Asn Pro Lys Val Phe Lys Leu His Pro
        275             280             285
Arg Ser Gly Glu Leu Glu Val Leu Val Asp Gly Thr Tyr Phe Ile Tyr
    290             295             300
Ser Gln Val Glu Val Tyr Tyr Ile Asn Phe Thr Asp Phe Ala Ser Tyr
305             310             315             320
Glu Val Val Asp Glu Lys Pro Phe Leu Gln Cys Thr Arg Ser Ile
            325             330             335
Glu Thr Gly Lys Thr Asn Tyr Asn Thr Cys Tyr Thr Ala Gly Val Cys
        340             345             350
Leu Leu Lys Ala Arg Gln Lys Ile Ala Val Lys Met Val His Ala Asp
        355             360             365
Ile Ser Ile Asn Met Ser Lys His Thr Thr Phe Phe Gly Ala Ile Arg
    370             375             380
Leu Gly Glu Ala Pro Ala Ser
385             390
```

<210> SEQ ID NO 10
<211> LENGTH: 423
<212> TYPE: DNA
<213> ORGANISM: Drosophila melanogaster

<400> SEQUENCE: 10

```
tcgcaaaagg tcggtgctgc tgagcaataa aggtattaat ttatgaaatc attgttgcgc    60
aaagaaattg atcagaggaa tatgaaaata atcgaatcga gacggcacgt ctaaaaggtt   120
gatgtacaat attgtaacat tcagtgcata gcgacatcca gtgcagcaag taaattaagc   180
gaacaagatg gattccaaag tgggtgcaga tcctagttcg gcctacgaca aggaaatcgg   240
caacaatcta aacaacgatg attcctcatt tctgggcaac ataatccgcg aaatcctgta   300
cagtccaatg aacctggccc tcctggccat catctgcttc ctggtctata aaatcgttcg   360
ggatcgcacc gaagtgccat ccgtgggcgt tgcaaagcca tccgaacctg agttacccaa   420
aat                                                                 423
```

<210> SEQ ID NO 11
<211> LENGTH: 24
<212> TYPE: DNA
<213> ORGANISM: Drosophila melanogaster

<400> SEQUENCE: 11

```
accagaacgg atttatcgtc tttc                                           24
```

<210> SEQ ID NO 12
<211> LENGTH: 18
<212> TYPE: DNA
<213> ORGANISM: Drosophila melanogaster

<400> SEQUENCE: 12

```
gttggtgggc accgtgtt                                                    18
```

<210> SEQ ID NO 13
<211> LENGTH: 19
<212> TYPE: DNA
<213> ORGANISM: Drosophila melanogaster

<400> SEQUENCE: 13

```
gaccatccgc ccagcatac                                                   19
```

<210> SEQ ID NO 14
<211> LENGTH: 19
<212> TYPE: DNA
<213> ORGANISM: Drosophila melanogaster

<400> SEQUENCE: 14

```
actggtggcg gatgaagtg                                                   19
```

<210> SEQ ID NO 15
<211> LENGTH: 193
<212> TYPE: PRT
<213> ORGANISM: Drosophila melanogaster

<400> SEQUENCE: 15

```
Met Pro Glu Glu Gly Ser Gly Cys Ser Val Arg Arg Pro Tyr Gly
1               5                   10                  15

Cys Val Leu Arg Ala Ala Leu Val Pro Leu Ala Gly Leu Val Ile
                20                  25                  30

Cys Leu Val Val Cys Ile Gln Arg Phe Ala Gln Ala Gln Gln Leu
                35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
                115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Val Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro
```

<210> SEQ ID NO 16
<211> LENGTH: 234
<212> TYPE: PRT
<213> ORGANISM: Drosophila melanogaster

<400> SEQUENCE: 16

```
Met Asp Pro Gly Leu Gln Gln Ala Leu Asn Gly Met Ala Pro Gly
1               5                   10                  15
```

```
Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
 50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
210                 215                 220

Leu Ser Ile Phe Leu Tyr Ser Asn Ser Asp
225                 230

<210> SEQ ID NO 17
<211> LENGTH: 281
<212> TYPE: PRT
<213> ORGANISM: Drosophila melanogaster

<400> SEQUENCE: 17

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
 50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160
```

```
His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                    245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 18
<211> LENGTH: 16
<212> TYPE: PRT
<213> ORGANISM: Drosophila melanogaster

<400> SEQUENCE: 18

Leu Thr Val Thr Asn Ala Gly Leu Tyr Tyr Val Tyr Ala Gln Ile Trp
1               5                   10                  15

<210> SEQ ID NO 19
<211> LENGTH: 17
<212> TYPE: PRT
<213> ORGANISM: Drosophila melanogaster

<400> SEQUENCE: 19

Leu Thr Val Thr Asn Thr Gly Leu Tyr Tyr Val Tyr Ala Gln Ile Cys
1               5                   10                  15
Tyr

<210> SEQ ID NO 20
<211> LENGTH: 17
<212> TYPE: PRT
<213> ORGANISM: Drosophila melanogaster

<400> SEQUENCE: 20

Leu Thr Val Thr Asn Thr Gly Leu Tyr Tyr Val Tyr Ala Gln Ile Cys
1               5                   10                  15
Tyr

<210> SEQ ID NO 21
<211> LENGTH: 36
<212> TYPE: DNA
<213> ORGANISM: Drosophila melanogaster

<400> SEQUENCE: 21
cggaaagatc taacgcgtgt atcgcatctg gacaag                              36

<210> SEQ ID NO 22
<211> LENGTH: 30
<212> TYPE: DNA
<213> ORGANISM: Drosophila melanogaster

<400> SEQUENCE: 22
```

```
gcctctagaa atttacacct tgaagatgcc                                    30

<210> SEQ ID NO 23
<211> LENGTH: 38
<212> TYPE: DNA
<213> ORGANISM: Drosophila melanogaster

<400> SEQUENCE: 23
gcagcagcgg ccgcattctc gcactaacga tctggcag                           38

<210> SEQ ID NO 24
<211> LENGTH: 35
<212> TYPE: DNA
<213> ORGANISM: Drosophila melanogaster

<400> SEQUENCE: 24
gcagcagtcg accaccttga agatgccaaa gtagc                              35

<210> SEQ ID NO 25
<211> LENGTH: 38
<212> TYPE: DNA
<213> ORGANISM: Drosophila melanogaster

<400> SEQUENCE: 25
gcagcagcgg ccgcatgact gccgagaccc tcaagccg                           38

<210> SEQ ID NO 26
<211> LENGTH: 36
<212> TYPE: DNA
<213> ORGANISM: Drosophila melanogaster

<400> SEQUENCE: 26
gcagcagtcg actacgccat cgcgcgtttg aaagtg                             36

<210> SEQ ID NO 27
<211> LENGTH: 38
<212> TYPE: DNA
<213> ORGANISM: Drosophila melanogaster

<400> SEQUENCE: 27
gcagcagcgg ccgcattctc gcactaacga tctggcag                           38

<210> SEQ ID NO 28
<211> LENGTH: 35
<212> TYPE: DNA
<213> ORGANISM: Drosophila melanogaster

<400> SEQUENCE: 28
gcagcagtcg accaccttga agatgccaaa gtagc                              35

<210> SEQ ID NO 29
<211> LENGTH: 38
<212> TYPE: DNA
<213> ORGANISM: Drosophila melanogaster

<400> SEQUENCE: 29
gcagcagcgg ccgcatgact gccgagaccc tcaagccg                           38

<210> SEQ ID NO 30
<211> LENGTH: 36
<212> TYPE: DNA
<213> ORGANISM: Drosophila melanogaster
```

-continued

<400> SEQUENCE: 30
gcagcagtcg acgacgccat cgcgcgtttg aaagtg                                   36

<210> SEQ ID NO 31
<211> LENGTH: 38
<212> TYPE: DNA
<213> ORGANISM: Drosophila melanogaster

<400> SEQUENCE: 31
gcagcagcgg ccgcattctc gcactaacga tctggcag                                 38

<210> SEQ ID NO 32
<211> LENGTH: 35
<212> TYPE: DNA
<213> ORGANISM: Drosophila melanogaster

<400> SEQUENCE: 32
gcagcagtcg accaccttga agatgccaaa gtagc                                    35

<210> SEQ ID NO 33
<211> LENGTH: 38
<212> TYPE: DNA
<213> ORGANISM: Drosophila melanogaster

<400> SEQUENCE: 33
gcagcagcgg ccgcatgact gccgagaccc tcaagccg                                 38

<210> SEQ ID NO 34
<211> LENGTH: 37
<212> TYPE: DNA
<213> ORGANISM: Drosophila melanogaster

<400> SEQUENCE: 34
gcagcagtcg accaagacgc catcgcgcgt ttgaaag                                  37

<210> SEQ ID NO 35
<211> LENGTH: 14
<212> TYPE: PRT
<213> ORGANISM: Drosophila melanogaster

<400> SEQUENCE: 35

Gln Asn Ile Gln Gly Asn His Thr Glu Leu Gln Glu Lys Ser
1               5                   10

<210> SEQ ID NO 36
<211> LENGTH: 14
<212> TYPE: PRT
<213> ORGANISM: Drosophila melanogaster

<400> SEQUENCE: 36

Leu Arg Glu Gly Asn Asn Arg Ser Tyr Phe Gly Ile Phe Lys
1               5                   10

<210> SEQ ID NO 37
<211> LENGTH: 12
<212> TYPE: PRT
<213> ORGANISM: Drosophila melanogaster

<400> SEQUENCE: 37

Met Thr Ala Glu Thr Leu Lys Pro Phe Ile Thr Pro
1               5                   10

<210> SEQ ID NO 38

```
<211> LENGTH: 13
<212> TYPE: PRT
<213> ORGANISM: Drosophila melanogaster

<400> SEQUENCE: 38

Leu Thr Ile Trp Gln Thr Thr Arg Val Ser His Leu Asp
1               5                   10

<210> SEQ ID NO 39
<211> LENGTH: 13
<212> TYPE: PRT
<213> ORGANISM: Drosophila melanogaster

<400> SEQUENCE: 39

Asp Lys Glu Leu Lys Ser Leu Lys Arg Val Val Asp Asn
1               5                   10

<210> SEQ ID NO 40
<211> LENGTH: 13
<212> TYPE: PRT
<213> ORGANISM: Drosophila melanogaster

<400> SEQUENCE: 40

Ala His Phe His Leu Ser Ser Arg Arg His Gln Glu
1               5                   10

<210> SEQ ID NO 41
<211> LENGTH: 13
<212> TYPE: PRT
<213> ORGANISM: Drosophila melanogaster

<400> SEQUENCE: 41

His Phe His Leu Ser Ser Arg Arg Arg His Gln Glu Ser
1               5                   10

<210> SEQ ID NO 42
<211> LENGTH: 20
<212> TYPE: PRT
<213> ORGANISM: Drosophila melanogaster

<400> SEQUENCE: 42

His Leu Ser Ser Arg Arg Arg His Gln Glu Ser Met Gly Tyr His Gly
1               5                   10                  15

Asp Met Tyr Tyr
            20

<210> SEQ ID NO 43
<211> LENGTH: 18
<212> TYPE: PRT
<213> ORGANISM: Drosophila melanogaster

<400> SEQUENCE: 43

Leu Ser Ser Arg Arg Arg His Gln Glu Ser Met Gly Tyr His Gly Asp
1               5                   10                  15

Met Tyr

<210> SEQ ID NO 44
<211> LENGTH: 14
<212> TYPE: PRT
<213> ORGANISM: Drosophila melanogaster

<400> SEQUENCE: 44

Gln Asn Ile Gln Gly Asn His Thr Glu Leu Gln Glu Lys Ser
1               5                   10
```

```
<210> SEQ ID NO 45
<211> LENGTH: 14
<212> TYPE: PRT
<213> ORGANISM: Drosophila melanogaster

<400> SEQUENCE: 45

Ala Gln Ile Cys Tyr Asn Asn Ser His Asp Gln Asn Gly Phe
1               5                   10

<210> SEQ ID NO 46
<211> LENGTH: 14
<212> TYPE: PRT
<213> ORGANISM: Drosophila melanogaster

<400> SEQUENCE: 46

Leu Arg Glu Gly Asn Asn Arg Ser Tyr Phe Gly Ile Phe Lys
1               5                   10

<210> SEQ ID NO 47
<211> LENGTH: 12
<212> TYPE: PRT
<213> ORGANISM: Drosophila melanogaster

<400> SEQUENCE: 47

Met Thr Ala Glu Thr Leu Lys Pro Phe Ile Thr Pro
1               5                   10

<210> SEQ ID NO 48
<211> LENGTH: 13
<212> TYPE: PRT
<213> ORGANISM: Drosophila melanogaster

<400> SEQUENCE: 48

Leu Thr Ile Trp Gln Thr Thr Arg Val Ser His Leu Asp
1               5                   10

<210> SEQ ID NO 49
<211> LENGTH: 13
<212> TYPE: PRT
<213> ORGANISM: Drosophila melanogaster

<400> SEQUENCE: 49

Asp Lys Glu Leu Lys Ser Leu Lys Arg Val Val Asp Asn
1               5                   10

<210> SEQ ID NO 50
<211> LENGTH: 13
<212> TYPE: PRT
<213> ORGANISM: Drosophila melanogaster

<400> SEQUENCE: 50

Ser Ser Asn Glu Ala Thr Ser Lys Glu Arg Met His Ser
1               5                   10

<210> SEQ ID NO 51
<211> LENGTH: 13
<212> TYPE: PRT
<213> ORGANISM: Drosophila melanogaster

<400> SEQUENCE: 51

Gly Glu Ser Leu Leu Ser Ala Arg Ser Glu Asp Ser Arg
1               5                   10
```

```
<210> SEQ ID NO 52
<211> LENGTH: 13
<212> TYPE: PRT
<213> ORGANISM: Drosophila melanogaster

<400> SEQUENCE: 52

Ala His Phe His Leu Ser Ser Arg Arg Arg His Gln Gly
1               5                   10

<210> SEQ ID NO 53
<211> LENGTH: 13
<212> TYPE: PRT
<213> ORGANISM: Drosophila melanogaster

<400> SEQUENCE: 53

His Phe His Leu Ser Ser Arg Arg Arg His Gln Gly Ser
1               5                   10

<210> SEQ ID NO 54
<211> LENGTH: 27
<212> TYPE: PRT
<213> ORGANISM: Drosophila melanogaster

<400> SEQUENCE: 54

Thr Arg Asp Gly Val Leu Thr Val Thr Asn Thr Gly Leu Tyr Tyr Val
1               5                   10                  15

Tyr Ala Gln Ile Cys Tyr Asn Asn Ser His Asp
            20                  25

<210> SEQ ID NO 55
<211> LENGTH: 14
<212> TYPE: PRT
<213> ORGANISM: Drosophila melanogaster

<400> SEQUENCE: 55

Gln Asn Ile Gln Gly Asn His Thr Glu Leu Gln Glu Lys Ser
1               5                   10

<210> SEQ ID NO 56
<211> LENGTH: 14
<212> TYPE: PRT
<213> ORGANISM: Drosophila melanogaster

<400> SEQUENCE: 56

Ala Gln Ile Cys Tyr Asn Asn Ser His Asp Gln Asn Gly Phe
1               5                   10

<210> SEQ ID NO 57
<211> LENGTH: 14
<212> TYPE: PRT
<213> ORGANISM: Drosophila melanogaster

<400> SEQUENCE: 57

Leu Arg Glu Gly Asn Asn Arg Ser Tyr Phe Gly Ile Phe Lys
1               5                   10

<210> SEQ ID NO 58
<211> LENGTH: 12
<212> TYPE: PRT
<213> ORGANISM: Drosophila melanogaster

<400> SEQUENCE: 58

Met Thr Ala Glu Thr Leu Lys Pro Phe Ile Thr Pro
1               5                   10
```

```
<210> SEQ ID NO 59
<211> LENGTH: 13
<212> TYPE: PRT
<213> ORGANISM: Drosophila melanogaster

<400> SEQUENCE: 59

Leu Thr Ile Trp Gln Thr Thr Arg Val Ser His Leu Asp
1               5                   10

<210> SEQ ID NO 60
<211> LENGTH: 13
<212> TYPE: PRT
<213> ORGANISM: Drosophila melanogaster

<400> SEQUENCE: 60

Asp Lys Glu Leu Lys Ser Leu Lys Arg Val Val Asp Asn
1               5                   10

<210> SEQ ID NO 61
<211> LENGTH: 13
<212> TYPE: PRT
<213> ORGANISM: Drosophila melanogaster

<400> SEQUENCE: 61

Ser Ser Asn Glu Ala Thr Ser Lys Glu Ser Pro Ala Pro
1               5                   10

<210> SEQ ID NO 62
<211> LENGTH: 13
<212> TYPE: PRT
<213> ORGANISM: Drosophila melanogaster

<400> SEQUENCE: 62

Ala His Phe His Leu Ser Ser Arg Arg Arg His Gln Gly
1               5                   10

<210> SEQ ID NO 63
<211> LENGTH: 13
<212> TYPE: PRT
<213> ORGANISM: Drosophila melanogaster

<400> SEQUENCE: 63

His Phe His Leu Ser Ser Arg Arg Arg His Gln Gly Ser
1               5                   10

<210> SEQ ID NO 64
<211> LENGTH: 27
<212> TYPE: PRT
<213> ORGANISM: Drosophila melanogaster

<400> SEQUENCE: 64

Thr Arg Asp Gly Val Leu Thr Val Thr Asn Thr Gly Leu Tyr Tyr Val
1               5                   10                  15

Tyr Ala Gln Ile Cys Tyr Asn Asn Ser His Asp
            20                  25

<210> SEQ ID NO 65
<211> LENGTH: 8
<212> TYPE: PRT
<213> ORGANISM: bacteriophage T7
```

```
-continued
<400> SEQUENCE: 65

Asp Tyr Lys Asp Asp Asp Lys
1               5
```